(12) United States Patent
Kellis et al.

(10) Patent No.: US 10,774,326 B2
(45) Date of Patent: Sep. 15, 2020

(54) COMPOSITIONS AND METHODS FOR MANIPULATION OF ADIPOCYTE ENERGY CONSUMPTION REGULATORY PATHWAY

(71) Applicants: MASSACHUSETTS INSTITUTE OF TECHNOLOGY, Cambridge, MA (US); EUROPEAN MOLECULAR BIOLOGY LABORATORY, Heidelberg (DE)

(72) Inventors: Manolis Kellis, Brookline, MA (US); Melina Christine Claussnitzer, Somerville, MA (US); Jan Korbel, Heidelberg (DE)

(73) Assignees: MASSACHUSETTS INSTITUTE OF TECHNOLOGY, Cambridge, MA (US); EUROPEAN MOLECULAR BIOLOGY LABORATORY, Heidelberg (DE)

( * ) Notice: Subject to any disclaimer, the term of this patent is extended or adjusted under 35 U.S.C. 154(b) by 0 days.

(21) Appl. No.: 15/539,621

(22) PCT Filed: Dec. 23, 2015

(86) PCT No.: PCT/US2015/000311
§ 371 (c)(1),
(2) Date: Jun. 23, 2017

(87) PCT Pub. No.: WO2016/105535
PCT Pub. Date: Jun. 30, 2016

(65) Prior Publication Data
US 2019/0136232 A1    May 9, 2019

Related U.S. Application Data

(60) Provisional application No. 62/207,365, filed on Aug. 19, 2015, provisional application No. 62/206,841, filed on Aug. 18, 2015, provisional application No. 62/096,737, filed on Dec. 24, 2014.

(51) Int. Cl.
C12N 15/113   (2010.01)
A61K 31/713   (2006.01)
C12N 15/90   (2006.01)

(52) U.S. Cl.
CPC .......... *C12N 15/113* (2013.01); *A61K 31/713* (2013.01); *C12N 15/907* (2013.01); *C12N 2310/11* (2013.01); *C12N 2310/14* (2013.01); *C12N 2310/141* (2013.01); *C12N 2310/20* (2017.05); *C12N 2800/80* (2013.01)

(58) Field of Classification Search
None
See application file for complete search history.

(56) References Cited

U.S. PATENT DOCUMENTS

2005/0255487 A1* 11/2005 Khvorova ............ A61K 31/713
                                                             435/6.11
2007/0203083 A1   8/2007 Mootha et al.
2011/0123981 A1   5/2011 Dina et al.
2014/0148383 A1   5/2014 Huang et al.

FOREIGN PATENT DOCUMENTS

WO   WO 2005/110464 A2   11/2005
WO   WO 2016/105535 A2   6/2016

OTHER PUBLICATIONS

Tisdale "Mechanisms of Cancer Cachexia" 80 Physiological Reviews 381-410 (2009).*
Scarlett et al., "Iroquois homeobox gene 3 is temporally regulated in response to vascular endothelial growth factor and modulates endothelial cell migration and tubulogenesis" 73(19) Cancer Research Supplement C38 (Oct. 2013).*
Hofker et al., "The genome revolution and its role in understanding complex diseases" 1842 Biochimica et Biophysica Acta 1889-1895 (May 13, 2014).*
Dankel et al., "Switch from Stress Response to Homeobox Transcription Factors in Adipose Tissue After Profound Fat Loss" 5(6) PLoS One e11033 1-12 (2010).*
Bello, N.T. and Liang, N.-C., "The use of serotonergic drugs to treat obesity—is there any hope?," Drug Design, Development and Therapy, vol. 5; 95-109 (2011).
Claussnitzer, Ph.D., M. et al., "FTO Obesity Variant Circuitry and Adipocyte Browning in Humans," The New England Journal of Medicine, vol. 373; No. 10; 895-907 (2015).
International Preliminary Report on Patentability for Int'l Application No. PCT/US2015/000311, titled: Compositions and Methods for Manipulation of Adipocyte Energy Consumption Regulatory Pathway; dated Jun. 27, 2017.
Bracci; "Obesity and pancreatic cancer: overview of epidemiologic evidence and biologic mechanisms;" Mol. Carcinog. vol. 51(1), Jan. 2012; pp. 1-14, 14 pages.
Smemo et al.; "Obesity-associated variants within *FTO* form long-range functional connections with *IRX3*;" Nature (Mar. 2014), vol. 507: 371; 17 pages.
Yamakawa et al.; "Modulator recognition factor-2 regulates triglyceride metabolism in adipocytes;" Biochemical and Biophysical Research Communications; vol. 391 (2009); pp. 277-281.
International Search Report and Written Opinion dated Jul. 12, 2016; International Application No. PCT/US2015/000311; Filed on Dec. 23, 2015; 13 pages.

* cited by examiner

*Primary Examiner* — Nancy J Leith
(74) *Attorney, Agent, or Firm* — Hamilton, Brook, Smith & Reynolds, P.C.

(57) ABSTRACT

Provided herein is a pathway for adipocyte energy consumption regulation involving ARID5B, genetic variant rs1421085, IRX3, and IRX5. Compositions and methods for modulating the pathway in vitro and in vivo for anti-cachectic and anti-obesity effects are provided. Methods of identifying subjects at risk of developing a disorder mediated by a dysregulation of the energy consumption pathway are also provided.

19 Claims, 28 Drawing Sheets
Specification includes a Sequence Listing.

| | | Correlation (r) | | risk/non-risk (n=20, n=20) | | siARID5B/siNT risk individuals | | siARID5B/siNT non-risk | | siARID5B risk/non-risk | | CRISPR/Cas9 CC/CC-->TT | |
|---|---|---|---|---|---|---|---|---|---|---|---|---|---|
| | Gene | IRX3 | IRX5 | Fold | Pval | Fold | Pval | Fold | Pval | Fold | Pval | Fold | Pval |
| Mitochondrial function | ATP5S | -0.87 | -0.58 | -2.16 | 0.002 | 1.21 | n.s. | -1.58 | 0.03 | -1.15 | n.s. | -1.98 | <0.001 |
| | NDUFB6 | -0.85 | -0.65 | -1.63 | <0.001 | 1.45 | n.s. | -1.73 | 0.01 | 1.84 | n.s. | -2.43 | 0.03 |
| | COX11 | -0.84 | -0.69 | -2.01 | 0.006 | 1.32 | n.s. | -1.52 | 0.006 | 1.13 | n.s. | -4.01 | 0.01 |
| | ATPAF1 | -0.82 | -0.7 | -1.98 | 0.002 | 1.63 | n.s. | -2.98 | <0.001 | 1.24 | n.s. | -1.93 | 0.001 |
| | MAPK10 | -0.82 | -0.79 | -1.27 | 0.04 | -1.02 | n.s. | -1.61 | 0.008 | 1.12 | n.s. | -1.78 | <0.001 |
| | ATP5J | -0.81 | -0.16 | -1.41 | 0.002 | 1.82 | n.s. | -1.38 | <0.001 | -1.03 | n.s. | -3.45 | 0.008 |
| | COX7B | -0.57 | -0.8 | -2.46 | <0.001 | 1.08 | n.s. | -2.61 | <0.001 | 1.52 | n.s. | -2.98 | 0.01 |
| | ATP5B | -0.78 | -0.46 | -1.59 | 0.05 | -1.28 | n.s. | -2.56 | 0.05 | -1.42 | n.s. | -2.37 | 0.04 |
| | NDUFB5 | -0.77 | -0.68 | -1.91 | 0.04 | 1.31 | n.s. | -1.89 | <0.001 | 1.25 | n.s. | -3.02 | 0.002 |
| | ATP5L2 | -0.75 | -0.66 | -1.31 | 0.001 | -1.41 | n.s. | -1.62 | 0.001 | 1.03 | n.s. | -1.37 | <0.001 |
| FXR/RXR activation | HNF1A | 0.89 | 0.74 | 1.87 | 0.01 | 1.29 | n.s. | 1.39 | <0.001 | 1.53 | n.s. | 3.06 | 0.006 |
| | APOA4 | 0.89 | 0.73 | 1.63 | 0.001 | -1.42 | n.s. | 1.83 | <0.001 | 1.04 | n.s. | 1.89 | <0.001 |
| | FOXO1 | 0.74 | 0.87 | 2.12 | 0.06 | 1 | n.s. | 1.96 | n.s. | 1.32 | n.s. | 1.58 | 0.002 |
| | APOC4 | 0.5 | 0.86 | 2.32 | n.s. | 1.07 | n.s. | -1.28 | 0.008 | 1.65 | n.s. | 2.64 | 0.01 |
| | HNF4A | 0.79 | 0.86 | 2.54 | 0.03 | -1.19 | n.s. | 2.36 | 0.03 | 1.27 | n.s. | 2.92 | 0.03 |
| | SULT2A1 | 0.85 | 0.77 | 2.65 | 0.002 | 1.21 | n.s. | 1.78 | 0.04 | 1.02 | n.s. | 1.67 | 0.06 |
| | VTN | 0.83 | 0.74 | 1.32 | <0.001 | 1.08 | n.s. | 1.42 | <0.001 | 1 | n.s. | 2.23 | <0.001 |
| | PKLR | 0.82 | 0.68 | 2.35 | 0.003 | 1.52 | n.s. | 2.48 | 0.001 | -1.72 | n.s. | 2.54 | 0.008 |
| | FOXA2 | 0.66 | 0.81 | 2.56 | 0.001 | 1.48 | n.s. | 1.38 | 0.08 | -1.02 | n.s. | 1.69 | <0.001 |
| | APOC3 | 0.8 | 0.57 | 1.28 | 0.06 | 1.09 | n.s. | 1.65 | <0.001 | 1.18 | n.s. | 3.47 | n.s. |
| Corresp. Fig. | | Fig. 2A | | Fig. 1F | | | | Fig. 10H | | | | Fig. 4A | |

FIG. 6E

SEQUENCE LISTING

```
<160> NUMBER OF SEQ ID NOS: 54

<210> SEQ ID NO 1
<211> LENGTH: 21
<212> TYPE: RNA
<213> ORGANISM: Artificial Sequence
<220> FEATURE:
<223> OTHER INFORMATION: siRNA

<400> SEQUENCE: 1
cagcugggau accaauacau u                                              21

<210> SEQ ID NO 2
<211> LENGTH: 21
<212> TYPE: RNA
<213> ORGANISM: Artificial Sequence
<220> FEATURE:
<223> OTHER INFORMATION: siRNA

<400> SEQUENCE: 2
ugccuuggaa guggagaaau u                                              21

<210> SEQ ID NO 3
<211> LENGTH: 21
<212> TYPE: RNA
<213> ORGANISM: Artificial Sequence
<220> FEATURE:
<223> OTHER INFORMATION: siRNA

<400> SEQUENCE: 3
gcugggauac caauacaucu u                                              21

<210> SEQ ID NO 4
<211> LENGTH: 21
<212> TYPE: RNA
<213> ORGANISM: Artificial Sequence
<220> FEATURE:
<223> OTHER INFORMATION: siRNA

<400> SEQUENCE: 4
```

```
gccuuggaag uggagaaaau u                                              21

<210> SEQ ID NO 5
<211> LENGTH: 21
<212> TYPE: RNA
<213> ORGANISM: Artificial Sequence
<220> FEATURE:
<223> OTHER INFORMATION: siRNA

<400> SEQUENCE: 5
agcugggaua ccaauacauu u                                              21

<210> SEQ ID NO 6
<211> LENGTH: 21
<212> TYPE: RNA
<213> ORGANISM: Artificial Sequence
<220> FEATURE:
<223> OTHER INFORMATION: siRNA

<400> SEQUENCE: 6
gagcagauca auaggcgaau u                                              21

<210> SEQ ID NO 7
<211> LENGTH: 21
<212> TYPE: RNA
<213> ORGANISM: Artificial Sequence
<220> FEATURE:
<223> OTHER INFORMATION: siRNA

<400> SEQUENCE: 7
guagaaaugu caaucagagu u                                              21

<210> SEQ ID NO 8
<211> LENGTH: 21
<212> TYPE: RNA
<213> ORGANISM: Artificial Sequence
<220> FEATURE:
<223> OTHER INFORMATION: siRNA

<400> SEQUENCE: 8
ccguagaaau gucaaucagu u                                              21

<210> SEQ ID NO 9
<211> LENGTH: 21
<212> TYPE: RNA
<213> ORGANISM: Artificial Sequence
<220> FEATURE:
<223> OTHER INFORMATION: siRNA

<400> SEQUENCE: 9
agugaaaacu agaggagggu u                                              21

<210> SEQ ID NO 10
<211> LENGTH: 21
<212> TYPE: RNA
<213> ORGANISM: Artificial Sequence
<220> FEATURE:
<223> OTHER INFORMATION: siRNA

<400> SEQUENCE: 10
ggagugaaaa cuagaggagu u                                              21

<210> SEQ ID NO 11
<211> LENGTH: 21
<212> TYPE: RNA
```

<213> ORGANISM: Artificial Sequence
<220> FEATURE:
<223> OTHER INFORMATION: siRNA

<400> SEQUENCE: 11
cccguagaaa ugucaaucau u                                              21

<210> SEQ ID NO 12
<211> LENGTH: 21
<212> TYPE: RNA
<213> ORGANISM: Artificial Sequence
<220> FEATURE:
<223> OTHER INFORMATION: siRNA

<400> SEQUENCE: 12
uagaaauguc aaucagagcu u                                              21

<210> SEQ ID NO 13
<211> LENGTH: 21
<212> TYPE: RNA
<213> ORGANISM: Artificial Sequence
<220> FEATURE:
<223> OTHER INFORMATION: siRNA

<400> SEQUENCE: 13
gggagugaaa acuagaggau u                                              21

<210> SEQ ID NO 14
<211> LENGTH: 21
<212> TYPE: RNA
<213> ORGANISM: Artificial Sequence
<220> FEATURE:
<223> OTHER INFORMATION: siRNA

<400> SEQUENCE: 14
aaaacuagag gagggcgaau u                                              21

<210> SEQ ID NO 15
<211> LENGTH: 21
<212> TYPE: RNA
<213> ORGANISM: Artificial Sequence
<220> FEATURE:
<223> OTHER INFORMATION: siRNA

<400> SEQUENCE: 15
gaaucuccgc caaucuguuu u                                              21

<210> SEQ ID NO 16

<400> SEQUENCE: 16

000

<210> SEQ ID NO 17
<211> LENGTH: 21
<212> TYPE: RNA
<213> ORGANISM: Artificial Sequence
<220> FEATURE:
<223> OTHER INFORMATION: siRNA

<400> SEQUENCE: 17
gccccguaga aaugucaauu u                                              21

<210> SEQ ID NO 18
<211> LENGTH: 21
<212> TYPE: RNA

```
<213> ORGANISM: Artificial Sequence
<220> FEATURE:
<223> OTHER INFORMATION: siRNA

<400> SEQUENCE: 18
agaaauguca aucagagccu u                                              21

<210> SEQ ID NO 19
<211> LENGTH: 21
<212> TYPE: RNA
<213> ORGANISM: Artificial Sequence
<220> FEATURE:
<223> OTHER INFORMATION: siRNA

<400> SEQUENCE: 19
aagcccaaac uggucuuuu u                                               21

<210> SEQ ID NO 20
<211> LENGTH: 21
<212> TYPE: RNA
<213> ORGANISM: Artificial Sequence
<220> FEATURE:
<223> OTHER INFORMATION: siRNA

<400> SEQUENCE: 20
agcccaaacu guggucuuuu u                                              21

<210> SEQ ID NO 21
<211> LENGTH: 21
<212> TYPE: RNA
<213> ORGANISM: Artificial Sequence
<220> FEATURE:
<223> OTHER INFORMATION: siRNA

<400> SEQUENCE: 21
aaacuguggu cuuuggcagu u                                              21

<210> SEQ ID NO 22
<211> LENGTH: 21
<212> TYPE: RNA
<213> ORGANISM: Artificial Sequence
<220> FEATURE:
<223> OTHER INFORMATION: siRNA

<400> SEQUENCE: 22
aacugugguc uuuggcagau u                                              21

<210> SEQ ID NO 23
<211> LENGTH: 21
<212> TYPE: RNA
<213> ORGANISM: Artificial Sequence
<220> FEATURE:
<223> OTHER INFORMATION: siRNA

<400> SEQUENCE: 23
aagcccaaac uggucuuuu u                                               21

<210> SEQ ID NO 24
<211> LENGTH: 21
<212> TYPE: RNA
<213> ORGANISM: Artificial Sequence
<220> FEATURE:
<223> OTHER INFORMATION: siRNA

<400> SEQUENCE: 24
agcccaaacu guggucuuuu u                                              21
```

<210> SEQ ID NO 25
<211> LENGTH: 21
<212> TYPE: RNA
<213> ORGANISM: Artificial Sequence
<220> FEATURE:
<223> OTHER INFORMATION: siRNA

<400> SEQUENCE: 25
aaacuguggu cuuuggcagu u                                           21

<210> SEQ ID NO 26
<211> LENGTH: 21
<212> TYPE: RNA
<213> ORGANISM: Artificial Sequence
<220> FEATURE:
<223> OTHER INFORMATION: siRNA

<400> SEQUENCE: 26
aacugugguc uuuggcagau u                                           21

<210> SEQ ID NO 27
<211> LENGTH: 25
<212> TYPE: DNA
<213> ORGANISM: Artificial Sequence
<220> FEATURE:
<223> OTHER INFORMATION: primer used to generate sgRNA to rs1421085

<400> SEQUENCE: 27
caccgctgga aggaacgcgt ttgtt                                       25

<210> SEQ ID NO 28
<211> LENGTH: 25
<212> TYPE: DNA
<213> ORGANISM: Artificial Sequence
<220> FEATURE:
<223> OTHER INFORMATION: primer used to generate sgRNA to rs1421085

<400> SEQUENCE: 28
caccgggaca gtgcgtagac taaac                                       25

<210> SEQ ID NO 29
<211> LENGTH: 21
<212> TYPE: DNA
<213> ORGANISM: Artificial Sequence
<220> FEATURE:
<223> OTHER INFORMATION: forward PCR primer

<400> SEQUENCE: 29
aaagtcgctc tgagttgtta t                                           21

<210> SEQ ID NO 30
<211> LENGTH: 21
<212> TYPE: DNA
<213> ORGANISM: Artificial Sequence
<220> FEATURE:
<223> OTHER INFORMATION: reverse PCR primer

<400> SEQUENCE: 30
ggagcgggag aaatggatat g                                           21

<210> SEQ ID NO 31
<211> LENGTH: 21
<212> TYPE: DNA
<213> ORGANISM: Artificial Sequence
<220> FEATURE:

<223> OTHER INFORMATION: reverse PCR primer

<400> SEQUENCE: 31
gcgaagagtt tgtcctcaac c                                    21

<210> SEQ ID NO 32
<211> LENGTH: 20
<212> TYPE: DNA
<213> ORGANISM: Artificial Sequence
<220> FEATURE:
<223> OTHER INFORMATION: forward PCR primer

<400> SEQUENCE: 32
atccgaaaag aaaacgttga                                      20

<210> SEQ ID NO 33
<211> LENGTH: 20
<212> TYPE: DNA
<213> ORGANISM: Artificial Sequence
<220> FEATURE:
<223> OTHER INFORMATION: reverse PCR primer

<400> SEQUENCE: 33
atccaggtta cggatatagt                                      20

<210> SEQ ID NO 34
<211> LENGTH: 25
<212> TYPE: DNA
<213> ORGANISM: Artificial Sequence
<220> FEATURE:
<223> OTHER INFORMATION: forward and reverse mutagenesis primer

<400> SEQUENCE: 34
taaggcatga cattgattaa gtgtc                                25

<210> SEQ ID NO 35
<211> LENGTH: 21
<212> TYPE: RNA
<213> ORGANISM: Artificial Sequence
<220> FEATURE:
<223> OTHER INFORMATION: siRNA

<400> SEQUENCE: 35
aggagaagaa gauaagcccu u                                    21

<210> SEQ ID NO 36
<211> LENGTH: 21
<212> TYPE: RNA
<213> ORGANISM: Artificial Sequence
<220> FEATURE:
<223> OTHER INFORMATION: siRNA

<400> SEQUENCE: 36
cuauguuuca agcugcucau u                                    21

<210> SEQ ID NO 37
<211> LENGTH: 21
<212> TYPE: RNA
<213> ORGANISM: Artificial Sequence
<220> FEATURE:
<223> OTHER INFORMATION: siRNA

<400> SEQUENCE: 37
aaggagaaga agauaagccu u                                    21

```
<210> SEQ ID NO 38
<211> LENGTH: 21
<212> TYPE: RNA
<213> ORGANISM: Artificial Sequence
<220> FEATURE:
<223> OTHER INFORMATION: siRNA

<400> SEQUENCE: 38
accuuuggac uauguuucau u                                              21

<210> SEQ ID NO 39
<211> LENGTH: 21
<212> TYPE: RNA
<213> ORGANISM: Artificial Sequence
<220> FEATURE:
<223> OTHER INFORMATION: siRNA

<400> SEQUENCE: 39
gauuacauug ccaacugcau u                                              21

<210> SEQ ID NO 40
<211> LENGTH: 21
<212> TYPE: RNA
<213> ORGANISM: Artificial Sequence
<220> FEATURE:
<223> OTHER INFORMATION: siRNA

<400> SEQUENCE: 40
ggcacuuuau aaauacaugu u                                              21

<210> SEQ ID NO 41
<211> LENGTH: 21
<212> TYPE: RNA
<213> ORGANISM: Artificial Sequence
<220> FEATURE:
<223> OTHER INFORMATION: siRNA

<400> SEQUENCE: 41
gauuaaccuu uggacuaugu u                                              21

<210> SEQ ID NO 42
<211> LENGTH: 21
<212> TYPE: RNA
<213> ORGANISM: Artificial Sequence
<220> FEATURE:
<223> OTHER INFORMATION: siRNA

<400> SEQUENCE: 42
auuaaccuuu ggacuauguu u                                              21

<210> SEQ ID NO 43
<211> LENGTH: 21
<212> TYPE: RNA
<213> ORGANISM: Artificial Sequence
<220> FEATURE:
<223> OTHER INFORMATION: siRNA

<400> SEQUENCE: 43
uaugaaacaa uaacagcccu u                                              21

<210> SEQ ID NO 44
<211> LENGTH: 21
<212> TYPE: RNA
<213> ORGANISM: Artificial Sequence
<220> FEATURE:
<223> OTHER INFORMATION: siRNA
```

<400> SEQUENCE: 44
uauguuucaa gcugcucaau u                                              21

<210> SEQ ID NO 45
<211> LENGTH: 158
<212> TYPE: DNA
<213> ORGANISM: Homo sapiens

<400> SEQUENCE: 45
ttgtaaggaa caagataatc tcattgttcc tcctgctact taaaataaag gtaatattga    60
ttttatagta gcagttcagg tcctaaggca tgatattgat taagtgtctg atgagaattt   120
gtagggtagt ctcccagacc tgcagctaca gggcatct                           158

<210> SEQ ID NO 46
<211> LENGTH: 158
<212> TYPE: DNA
<213> ORGANISM: Macaca mulatta

<400> SEQUENCE: 46
ttgtaaggaa caagataatc tcattgttcc tcctgctact taaaataaag gtaatattga    60
ttttatagta gcagttcagg tcctaaggca tgatattgat taagtgtctg atgagaattt   120
gtagggtagc ctcccagacc tgcagctaca gggcatct                           158

<210> SEQ ID NO 47
<211> LENGTH: 158
<212> TYPE: DNA
<213> ORGANISM: Pan troglodytes

<400> SEQUENCE: 47
ttgtaaggaa caagataatc tcattgttcc tcctgctact taaaataaag gtaatattga    60
ttttatagta gcagttcagg tcctaaggca tgatattgat taagtgtctg atgagaattt   120
gtagggtagt ctcccagacc tgcagctaca gggcatct                           158

<210> SEQ ID NO 48
<211> LENGTH: 157
<212> TYPE: DNA
<213> ORGANISM: Mus musculus

<400> SEQUENCE: 48
ttgtaagcaa caagataatc tcattgttcc tcctgctact taaaataaag gtaatattga    60
ttttacggta gcagttcgag tcctaaggca tcgtattgat taagcgtcta gtgagaattt   120
gtagggcagc cttctgagct gcagccacag ggcatct                            157

<210> SEQ ID NO 49
<211> LENGTH: 157
<212> TYPE: DNA
<213> ORGANISM: Oryctol cuniculus

<400> SEQUENCE: 49
ttgtaaggaa caagataatc tcattgttcc tcctgttact taaaataaag gcaatattga    60
ttgtatcata gcagttcagg tcctaaggca tggtattgat taagcgtctg atgagaattt   120
gtggggtagc cttctagact acagccacag ggcatct                            157

<210> SEQ ID NO 50
<211> LENGTH: 157
<212> TYPE: DNA
<213> ORGANISM: Rattus norvegicus

```
<400> SEQUENCE: 50
ttgtaagcaa caagataatc tcattgttcc tcctgctact taaaataaag gtaatattga        60
ttttacggta gcagttcgag tcctaaggca tcgtattgat taagcgtcta gtgagaattt       120
gtagggcagc cttctgagct acagccacag ggcatct                               157

<210> SEQ ID NO 51
<211> LENGTH: 158
<212> TYPE: DNA
<213> ORGANISM: Equus caballus

<400> SEQUENCE: 51
ttgtaaggaa caagataatc tcattgttct tcctgctact taaaataaag gtaatattga        60
ttttatagta gcagttcagg tcctaaggca tgatattgat taagcgtctg atgagaattt       120
gcagggtagc cttctagacc tacagctaca gggcatct                              158

<210> SEQ ID NO 52
<211> LENGTH: 158
<212> TYPE: DNA
<213> ORGANISM: Canis familiaris

<400> SEQUENCE: 52
ttgtaaggaa caagataatc tcattgttcc tcctgctact taaaataaag gtaatattga        60
ttttatagta gcagttcagg tcctaaggca tgatattgat taagcgtctg tcgagaattt       120
gcagggtagc cttctaggcc tacagctaca gggcatcc                              158

<210> SEQ ID NO 53
<211> LENGTH: 158
<212> TYPE: DNA
<213> ORGANISM: Bos taurus

<400> SEQUENCE: 53
ttgtaaggaa caagataatc tcactgttcc tcctgctact taaaataaag gtaatattga        60
ttttagagta gcagttcagg tcctaaggcg tgatattgat caggcatctg atgagaattt       120
gcagggtagg cttccagccc tgcagctaca gggcatct                              158

<210> SEQ ID NO 54
<211> LENGTH: 158
<212> TYPE: DNA
<213> ORGANISM: Monodelphis domesticus

<400> SEQUENCE: 54
ttgtaaggaa caagataatc tcattgttcc tcatgctact taaaatagag gcaatattga        60
ttttatagta gcagttcagg tcctaaggca tgatattgat taagcgtctg atgagaattt       120
gcagggtagt cttccagatc tgcagctaca aggcgtct                              158
```

COMPOSITIONS AND METHODS FOR MANIPULATION OF ADIPOCYTE ENERGY CONSUMPTION REGULATORY PATHWAY

RELATED APPLICATION(S)

This application is the U.S. National Stage of International Application No. PCT/US2015/000311, filed Dec. 23, 2015, which designates the U.S., published in English, and claims the benefit of U.S. Provisional Application No. 62/096,737, filed Dec. 24, 2014, U.S. Provisional Application No. 62/206,841, filed on Aug. 18, 2015, and U.S. Provisional Application No. 62/207,365, filed on Aug. 19, 2015. The entire teachings of the above applications are incorporated herein by reference.

GOVERNMENT SUPPORT

This invention was made with Government support under Grant No. RO1 HG004037 awarded by the National Institutes of Science. The Government has certain rights in the invention.

INCORPORATION BY REFERENCE OF MATERIAL IN ASCII TEXT FILE

This application incorporates by reference the Sequence Listing contained in the following ASCII text file:
a) File name: 00502276003_Updated_Seq_Listing.txt; created Nov. 21, 2018, 11 KB in size.

BACKGROUND OF THE INVENTION

Despite the growing number of genome-wide association studies (GWAS), genetic signals have rarely been traced to the causal genetic variant explaining the mechanistic basis of the observed association. This is particularly challenging for non-coding variants, which constitute 93% of top-scoring GWAS single-nucleotide variants (SNVs), given still incomplete regulatory annotations, and uncertainty of the relevant cell types, target genes, or upstream regulators. The challenge is even greater for complex traits such as obesity or disorders such as cancer and associated disorders, that involve multiple organs, hormonally- and neuronally-regulated signals, strong environmental effects, and pleiotropic interactions with other complex traits.

Obesity affects more than 500 million people worldwide and is one of the leading contributors to common and severe disorders, including type 2 diabetes, cardiovascular disorders, and cancer (Guh, D. P. et al., BMC Public Health 9, 88 (2009); Adams, K. F. et al. N Engl J Med 355, 763-778 (2006); Wang, Y., Adv Nutr 2, 23-31 (2011)). Thus, considerable efforts have been made to define its causal mechanisms, as understanding the genetic cause of obesity could illuminate the causal genetic mechanism of other disorders. For example, the fatso/fat mass and obesity associated (FTO) locus has been shown to possess the strongest association with obesity risk (Frayling, T. M. et al., Science 316: 889-894 (2007); Dina, C. et al., Nat Genet 39, 724-726 (2007); Tan, L. J. et al. PLoS One 9, e96149 (2014)). Despite considerable efforts to define causal mechanisms, the functional variant remains uncharacterized among 82 highly-associated SNVs, and the molecular and cellular intermediate phenotypes, mechanisms, and biological processes leading to obesity remain unknown.

SUMMARY OF THE INVENTION

The present invention provides, in part, a method for modulating energy consumption pathways in adipocytes to increase or decrease energy consumption, as needed, for the treatment of a disorder mediated by the energy consumption pathway. In particular, provided herein is the regulatory circuitry and mechanistic basis of the FTO obesity-associated locus and the causal variant that recapitulates the molecular and cellular signatures of obesity. As described herein, the T-to-C single-nucleotide variant rs1421085 of the FTO locus disrupts a conserved motif for the repressor ARID5B in risk allele carriers, resulting in activation of a potent mesenchymal adipocyte progenitor enhancer in the FTO locus. This results in an increased expression of IRX3 and IRX5 in primary adipocyte progenitors, leading to a developmental lineage shift from beige/brite to white adipocyte expression programs, thereby shutting off mitochondrial thermogenesis. The result is lipid accumulation in all major fat stores. Thus, the present invention provides a method for manipulating the regulatory circuitry described herein, to reverse the obesity phenotype, or stimulate the obesity phenotype, in a cell-autonomous way, by modulating any one or more of the components of the energy consumption (e.g., thermogenesis) pathway described herein.

Accordingly, in one aspect, the present invention provides a method of modulating energy consumption (e.g., thermogenesis) in an adipocyte, comprising contacting the adipocyte with an effective amount of one or more agents that modulate one or more of iroquois homeobox protein 3 (IRX3) function, iroquois homeobox protein 5 (IRX5) function, AT-rich interactive domain-containing protein 5B (ARID5B) function, obesity browning enhancer 1 (OBE1) function, or genetic variant rs1421085 function.

In a related aspect, the present invention provides a method of treating a disorder in a patient in need thereof, comprising administering an effective amount of one or more agents that modulate one or more of IRX3 function, IRX5 function, ARID5B function, OBE1, or genetic variant rs1421085 function, wherein the disorder is mediated by a dysregulation of energy consumption (e.g., thermogenesis) in an adipocyte.

The present invention also provides a pharmaceutical composition comprising an effective amount of one or more agents that modulate one or more of IRX3 function, IRX5 function, ARID5B function, OBE1 function, or genetic variant rs1421085 function in an adipocyte.

A method of modulating energy consumption (e.g., thermogenesis) in a cell, comprising contacting the cell with an effective amount of a genome editing system that modifies genetic variant rs1421085.

In further aspects, the present invention provides a method for identifying and selecting a subject with increased risk of developing a disorder mediated by a dysregulation of the energy consumption (e.g., thermogenesis) pathway, comprising the steps of: (a) sequencing at least part of a genome comprising one or more genes selected from the group consisting of ARID5B, rs1421085, OBE1, IRX3 and IRX5 or a downstream target thereof, in a cell, and (b) identifying from said sequencing one or more alleles in one or more genes selected from the group consisting of ARID5B, rs1421085, OBE1, IRX3 and IRX5 or a downstream target thereof, wherein presence of one or more risk alleles indicates an increased risk of developing a disorder mediated by a dysregulation of the energy consumption (e.g., thermogenesis) pathway.

In another aspect, the present invention provides a method of identifying a patient with increased risk of developing a disorder associated with dysregulation of energy consumption in an adipocyte, the method comprising: a) sequence or genotyping at least part of a genome comprising IRX3, IRX5, ARID5B, OBE1, genetic variant rs1421085, or a combination thereof, in a sample from the patient; and b) identifying from said sequence or genotyping one or more mutations in at least part of a genome comprising IRX3, IRX5, ARID5B, OBE1, genetic variant rs1421085, or a combination thereof; wherein the presence of one or more mutation indicates that the patient has an increased risk of developing a disorder associated with dysregulation of energy consumption in an adipocyte.

In further aspects, the present invention also provides a method of identifying a patient with increased risk of developing a disorder associated with dysregulation of energy consumption in an adipocyte, the method comprising: a) measuring an expression level of IRX3, IRX5, or ARID5B, or a combination thereof, in a sample from the patient; and b) comparing the expression level measured in step a) with a control level of IRX3, IRX5, or ARID5B, or a combination thereof; wherein an increase or decrease in the measured level as compared to the control level indicates that the patient has an increased risk of developing a disorder associated with dysregulation of energy consumption in an adipocyte.

The present invention uncovers therapeutic targets for cell-autonomous (e.g., adipocyte-autonomous) pharmacological treatment for anti-cachexia and anti-obesity effects. As demonstrated herein at the molecular, cellular, and organismal levels, IRX3 and IRX5-mediated loss of mitochondrial thermogenic activity lies at the heart of the effect of the FTO genetic locus on obesity risk.

BRIEF DESCRIPTION OF THE DRAWINGS

The foregoing will be apparent from the following more particular description of example embodiments of the invention, as illustrated in the accompanying drawings.

FIG. 1A shows the genetic association with body mass index (BMI) for all common FTO locus variants, including reported SNV rs1558902 (purple diamond) and causal rs1421085 (red square). FIG. 1B shows chromatin state annotations for the locus across 127 reference epigenomes. FIG. 1C shows human Simpson-Golabi-Behmel Syndrome (SGBS) adipocyte enhancer activity for 10 kb tiles of risk (red shown at right) and non-risk (blue shown at left) haplotypes using relative luciferase expression (n=7). FIG. 1D shows linkage disequilibrium (LD) with rs1558902 in larger 2.5 Mb window. FIG. 1E shows chromatin conformation capture (Hi-C) interactions contact probabilities (blue) in human IMR90 myofibroblasts revealing a 2 Mb Topologically Associating Domain, and LD mean $r^2$ statistics (red) for all SNV pairs at 40 kb-resolution. FIG. 1F shows expression levels in human adipose progenitors after 2 days of differentiation isolated from homozygous risk (red shown at right n=20) and nonrisk (blue shown at left, n=18) participants using quantitative PCR for all genes in 2.5 Mb locus.

FIG. 2A shows mitochondrial and FXR/RXR genes with strongest positive (red) or negative (green) correlation with IRX3 and IRX5 in human perirenal adipose tissue (n=10). FIGS. 2B and 2C show increased adipocyte diameter and decreased mitochondrial DNA content for risk allele participants (red, n=16 and n=8, respectively) relative to non-risk allele participants (red, n=26 and n=8, respectively) in isolated differentiated adipocytes. FIG. 2D shows altered basal and isoproterenol-stimulated oxygen consumption rate (OCR) upon siRNA knock-down and overexpression of IRX3 and IRX5 in risk (n=8) and non-risk (n=10) allele participants. siRNA efficiency 62% for IRX3 and 71% for IRX5.

FIG. 3A shows disruption of an ARID5B repressor motif in the evolutionarily-conserved motif module surrounding rs1421085 (SEQ ID NOS: 45-54, in order of appearance). FIG. 3B shows Phylogenetic Module Complexity Analysis (PMCA) scores in FTO region for all 82 non-coding SNVs in LD ($r^2 \geq 0.8$) with the GWAS-reported tag SNV rs1558902, with maximal score for rs1421085. FIG. 3C shows increased endogenous expression of IRX3 and IRX5 upon single-nucleotide T-to-C editing of rs1421085 in the non-risk (blue) haplotype of a non-risk participant using CRISPR/Cas9 (n=5 clonal expansions). CRISPR/Cas9 re-editing from the engineered C risk allele (red) back into a T protective allele (green) using an alternative sgRNA restores low endogenous IRX3 and IRX5 gene expression. FIG. 3D shows reduced expression of IRX3 and IRX5 upon C-to-T editing (green) of the risk allele (red) from a homozygous risk patient in adipocyte progenitors. Knock-down of ARID5B increases IRX3 and IRX5 levels only in the rescued (green) allele, but not in the risk allele (red).

FIG. 4A shows increased expression for IRX3 and IRX5 during early adipocyte differentiation specifically for the risk allele, which is rescued by C-to-T genome editing. FIG. 4B shows increased expression for thermogenic and mitochondrial genes upon C-to-T endogenous single nucleotide editing of rs1421085 in adipocyte progenitors from a risk allele patient. FIG. 4C shows increased basal and isoproterenol-stimulated OCR upon C-to-T single-nucleotide endogenous rescue of rs1421085 in adipocytes from a risk allele patient. FIG. 4D shows a summary of the mechanistic model of the FTO locus association with obesity, demonstrating a developmental shift favoring lipid-storing white adipocytes over energy-burning beige adipocytes. As shown, a single-nucleotide T-to-C variant, rs1421085, disrupts a conserved ARID5B repressor motif, activates a mesenchymal enhancer and its targets IRX3 and IRX5, which leads to reduced heat dissipation by mitochondrial thermogenesis and increased lipid storage in white adipocytes.

FIG. 5A shows 25-state chromatin state model using 12 imputed epigenomic marks learned jointly across 127 reference epigenomes. For each state (rows) are shown: the state abbreviation; the frequency with which each mark is expected in each state (emission parameters) the genome coverage and functional enrichments for diverse annotations and conserved elements; the median observed and imputed DNA methylation and RNA-Seq signal; and a short description. FIG. 5B shows lineage relationships of mesenchymal stem cells (MSCs) and MSC-derived lineages, including brown, white, and brite/beige adipocytes involved in lipid storage and energy dissipation. Epigenome identity (EID) numbers correspond to Roadmap Epigenomics (Kundaje, A. et al., Nature 518:317-30, 2015) numbering of reference epigenomes. E114-E129 correspond to ENCODE project (Nature 489:57-74, 2012) reference epigenomes. Cell graphics modified with permission by Bio-Techne. FIG. 5C shows that tissues and cell types with the longest enhancer lengths in the FTO locus include multiple mesenchymal-derived lineages, e.g., adipose-derived mesenchymal cells (12.8 kb, E025), muscle progenitor cells (7 kb, E052), and osteoblasts (1 kb, E129). The enhancer active in adipose-derived mesenchymal cells is 15.2-fold longer than the median enhancer length (800 bp, dashed red line). FIG. 5D displays the result of allelic enhancer assays for Segment 1 across five cell types, including both BMI-relevant cell types and control cell types, measured by relative luciferase expression. Non-risk haplotype (blue, lower bars) and risk rs1421085 allele (red, upper bars) introduced as a single nucleotide alteration on the nonrisk haplotype were tested for segment 1, by transfection in SGBS adipocytes, HT22 neuronal cells, C2C12 muscle cells, Huh7 hepatocytes and K562 lymphoma cells. Enhancer activity was measured by relative luciferase expression and normalized to the mean ratio from pGL4.22-TK promoter construct. Risk allelic enhancer activity was specifically observed in human SGBS adipocytes (n=7). P-values: t-test, Error bars: SD.

FIGS. 6A-6G. Allele-dependent association of IRX3 and IRX5 with lipid storage and mitochondrial function genes in human adipose cells. FIG. 6A shows risk (n=13) and non-risk (n=13) homozygous participant mRNA expression for IRX3 and IRX5 measured using qPCR (normalized to HPRT) in adipose mesenchymal cells (left, as in FIG. 1F) cultured, induced to differentiate, and harvested after 2 days, and for whole adipose tissue (right), demonstrating lack of eQTLs in whole-adipose tissue and the importance of adipocyte-specific measurements. FIG. 6B shows reduced expression of IRX3 and IRX5 in perithyroid brown adipose tissue (BAT) vs. subcutaneous white adipose tissue (scWAT) for healthy persons, measured by Affymetrix microarrays (n=9) (IRX3 probe set 229638_at, IRX5 probe set 210239_at), consistent with repression of energy consumption in white WAT. P-values: t-test, Error bars: SEM. FIG. 6C shows negative correlation between IRX3 (Affymetrix microarray probe set 8001449) and IRX5 (probe set 7995668) mRNA levels and both mitochondrial biogenesis marker PGC1A (probe set 8099633), and uncoupling protein UCP1 (probe set 8102904) in human perirenal white subcutaneous adipose tissue containing brown adipocytes, obtained from healthy kidney donors (n=10). FIG. 6D shows reduced risk allele expression of gene markers for mitochondrial function (green), catabolic lipid metabolism (blue), and adipocyte differentiation (orange), and increased risk-allele expression of gene markers for anabolic lipid metabolism (red), measured using qPCR in primary adipose cells isolated from participants homozygous for the non-risk (n=18) and risk allele (n=20). Risk allele carriers show reduced adipocyte differentiation marker PPARG2 (orange), indicating reduced adipocyte turnover. IRX3 and IRX5 (black) are also shown as reference. FIG. 6E shows the fold change (Fold) and significance (Pval) of expression changes for the 20 genes that are most positively (n=10) and negatively (n=10) correlated with inter-individual expression of IRX3 and IRX5 (FIG. 2A) for three settings: the risk allele-dependent gene expression in isolated adipocyte progenitors (as shown in FIG. 1F for IRX3 and IRX5); upon ARID5B knock-down (as shown in FIG. 11H for IRX3 and IRX5); and after T-to-C allele editing by CRISRP/Cas9 (as shown in FIG. 4A for IRX3 and IRX5). Correlation coefficients are Spearman's rho (n=10 perirenal white adipose tissue containing brown adipocytes from FIG. 2A). p-values were calculated by Mann Whitney U test. FIG. 6F shows reduced UCP1 gene expression from risk allele patients (n=8) compared to non-risk allele participants (n=8) for baseline, cold exposure (incubation at 30° C. for 6 hours) and isoprotereno1-mediated β3-adrenergic receptor activation (1 µmol/l, 12 hours) indicative of thermogenic response in adipocytes. FIG. 6G shows reduced basal and isoproterenol-stimulated (coupled and uncoupled) respiration (oxygen consumption rate, OCR) in isolated adipocyte progenitor cells from risk (n=26) vs. non-risk (n=20) homozygous participants after 2 days after differentiation, revealing disrupted mitochondrial function and thermogenesis response.

FIG. 7A shows rescue of UCP1 gene expression levels upon knock-down of IRX3 or IRX5 in risk-allele carriers (n=10), restoring protective-allele UCP1 expression levels, but no change in UCP1 expression for IRX3 or IRX5 knock-down in protective-allele participants (n=8). The cells were induced to differentiate concomitant with siRNA treatment and collected after two days. FIG. 7B shows reduced expression of mitochondrial activity marker genes upon doxycycline-induced overexpression of IRX3 and IRX5 in adipocyte progenitors specifically in non-risk (n=8) vs. risk (n=10) participants. FIG. 7C shows reduced UCP1 expression upon IRX3 or IRX5 overexpression in differentiating primary human adipocyte progenitor cells from protective-allele (n=8) participants, resulting in risk allele participant UCP1 levels, but no change in UCP1 expression upon IRX3 or IRX5 overexpression in risk-allele participants (n=10). The cells were induced to differentiate concomitant with Doxycycline and collected after two days. Target gene expression measured by qPCR was normalized to HPRT mRNA.

FIGS. 8A-8R. Anti-obesity phenotypes in Adipo-Irx3DN transgenic mice. All panels show phenotypic consequences of an adipocyte-specific repression of Irx3 by expression of a dominant-negative form of Irx3 in adipose cells (green; aP2-Cre; Irx3EnR), compared to littermate controls (grey; EnR). FIGS. 8A and 8B show reduced body weight for ap2-Irx3DN mice, and reduced body weight gain on a high-fat diet (n=11 normal diet, n=10 highfat) vs. controls (n=12 normal diet, n=6 high-fat diet). FIG. 8C shows reduced total fat mass as a percentage of total body mass in aP2-Irx3DN mice vs. controls (white and brown adipose tissue combined). FIG. 8D shows reduced adipose tissue weight for major fat stores for aP2-Irx3DN mice vs. controls, but no difference in liver. FIG. 8O show distribution and average of cross-sectioned area of subcutaneous white adipocytes, revealing reduced white adipocyte size for aP2-Irx3DN compared to control mice. FIG. 8P shows 57% reduced fat-mass ratio vs. control for aP2-Irx3DN mice vs. 25% reduction for Irx3 knock-out mice, and 19% for Ins2-Irx3DN. FIG. 8Q confirms robust expression of aP2-Irx3DN adipose-specific dominant negative Irx3-EnR transgene in all measured adipose tissues, and robust expression of Ins2-Irx3DN hypothalamus-specific dominant negative Irx3-EnrR transgene in Hypothalamus, but no significant expression in the wrong tissues, indicating that the phenotypes we observe for aP2-Irx3DN are not due to ectopic expression in hypothalamus. FIG. 8R shows unchanged endogenous Fto mRNA level in aP2-Irx3DN vs. controls in adipose tissues, indicating that Fto itself had no role in the anti-obesity phenotype. Sc=subcutaneous/inguinal. Vc=Visceral. WAT=White Adipose Tissue. BAT=interscapular brown adipose tissue.

FIG. 9A shows decreased lipid accumulation in cultured mouse embryonic fibroblasts (MEFs) from Irx3/5 double knock-out (DKO) mice, measured by Oil Red 0 lipid staining after 8 days of in vitro adipocyte differentiation, indicating cell-autonomous regulation of obesity-related phenotypes. FIG. 9B shows reduced expression of the lipid carrier gene aP2/Fabp4, a marker of lipid stores, but increased expression of adipocyte differentiation markers Pparg and Cepbalpha in Irx3/5 DKO MEFs. FIGS. 9C and 9D show that overexpression of Irx3 or Irx5 in 3T3-L1 cells leads to increased lipid accumulation visualized by Oil-Red-O lipid staining (FIG. 9C) and increased mRNA expression of Fabp4 (FIG. 9D). The images are representative of phase-contrast microscopic views of the 3T3-L1 adipocytes on day 4 post-differentiation, and Oil-Red-O lipid staining on day 8 post-differentiation. Irx3 overexpression did not influence Irx5 levels, and Irx5 overexpression did not influence Irx3 levels, indicating that the two act in parallel without cross-regulation or feedback. FIG. 9E shows that IRX3 and IRX5 overexpression leads to reduced UCP1 expression, measured in a luciferase assay using a reporter construct containing the human UCP1 promoter fused to the luciferase gene. The reporter was co-transfected in ME3 beige preadipocytes with plasmid encoding human IRX3 or IRX5 (0.1, 0.5 or 1.0 μg). Repression is seen for both basal (grey, no isoproterenol and 9-cis retinoic acid) and stimulated (orange, isoproterenol and 9-cis retinoic acid), with a significantly more pronounced repression upon stimulation, consistent with reduced energy consumption. n=3. Error bars: SEM.

FIG. 10A shows a multiple sequence alignment of the 1 kb region surrounding the evolutionarily-conserved motif module disrupted by the predicted causal variant rs1421085 (SEQ ID NOS: 45-54, in order of appearance). FIG. 1GB shows the Phylogenetic Complexity Module Analysis (PMCA) scores for all single nucleotide variants (SNVs) in the FTO obesity locus, revealing rs1421085 as the top-scoring SNV for all tested parameters. TFBS=transcription factor binding sites. FIG. 10C shows increased enhancer activity upon transfection into human SGBS preadipocytes (n=9) for 10 kb and 1 kb segments centered at rs1421085 upon introduction of the rs1421085 risk variant (red) on the non-risk haplotype (blue), but no change for 100 bp. FIG. 10D shows orientation- and position-independent gain of enhancer activity for the 1 kb region centered on rs1421085, upon T-to-C single-nucleotide editing of the non-risk allele in a luciferase enhancer reporter assay fused to a basal pGL4.22-TK promoter in SGBS adipocytes (n=9). FIG. 10E shows increased binding for the non-risk T allele (intact ARIDSB motif) vs. the risk C allele (disrupted ARIDSB motif) using electrophoretic mobility shift assays (EMSA) using human adipocytic nuclear extract. Binding in the T allele is competed away by increasing amounts of canonical ARID5B motif (AATAT) unlabeled competing probe. The C allele shows no binding (no shifted probe band) even without unlabeled probe competition. FIG. 10F shows whole tissue and adipose stromal cell expression for ARIDSB, LHX6, NKX6-3 and other ARID family members based on Illumina microarrays for lean (n=13) and obese (n=17) participants. FIG. 10G shows inverse correlation between ARIDSB and IRX3/IRX5 expression using HPRT-normalized qPCR in adipocyte progenitors specifically from non-risk participants (n=18), but no correlation for risk participants (n=20). FIG. 10H shows increased IRX3 and IRX5 levels upon siRNA knock-down of ARIDSB in primary adipocytes progenitor cells non-risk participants (n=18), bringing expression to risk levels, but no change for risk participants (n=20). FIG. 10I shows loss of enhancer activity for the 1 kb region surrounding rs1421085 upon C-to-T single nucleotide editing rescue of the C risk allele (restoring the disrupted ARID5B motif). Enhancer activity measures luciferase expression relative to a basal promoter in SGBS adipocytes (n=9). Knock-down of the ARID5B repressor has no effect on enhancer activity in the risk haplotype (lacking the motif), but it leads to loss of repression in the edited construct. This cis-/trans-conditional analysis indicates that enhancer repression occurs only when both the intact motif and the intact factor are present (green, siNT), and absence of either the repressor (siARID5B) or the repressor motif (red) leads to loss of repression, indicating causal role for the ARID5B repressor and the rs1421085 nucleotide variant. FIG. 10J shows endogenous decrease of IRX3 and IRX5 mRNA levels upon ARID5B overexpression in homozygous non-risk (n=18) primary human adipocyte progenitor cells, indicating moderately increased repression. No change is seen in risk allele (n=20) carriers (disrupted ARID5B motif). FIG. 10K shows that knock-down of the ARID5B repressor leads to reduced basal oxygen consumption rate (OCR) in primary human adipose cells from non-risk (n=18) participants (intact ARIDSB motif), resulting in risk-allele levels. ARID5B knock-down has no effect on risk allele (n=20) participants (disrupted ARIDSB motif). This cis-/trans-conditional analysis indicates causality of the ARIDSB upstream repressor acting through the non-risk haplotype. FIG. 10L shows that knock-down of the ARID5B repressor leads to reduced lipid catabolism (catecholamine-stimulated lipolysis rate) estimated by glycerol concentration in the culture medium after isoproterenol stimulation vs. unstimulated (basal) in primary human adipose cells from non-risk (n=18) participants. No change is seen in risk participants (n=20). This cis-/trans-conditional analysis indicates causality of the ARID5B upstream repressor acting through the non-risk haplotype. FIG. 10M summarizes our regulatory model: in the non-risk allele (blue), the ARID5B repressor binds an intact DNA motif and represses enhancer activity. In the risk allele (red), and T-to-C single-nucleotide variant at rs1421085 disrupts the ARIDSB motif, leading to loss of DNA binding, activation of the pre-adipocyte enhancer, and activation of the downstream target genes IRX3 and IRX5.

FIG. 11A shows increased endogenous expression of lipid catabolism marker ACACB and reduced expression of lipid storage markers upon CRISPR/Cas9 single-nucleotide C-to-T genome editing of the rs1421085 risk allele, indicating a shift from energy storage to energy dissipation. FIG. 11B shows increased basal (control) and stimulated (isoproterenol) respiration (oxygen consumption rate) in differentiating primary human adipocyte progenitors upon CRISPR/Cas9 T-to-C editing of rs1421085 rescuing the risk allele (n=5 clonal expansions), indicating that the single-nucleotide change is sufficient to rescue isoproterenol-stimulated increase in cellular energy expenditure indicative of uncoupled respiration and thermogenesis. FIG. 11C shows increased respiration (oxygen consumption rate, OCR) upon C-to-T single-nucleotide rescue of rs1421085 in primary adipocytes from risk-allele participants by CRISPR/Cas9 genome editing of the endogenous locus, indicating single-nucleotide variant causality. Knock-down of ARID5B has no effect on risk-allele carriers (red), but results in decreased respiration in the edited-allele adipocytes (green), indicating causality of the ARID5B repressor acting through the rs1421085 non-risk allele. n=10 clonal expansions were induced to differentiate into adipocytes concomitant with siRNA transfection and analyzed after two days.

FIG. 13 shows that TT cachexia risk allele cells significantly respond to IL-6 and PTHrP stimuli (p<0.001 and p=0.02, respectively). T-to-C CRISPR/Cas9 mediated editing of patient samples (CC→TT rescue) rescues the phenotype of excessive mitochondrial thermogenesis rate.

DETAILED DESCRIPTION OF THE INVENTION

Figures 1A, 1B:
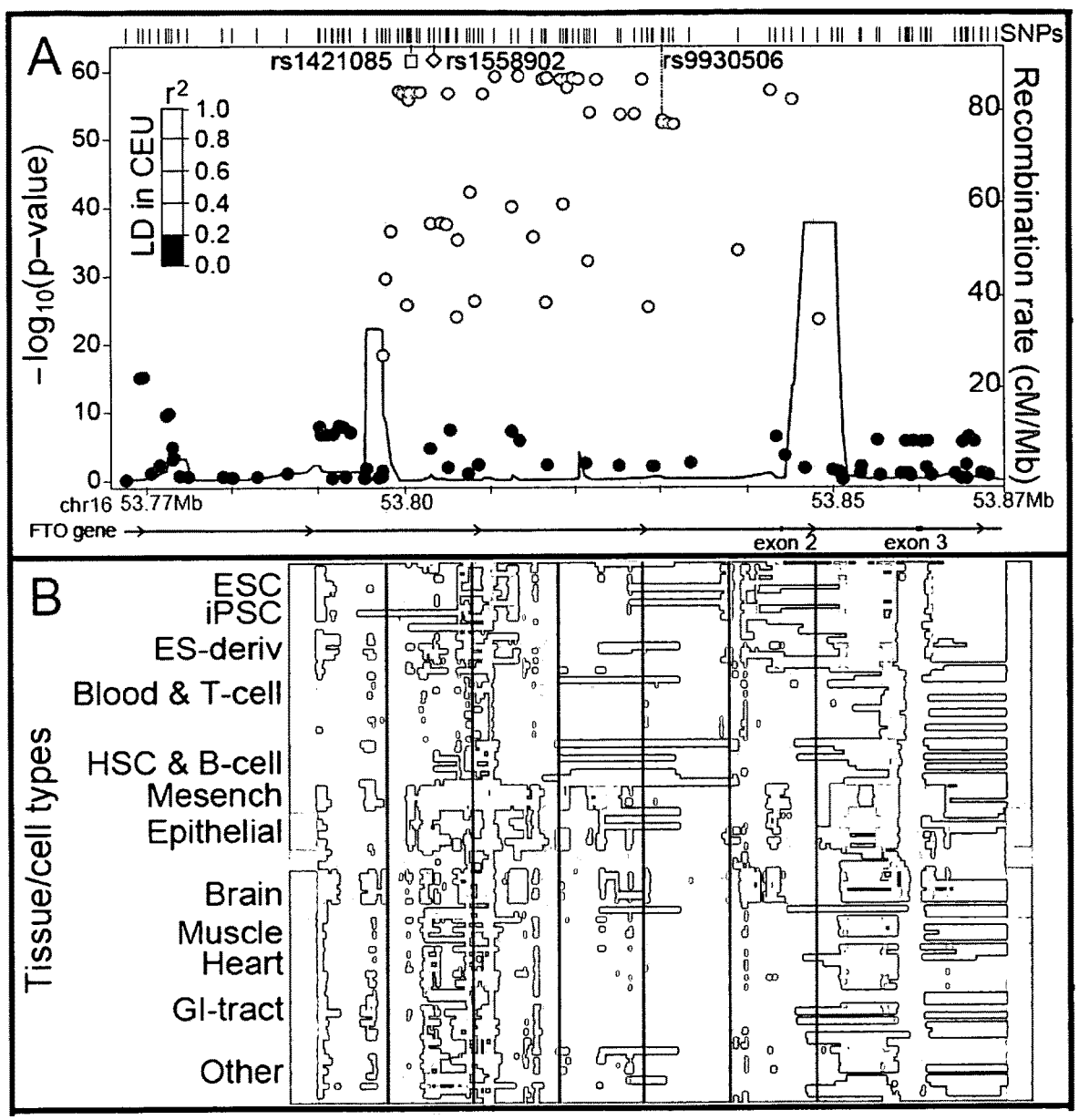
FIGS. 1A-1F. FTO obesity risk haplotype activates a potent enhancer and expression of IRX3 and IRX5 in human adipocyte progenitors.

A description of example embodiments of the invention follows.

The present invention is based, in part, on the identification of the mechanism by which genetic variants in the FTO locus contribute to obesity risk. Described herein is the causal variant whose disruption alters the function of regulatory elements and gene expression levels. Identified herein is an enhancer element, its upstream regulators, and its downstream target genes, that act in early adipocyte differentiation to regulate energy consumption (e.g., thermogenesis) in a tissue-autonomous way. Body-Mass-Index (BMI) has a strong genetic component (50-90% heritability) involving several genes that show expression in the hypothalamus and fulfill roles in appetite regulation (Speliotes et al., Nat. Genetics 42:937-48, 2010; Locke et al., Nature 518:197-206, 2015). The strongest genome-wide association signal for obesity lies in introns 1 and 2 of the FTO gene (Frayling et al., Science 316:889-94, 2007; Dina et al., Nat. Genetics 39:724-26, 2007) and contain 89 common variants (FIG. 1A) in high linkage disequilibrium (LD) in Europeans ($r^2 \geq 0.8$) (Frayling et al., Science 316:889-94, 2007; Dina et al., Nat. Genetics 39:724-26, 2007) across ~47,000 nucleotides, making the identification of the likely causal variant challenging. The associated region lacks protein-altering variants, which has prompted gene-regulatory studies (Fischer et al., Nature 458:894-98, 2009; Stratigopoulos et al., Cell Metab 19:767-79, 2014; Smemo et al., Nature 507:371-75, 2014; Ragvin et al., PNAS 107:776-80, 2010; Jowett et al., Diabetes 59:726-32, 2010) that predict diverse and conflicting targets and tissues, including FTO itself in a whole-body knock-out (Fischer et al., Nature 458:894-98, 2009), IRX3 in pancreas (Ragvin et al., PNAS 107:776-80, 2010) or brain (Smemo et al., Nature 507:371-75, 2014), RBL2 in lymphocytes (Jowett et al., Diabetes 59:726-32, 2010), and RPGRIP1L in brain (Stratigopoulos et al., Cell Metab 19:767-79, 2014). However, a mechanistic basis in humans remains elusive, the relevant cell types and target genes remain unresolved, and the causal variant remains uncharacterized.

The present invention relates, in part, to the identification of a mechanistic basis for the genetic association of the FTO locus with obesity (e.g., anti-cachexia and anti-obesity). The causal genetic variant rs1421085 of FTO disrupts ARID5B repressor binding and de-represses IRX3 (Genbank accession id NC_000016) and IRX5 during early adipocyte differentiation, which leads to a cell-autonomous shift from white adipocyte browning and thermogenesis to lipid storage, increased fat stores, and body weight gain. The results of this finding can be applied to manipulate the circuitry for either anti-cachectic and anti-obesity effects.

As demonstrated herein, the present invention provides that the rs1421085 T-to-C single-nucleotide polymorphism (44% frequency in Europeans) in the FTO obesity risk locus was associated with the disruption of a conserved ARID5B repressor motif in risk-allele carriers, resulting in de-repression of a potent preadipocyte enhancer, which doubled IRX3 and IRX5 expression during early adipocyte differentiation. This de-repression resulted in a cell-autonomous developmental shift from energy-dissipating beige/brite adipocytes to energy-storing white adipocytes, with 4-fold reduced mitochondrial thermogenesis and increased lipid storage. Adipose inhibition of Irx3 in mice reduced body weight and increased energy dissipation, with unchanged physical activity or appetite. Knockdown of IRX3 or IRX5 in primary adipocytes restored 7-fold higher thermogenesis in risk-allele participants, and overexpression led to its 8-fold disruption in protective-allele participants. Repair of the ARID5B motif by CRISPR/Cas9 editing of rs1421085 in primary adipocytes from a risk-allele patient restored IRX3 and IRX5 repression, activated browning expression programs, and restored 7-fold higher thermogenesis.

Moreover, the rs1421085 locus in FTO was shown to have an effect on cachexia, suggesting beneficial effects by manipulating the circuitry for anti-cachectic effects. Cachexia, or "wasting syndrome," is characterized by loss of body weight, muscle atrophy, fatigue, weakness, and significant loss of appetite in people not actively trying to lose weight, and represents a strong risk factor for death in conjunction with various common human diseases; generally, the loss of body mass that cannot be reversed nutritionally. Cachexia occurs in conjunction with various chronic diseases, including cancer, infectious diseases (e.g., AIDS and tuberculosis), chronic obstructive lung disease, autoimmune disorders (e.g. multiple sclerosis), congestive heart failure, familial amyloid polyneuropathy, gadolinium poisoning, mercury poisoning, and hormonal deficiency. Cachexia adversely affects the patients' ability to fight infection and withstand treatment by chemotherapy and radiotherapy, causing the body to waste away with high rates of mortality (Dhanapal, R. et al., J. Oral Maxillofac. Pathol. 15:257-60, 2011).

The pathogenicity of cachexia is multifactorial, involving an interaction of host genetic factors and disease-associated factors (e.g., a tumor). Key characteristic of cachexia is higher resting energy expenditure levels than in healthy individuals, which has been linked to greater browning (and hence increased energy consumption such as thermogenesis) of adipose tissue. At the molecular level, research in mice has revealed that a phenotypic switch from energy-storing white adipose tissue (WAT) to brown fat with increased thermogenesis and consequentially increased energy expenditure is associated with the onset of (cancer-associated) cachexia (Petruzzelli, M. et al. Cell Metab 20:433-447, 2014). Studies have focused on factors secreted by tumors that can induce cachexia. Tumor-derived PTH-related (parathyroid-hormone-related) protein can trigger adipose tissue browning in a cachectic mouse model (Kir, S. et al., Nature 513:100-104, 2014). Furthermore, it was shown that release of cytokine interleukin-6 (IL-6) from the tumor can increase UCP1 expression in WAT in mice, which uncouples mitochondrial respiration toward thermogenesis instead of ATP synthesis, leading to increased energy expenditure in cachectic mice (Petruzzelli, M. et al. Cell Metab 20:433-447, 2014).

As shown herein, the obesity protective TT allele of rs1421085 increases the risk of cachexia by increased browning of adipocytes in humans, in line with the "opposite" metabolic effects in obesity and cachexia. In particular, patients with cancer-associated cachexia generally show decreased gene expression levels of IRX3, IRX5, UCP1, PGC1A, PRDM16, TBX1 in adipose tissue samples compared to healthy controls. This effect was conditional on the rs1421085 TT cachexia risk allele. Further, CRISPR/Cas9 editing of rs1421085 in potential TT cachexia risk allele carriers rescues IL6 and PTHrP-induced browning in human adipocytes. That is, rs1421085 TT cachexia risk allele carrier cells significantly respond to IL-6 and PTHrP stimuli. Additionally, T-to-C CRISPR/Cas9 mediated editing of patient samples rescues the phenotype of excessive mitochondrial thermogenesis rate. As such, at the molecular level, cachexia can be seen to involve the opposite metabolic situation as compared to obesity, wherein energy dissipation as heat via inducible thermogenesis (which involves beige/brite adipocytes that can emerge within white fat tissue), can be markedly reduced. Thus, the mechanistic basis for the genetic association of the FTO locus with obesity is applicable in the context of cachexia (e.g., cancer-associated cachexia). As disclosed herein, a single-nucleotide alteration can recapitulate the molecular and cellular signatures of obesity and cancer-associated cachexia.

Methods of Modulating Energy Consumption in Adipocytes

Accordingly, in one aspect, the present invention provides a method of modulating energy consumption (e.g, thermogenesis) in an adipocyte, comprising contacting the adipocyte with an effective amount of one or more agents that modulate the function of one or more of iroquois homeobox protein 3 (IRX3), iroquois homeobox protein 5 (IRX5), AT-rich interactive domain-containing protein 5B (ARID5B), or genetic variant rs1421085 (of fatso/fat mass and obesity associated (FTO) gene). In certain embodiments, the method comprises contacting the adipocyte with an effective amount of two or more agents that modulate two or more of IRX3, IRX5, ARID5B, or genetic variant rs1421085. In some embodiments, the method also includes modulating the function of obesity browning enhancer 1 (OBE1).

As used herein, "genetic variant rs1421085" refers to a naturally-occurring and non-naturally occurring variant of the rs1421085 allele of the FTO gene. As described herein, a genetic variant rs1421085 comprises a TT, CC, T, or C.

As used herein, "obesity browning enhancer 1 (OBE1)" refers to a region of the FTO locus that encompasses the genetic variant rs1421085. As described herein, OBE1 comprises enhancer and regulatory regions, in addition to, or separate from, genetic variant rs1421085, that can be modified or acted upon to modulate energy consumption in cells (e.g., adipocytes). The genomic coordinates of OBE1 include chr16:53, 800,400-53,813,200.

As used herein, "energy consumption" refers to energy dissipation or storage in a cell, e.g., adipocyte. Thus, modulating energy consumption includes modulating one or more of thermogenesis, mitochondrial uncoupling, mitochondrial biogenesis, mitochondrial activity, lipid utilization, lipid storage, adipocyte browning, adipocyte beiging, or adipocyte whitening.

The term "thermogenesis" is understood in the art as energy dissipation in the form of heat. As those of skill in the art would understand, energy dissipation as heat occurs via constitutive thermogenesis in mitochondria-rich brown adipocytes, and inducible thermogenesis in beige adipocyte in white fat. Physiologically, thermogenesis is triggered by mechanisms within cells per se, or by the sympathetic nervous system (e.g., via β-adrenergic receptor agonists), in response to stimuli (e.g., exercise, diet, or cold exposure). Mitochondrial thermogenesis regulators control uncoupling protein 1 (UCP1) expression (Wu et al., Cell, 150:366-76, 2012; Kong et al., Cell, 158:69-83, 2014), which depolarizes the inner mitochondrial membrane causing protein transfer and heat dissipation. Any change in thermogenesis can be measured by methods known in the art (e.g., oxygen consumption rate, as described herein). At the organismal level, energy expenditure measurements can be used.

As used herein, "modulating energy consumption" (e.g., thermogenesis) refers to a change, e.g., an increase or decrease in, e.g., thermogenesis as measured by known methods. The thermogenesis may be increased or decreased by about 2-fold, about 3-fold, about 4-fold, about 5-fold, about 6-fold, about 7-fold, about 8-fold, about 9-fold, about 10-fold, about 11-fold, about 12-fold, about 13-fold, about 14-fold, about 15-fold, about 16-fold, about 17-fold, about 18-fold, about 19-fold, or about 20-fold. Modulating thermogenesis can re-establish or off-set the balance between energy storage and energy dissipation in a cell (e.g., an adipocyte). Thus, modulating thermogenesis can lead to, e.g., weight loss or weight gain.

As used herein, "pro-obesity," used interchangeably with "anti-cachexia," refers to modulating thermogenesis such that energy dissipation is decreased, to reduce energy dissipation and increase energy storage (e.g., as lipid). Modulating thermogenesis for pro-obesity effect is desirable in, e.g., in an individual diagnosed with a disease that can cause cachexia, as described herein, wherein the individual carries an obesity protective TT allele at rs1421085. Anti-cachexia does not refer to promoting obesity, but rather to modulating thermogenesis to the benefit of a patient in need of an anti-cachectic therapy.

As used herein, "anti-obesity" refers to modulating thermogenesis such that energy dissipation is increased, to reduce lipid storage. Modulating thermogenesis for anti-obesity effect is desirable in, e.g., an obese individual (e.g., an individual with a BMI of greater than 25 kg/m$^2$, or a BMI of greater than 30 kg/m$^2$), or in an individual at risk or predisposed for obesity.

The term "energy consumption pathway" refers to a network of genes and proteins that regulate energy storage and dissipation in cells. In some aspects, the energy consumption pathway includes "thermogenesis pathway," "thermogenesis circuitry," "regulatory circuitry" (and like terms which are used interchangeably), which refer to a network of genes and proteins that regulate or maintain thermogenesis in a cell (e.g., adipocyte). In a particular embodiment, the pathway refers to any one or more of the genes and gene products (e.g., transcribed or translated gene product) identified herein (e.g., genetic variant rs1421085 of the FTO locus, OBE1, ARID5B, IRX3, and IRX5). Thus, by way of example, an agent that modifies the thermogenesis pathway is an agent that acts on one or more of the genes and/or gene product (e.g., transcribed or translated product) in the network of genes and proteins (the targets) that regulate or maintain thermogenesis in an adipocyte to modulate thermogenesis. In some embodiments, the agent modifies the targets IRX3, IRX5, ARID5B, OBE1, and/or the genetic variant rs1421085

Generally, reference to a gene or protein name (e.g., IRX3) indicates either its gene or gene product (e.g., transcribed or translated product), unless clearly one or the other is intended, based on context. For example, consistent with known convention, an italicized name, e.g., "IRX3" indicates the human IRX3 gene, rather than the IRX3 protein. Additionally, whether reference is being made to the gene or the protein can be determined based on context. In other cases, reference to a gene name indicates either its gene or gene product.

As used herein, "modulate the function" in the context of modulating a gene or protein (e.g., modulate IRX3 function) refers to a change in the function or activity of the gene or gene product (e.g., transcribed or translated product) of interest (e.g., IRX3, IRX5, ARID5B, or the genetic variant rs1421085) that confers an increase or decrease in thermogenesis in a cell (e.g., adipocyte). For example, the change in the function or activity includes, without limitation, a decrease in, or inhibition of, protein expression (e.g., use of agents that modulate a regulatory control element of a gene; use of siRNA, antisense, miRNA, long non-coding ribonucleic acid, and/or genome editing system to decrease or inhibit protein expression); an increase in protein expression (e.g., use of agents that modulate a regulatory control element of a gene; genome editing to enhance expression; manipulation of the promoter/enhancer elements of a gene); an inhibition of protein function (e.g., an antibody, or antigen binding fragments thereof, capable of inhibiting protein activity; or an aptamer); or an enhancement of protein function (e.g., an antibody, or antigen binding fragments thereof, that increases the function/activity of a protein; mutagenesis of a gene of interest to generate a protein with an extended half-life). In the context of the genetic variant rs1421085, modulating its function includes, e.g., inhibiting or enhancing its ability to bind to a repressor or an enhancer (e.g., altered capability of ARDI5B to bind at position rs1421085). Similarly, in the context of OBE1, modulating its function includes, e.g., inhibiting or enhancing its ability to bind to a repressor or an enhancer, thereby modulating energy consumption in cells (e.g., adipocytes). By way of example, OBE1 function that is, for example, increased tends towards energy storage. In certain embodiments, the activity or function of IRX3, IRX5, ARID5B, or the genetic variant rs1421085 is modulated to a degree necessary to modulate energy consumption (e.g., thermogenesis), as defined herein.

In some embodiments, IRX3, IRX5, ARID5B, OBE1, or the genetic variant rs1421085 can be modulated according to known methods as well as methods described herein to inhibit or enhance its function (e.g., via modulation of transcription, translation, and/or protein activity). In the case of a non-expressed region of a gene (e.g., the genetic variant rs1421085), modulation of the variant locus prevents or enhances its function by inhibiting or enhancing, e.g., the binding of an effector molecule (e.g., a repressor protein). For example, if anti-obesity (or, e.g., increased thermogenesis leading to energy dissipation) is the desired outcome in an adipocyte that is in a pro-obesity state, then the function of genetic variant rs1421085 can be altered to enhance its function (e.g., binding to ARID5B) to increase energy dissipation (e.g., thermogenesis). In additional embodiments, the modulation can alter the locus of a gene, which includes enhancer (e.g., distal enhancer) and promoter (e.g., proximal regulatory) regions of a gene. Further, the modulation can alter a transcribed product of a gene.

As used herein, "protein" and "polypeptide" are used interchangeably to denote a polymer of at least two amino acids covalently linked by an amide bond, regardless of length or post-translational modification (e.g., glycosylation or phosphorylation). The term "protein" encompasses a naturally-occurring full-length protein as well as a functional fragment of the protein.

The term "functional fragment" refers to a portion of a protein that retains some or all of the activity or function (e.g., biological activity or function) of the full-length protein, such as, e.g., the ability to bind and/or interact with or modulate another protein or nucleic acid. The functional fragment can be any size, provided that the fragment retains, e.g., the ability to bind and interact with another protein or nucleic acid.

As used herein, an "effective amount" of an agent refers to an amount capable of modulating thermogenesis, as described herein. In some embodiments, the effective amount can differ depending on whether one or more than one agent is used to modulate thermogenesis in an adipocyte. For example, if solely one agent is used against one target, a greater effective amount may be required to produce the effect than if the agent is used in combination with another agent that, e.g., either targets another one or more members in the network of genes or proteins of the thermogenesis pathway, or modulates the same target but by a different mechanism (e.g., two different siRNAs that target different regions of IRX3, or an siRNA to IRX3 in combination with an antibody to IRX3). In certain embodiments, an agent encompasses a mixture of, e.g., either a mixture of small interfering ribonucleic acid (siRNAs) or a mixture of synthetic guide RNAs (sgRNAs) against one target.

As used herein, "adipocyte" refers to any cell in the adipocyte lineage, including precursor cells that differentiate into mature adipocytes. In certain embodiments, the adipocyte includes, e.g., a mesenchymal stem cell, a preadipocyte, a mature white adipocyte, a mature beige adipocyte, or a mature brown adipocyte. In some embodiments, adipocytes also include precursor cells in early stages of development, including stem cell adipocyte precursors (e.g., embryonic stem cells or induced pluripotent stem cells). In a particular embodiment, the adipocyte is a human adipocyte.

Any suitable agent can be used to modulate one or more gene and/or gene product (e.g., transcribed or translated product such as mRNA or protein, respectively) of interest. In one embodiment, one or more agents can be used to modulate one or more regulatory elements of the IRX3, IRX5, ARID5B, or OBE1 gene locus by, e.g., a targeted modification to one or more regulatory elements (using, e.g., a genome editing system such as CRISPR/Cas9). Examples of regulatory elements that can be modified according to the present methods include, e.g., the promoter region and/or upstream regulatory enhancers of IRX3, IRX5, or ARID5B. In related embodiments, an example of a regulatory element is the genetic variant rs1421085. In other embodiments, one or more repressive regulators (e.g., a Polycomb repressive complex) can be used to modulate one or more regulatory elements of the IRX3, IRX5, or ARID5B gene.

In some embodiments, one or more agents that modulate one or more regulatory elements of IRX3, IRX5, or ARID5B include naturally-occurring as well as non-naturally occurring (e.g., engineered polypeptide) proteins ("regulators") that target the regulatory elements described herein. In specific embodiments, the naturally-occurring regulators can be expressed in adipocytes or non-adipocytes. In certain embodiments, the regulatory elements can be modulated using a regulator linked to a genome guidance system that targets one or more of an IRX3 promoter, an IRX3 enhancer, an IRX5 promoter, an IRX5 enhancer, an ARID5B promoter, or an ARID5B enhancer. The regulator may include, for example, a transcription factor activation domain, a transcription factor repressive domain, a pioneer factor, a chromatin remodeling factor, a histone methyl transferase, a histone acetyl transferase, a post-translational modifier of a histone protein, and a DNA methyl-transferase. Examples of genome guidance systems include a dead Cas9 (dCas9) CRISPR interference (CRISPR/i) system, a dCas9 CRISPR activation (CRISP/a) system, a transcription activator-like effector (TALE), or a DNA binding domain of a zinc-finger nuclease (ZFN). Methods of using such agents are readily available and known in the art.

As used herein, "transcription factor activation domain" is used to denote a functional fragment of protein that retains some or all of the activity or function (e.g, biological activity or function) of the full-length transcription factor, such as, e.g., the ability to bind and/or interact with or modulate another protein or nucleic acid to activate the expression of adjacent genes.

As used herein, "transcription factor repressor domain" is used to denote a functional fragment of protein that retains some or all of the activity or function (e.g, biological activity or function) of the full-length transcription factor, such as, e.g, the ability to bind and/or interact with or modulate another protein or nucleic acid to repress the expression of adjacent genes.

As used herein, "pioneer factor" is used to denote a class of transcription factors that can directly bind to condensed chromatin and genomic DNA to modulate (activate or repress) the expression of adjacent genes.

As used herein, "chromatin remodeler" is used to denote a naturally occurring protein that performs dynamic modification of chromatin to allow access of condensed genomic DNA to the regulatory transcription machinery proteins, and thereby control gene expression.

As used herein, "histone methyl transferase" is used to denote a naturally occurring protein of the class of chromatin remodelers that mediate the addition of methyl groups on histones at specific certain sites. As those of skill in the art would understand, this is a central mechanism in the regulation of gene expression.

As used herein, the term "regulatory element of IRX3" refers to any of a class of naturally occurring functional gene regulatory elements that directly modulate the expression of the IRX3 gene (chr16:54283304-54286763), including cis and trans-acting promoters, enhancers, repressors. Promoter regions for IRX3: Chr16: 53451001-53451600 (PromU), 53467801-53468200 (PromU), 53468201-53468400 (TssA), 53468401-53470200 (PromD1), 53470201-53471000 (PromD2), 53536001-53536600 (PromD1), 53536601-53537200 (TssA), 53537401-53537600 (TssA), 53537601-53537800 (PromU), 53537801-53538000 (TssA), 53538001-53538800 (PromU), 53544001-53544600 (PromU), 53584201-53584400 (PromU), 53698801-53699000 (PromU), 53737001-53737200 (PromD2), 53737201-53737800 (PromD1), 53737801-53738000 (TssA), 53738001-53738800 (PromD1), 53738801-53740000 (PromD2), 53780001-53780400 (PromD1), 54061401-54061800 (PromU), 54209201-54209600 (PromU), 54209601-54209800 (TssA), 54209801-54210400 (PromU), 54227401-54228600 (PromU), 54316601-54318200 (PromD2), 54318201-54318400 (PromD1), 54318401-54318800 (TssA), 54318801-54319800 (PromD1), 54319801-54320400 (TssA), 54320401-54320600 (PromU), 54320601-54321000 (TssA), 54321001-54321800 (PromU), 54407401-54408600 (PromU), 54464601-54465400 (PromU), 54689001-54689600 (PromU), 54960001-54960200 (PromD2), 54961401-54962200 (PromD1), 54962201-54963400 (TssA), 54963401-54964400 (PromD1), 54964401-54964800 (TssA), 54964801-54967400 (PromD1), 54970001-54972600 (PromD1), 54972601-54972800 (PromU). IRX3 enhancer elements (per class, start:length in hundreds of nucleotides). TxReg: 53534800:12, 53747600:18, 53778600:2, 53796200:6, 53801800:4, 53803000:10, 53806200:6, 53807400:10, 53809000:10, 53810600:4, 54960200:12, 54967400:26; TxEnh5': 53291000:8, 53747200:4, 53749400:10, 53751400:4, 53752400:6, 53754000:2, 53778200:4, 53780600:6, 53787600:6, 53789000:14, 53795600:6, 53797400:2, 53804400:18, 53807200:2, 53808400:6, 53811000:32, 53821800:4, 53824600:6; TxEnh3': 53290400:6, 53291800:4, 53300200:4, 53315000:24, 53325200:14, 53328000:10, 53499400:6, 53515600:8, 53526000:10, 53844200:8, 54146000:8, 54316000:2; TxEnhW: 53471000:2, 53473000:4, 53736800:2, 53740000:4, 53741600:4, 53745200:4, 53745800:2, 53746600:6, 53751800:2, 53752200:2, 53754200:2, 53759400:4, 53760200:16, 53766400:4, 53777600:6, 53781200:2, 53787400:2, 53788800:2, 53791200:2, 53795400:2, 53800400:8, 53801600:2, 53814200:16, 53818200:12, 53821600:2, 53826200:6, 53829400:2, 53842600:2, 53871600:4, 54955000:4, 54956800:6, 54959400:6; EnhA1: 53698000:8, 53699000:12, 53778800:12, 53802200:8, 53810000:6, 53822600:6, 53823400:2, 53850600:14, 53855600:4, 53856200:4, 53915600:6, 53946400:12, 53986200:6, 54114400:2, 54170000:6, 54376600:2, 54465400:2, 54480800:4, 54493600:8, 54544600:4; EnhA2: 53538800:2, 53543800:2, 53697400:6, 53700600:6, 53702600:10, 53780400:2, 53790400:6, 53796800:2, 53804000:4, 53806800:2, 53823200:2, 53850400:2, 53852000:4, 53855200:4, 53856000:2, 53856600:8, 53899000:8, 53900000:2, 53906600:2, 53907000:2, 53926000:12, 53927800:6, 53933600:2, 53945800:2, 53947600:6, 53983600:4, 53986800:4, 54002200:12, 54033400:10, 54034600:4, 54060400:10, 54061800:4, 54114800:4, 54169200:8, 54170600:2, 54228600:2, 54273400:10, 54300600:4, 54359800:4, 54376400:2, 54376800:2, 54407200:2, 54465600:2, 54480000:8, 54481400:12, 54494400:4, 54495600:6, 54496600:2, 54522800:6, 54537000:2, 54545000:6, 54681200:4, 54682000:2, 54689600:2; EnhAF: 53539000:2, 53541000:2, 53543600:2, 53553000:2, 53697200:2, 53700200:4, 53701200:4, 53712600:6, 53728600:12, 53807000:2, 53822400:2, 53823600:2, 53842800:10, 53849800:6, 53852400:4, 53855000:2, 53857400:2, 53871400:2, 53898200:2, 53898800:2, 53899800:2, 53906000:6, 53906800:2, 53907200:2, 53907800:2, 53915000:6, 53916200:4, 53925800:2, 53927200:6, 53928400:10, 53945200:6, 53946000:4, 53948200:6, 53983400:2, 53987200:2, 54025000:16, 54033200:2, 54034400:2, 54035000:2, 54060200:2, 54111400:4, 54114000:4, 54114600:2, 54115200:4, 54170800:2, 54228800:2, 54274400:2, 54300200:2, 54376200:2, 54377000:4, 54389600:2, 54431800:2, 54481200:2, 54494800:4, 54495400:2, 54496200:4, 54496800:2, 54522200:6, 54527000:6, 54544400:2, 54545600:2, 54663800:6, 54667400:4, 54681600:4, 54977600:4, 55035000:4, 55035800:6, 55069600:4, 55096000:10, 55150000:4, 55151200:2; EnhW1: 3369000:2, 53463000:4, 53467600:2, 53583800:4, 53584400:2, 53703600:2, 53714800:4, 53932800:8, 53959200:2, 53986000:2, 54002000:2, 54008400:4, 54062200:2, 54097400:4, 54100600:2, 54152600:6, 54206000:4, 54209000:2, 54210400:2, 54275200:4, 54359400:4, 54360200:2, 54368800:8, 54464400:2, 54540600:4, 54681000:2, 54684000:2, 54688800:2, 54691400:6, 54981000:4; EnhW2: 53368600:4, 53540600:4, 53541200:2, 53552600:4, 53575000:8, 53581000:4, 53583600:2, 53593200:6, 53661000:2, 53696200:2, 53696800:4, 53702400:2, 53706600:4, 53712400:2, 53729800:2, 53786400:10, 53791000:2, 53823800:8, 53825200:2, 53863200:4, 53882000:16, 53886400:6, 53897400:8, 53898400:4, 53900200:8, 53907400:4, 53925600:2, 53929400:14, 53932600:2, 53933800:2, 53945000:2, 53956200:6, 53959400:6, 54060000:2, 54068400:2, 54084200:8, 54097200:2, 54100400:2, 54111200:2, 54152400:2, 54153200:2, 54171000:2, 54205800:2, 54271000:2, 54273200:2, 54274600:4, 54315200:2, 54316200:2, 54360400:4, 54369600:2, 54389200:4, 54390200:6, 54408600:2, 54432000:12, 54465800:6, 54479400:6, 54482600:2, 54493200:4, 54523400:4, 54526800:2, 54527600:4, 54536800:2, 54537400:6, 54540400:2, 54541000:2, 54561000:6, 54602800:2, 54661600:4, 54666800:6, 54682200:6, 54683800:2, 54688600:2, 54689800:16, 54951200:6, 54955400:6, 54978000:4, 54980600:4, 55034400:6, 55036400:4, 55116000:2, 55135200:2, 55149800:2, 55153000:4, 55154200:4, 55171000:2; EnhAc: 53539200:2, 53553200:2, 53714600:2, 53797000:4, 53822200:2, 53843800:4, 53854800:2, 53875400:6, 53908000:2, 53916600:2, 53987400:14, 53996400:2, 54065800:2, 54113800:2, 54300000:2, 54300400:2, 54380400:2, 54407000:2, 54431200:6, 54495200:2, 54497000:2, 54545800:2, 54552800:10, 54556800:4, 54663600:2, 54664400:22, 54667800:6, 54754000:8, 54948000:4, 54977400:2, 55035400:4, 55070000:8, 55097000:2, 55150400:8, 55152400:2, 55155000:2, 55180800:6; DNase: 3403800:4, 53449400:2, 53463400:4, 53467400:2, 53569000:2, 53622000:2, 53632800:16, 53710000:2, 53949600:4, 53956800:2, 53959000:2, 53979800:4, 53981000:2, 53992400:4, 54005400:4, 54008800:2, 54106200:2, 54157800:2, 54159200:2, 54186400:2, 54250200:6, 54270600:4, 54299600:4, 54314800:4, 54353000:2, 54380000:4, 54404600:2, 54434200:2, 54436200:4, 54441600:4, 54456400:2, 54458200:2, 54479200:2, 54502800:8, 54507200:4, 54522000:2, 54560800:2, 54636600:4, 54686400:2, 54851600:2, 54881200:2, 54984600:4, 54991400:2, 55044600:4, 55049200:2, 55055600:2, 55078200:2, 55086800:2, 55111200:2, 55117000:2, 55170400:6, 55178600:4, 55183600:4, 55185600:6, 55187000:2, 55284800: 2.

As used herein, the term "regulatory element of IRX5" refers to any of a class of naturally occurring functional gene regulatory elements that directly modulate the expression of the IRX5 gene (chr16:54930862-54934485), including cis and trans-acting enhancers, promoters, and repressors.

Promoter regions for IRX5 on chromosome 16. Format is Start-End (class): 54061401-54061800 (PromU), 54209201-54209600 (PromU), 54209601-54209800 (TssA), 54209801-54210400 (PromU), 54227401-54228600 (PromU), 54316601-54318200 (PromD2), 54318201-54318400 (PromD1), 54318401-54318800 (TssA), 54318801-54319800 (PromD1), 54319801-54320400 (TssA), 54320401-54320600 (PromU), 54320601-54321000 (TssA), 54321001-54321800 (PromU), 54407401-54408600 (PromU), 54464601-54465400 (PromU), 54689001-54689600 (PromU), 54960001-54960200 (PromD2), 54961401-54962200 (PromD1), 54962201-54963400 (TssA), 54963401-54964400 (PromD1), 54964401-54964800 (TssA), 54964801-54967400 (PromD1), 54970001-54972600 (PromD1), 54972601-54972800 (PromU), 55400801-55401000 (PromU), 55504801-55505400 (PromU), 55509601-55510400 (PromU), 55512601-55513000 (PromU), 55513001-55513200 (TssA), 55513201-55514800 (PromD1), 55542801-55544000 (PromD1), 55544001-55544200 (PromD2), 55794401-55794800 (PromU), 55866401-55866800 (PromU).

IRX5 enhancer elements (per class, start:length in hundreds of nucleotides): TxReg: 54960200:12, 54967400:26, 55514800:28, 55519000:2, 55520000:24, 55528600:2, 55529200:8, 55533200:6, 55534400:10, 55536000:14, 55542600:2; TxEnh5': 55517600:2, 55518600:4, 55519200:8, 55522400:34, 55528400:2, 55529000:2, 55530000:8, 55535400:6; TxEnh3': 54146000:8, 54316000:2, 55526600:18, 55530800:24, 55537400:10, 55542400:2, 55547600:2, 55566000:2, 55610400:6; TxEnhW: 4955000:4, 54956800:6, 54959400:6, 55517800:8, 55544200:4; EnhA1: 53946400:12, 53986200:6, 54114400:2, 54170000:6, 54376600:2, 54465400:2, 54480800:4, 54493600:8, 54544600:4, 55401000:8, 55473400:4, 55505400:10, 55509400:2, 55510400:14, 55512400:2, 55528800:2, 55533800:2, 55534200:2, 55602400:4, 55712800:2; EnhA2: 53933600:2, 53945800:2, 53947600:6, 53983600:4, 53986800:4, 54002200:12, 54033400:10, 54034600:4, 54060400:10, 54061800:4, 54114800:4, 54169200:8, 54170600:2, 54228600:2, 54273400:10, 54300600:4, 54359800:4, 54376400:2, 54376800:2, 54407200:2, 54465600:2, 54480000:8, 54481400:12, 54494400:4, 54495600:6, 54496600:2, 54522800:6, 54537000:4, 54545000:6, 54681200:4, 54682000:2, 54689600:2, 55400600:2, 55401800:6, 55471200:4, 55473200:2, 55504400:4, 55506600:4, 55509000:4, 55572800:8, 55576400:4, 55586400:6, 55593200:2, 55601200:2, 55601800:6, 55602800:2, 55869800:6; EnhAF: 3945200:6, 53946000:4, 53948200:6, 53983400:2, 53987200:2, 54025000:16, 54033200:2, 54034400:2, 54035000:2, 54060200:2, 54111400:4, 54114000:4, 54114600:2, 54115200:4, 54170800:2, 54228800:2, 54274400:2, 54300200:2, 54376200:2, 54377000:4, 54389600:2, 54431800:2, 54481200:2, 54494800:4, 54495400:2, 54496200:4, 54496800:2, 54522200:6, 54527000:6, 54544400:2, 54545600:2, 54663800:6, 54667400:4, 54681600:4, 54977600:4, 55035000:4, 55035800:6, 55069600:4, 55096000:10, 55150000:4, 55151200:2, 55331800:2, 55471600:6, 55473000:2, 55504200:2, 55506400:2, 55511800:6, 55534000:2, 55562800:8, 55568600:2, 55572600:2, 55573600:2, 55576200:2, 55576800:2, 55586000:4, 55587000:2, 55592600:6, 55593400:4, 55597000:4, 55601400:4, 55603000:2, 55609400:4, 55610200:2, 55712200:6, 55713000:2; EnhW1: 53932800:8, 53959200:2, 53986000:2, 54002000:2, 54008400:4, 54062200:2, 54097400:4, 54100600:2, 54152600:6, 54206000:4, 54209000:2, 54210400:2, 54275000:4, 54359400:4, 54360200:2, 54368800:8, 54464400:2, 54540600:4, 54681000:2, 54684000:2, 54688800:2, 54691400:6, 54981000:4, 55291800:2, 55317400:10, 55328400:8, 55499200:4, 55597800:4, 55696400:2, 55702400:2, 55706200:4, 55706800:4, 55870400:2; EnhW2: 3932600:2, 53933800:2, 53945000:2, 53956200:6, 53959400:6, 54060000:2, 54068400:2, 54084200:8, 54097200:2, 54100400:2, 54111200:2, 54152400:2, 54153200:2, 54171000:2, 54205800:2, 54271000:2, 54273200:2, 54274600:4, 54315200:2, 54316200:2, 54360400:4, 54369600:2, 54389200:4, 54390200:6, 54408600:2, 54432000:12, 54465800:6, 54479400:6, 54482600:2, 54493200:4, 54523400:4, 54526800:2, 54527600:4, 54536800:2, 54537400:6, 54540400:2, 54541000:2, 54561000:6, 54602800:2, 54661600:4, 54666800:6, 54682200:6, 54683800:2, 54688600:2, 54689800:16, 54951200:6, 54955400:6, 54978000:4, 54980600:4, 55034400:6, 55036400:4, 55116000:2, 55135200:2, 55149800:2, 55153000:4, 55154200:4, 55171000:2, 55317200:2, 55328200:2, 55332000:4, 55402400:2, 55503400:8, 55507000:2, 55508800:2, 55547800:2, 55577200:4, 55589200:4, 55592400:2, 55594000:4, 55596600:4, 55597400:4, 55598200:4, 55601000:2, 55603200:4, 55609200:2, 55639600:8, 55695600:8, 55696600:16, 55702000:4, 55702600:4, 55707200:2, 55712000:2, 55850000:6; EnhAc: 53987400:14, 53996400:2, 54065800:2, 54113800:2, 54300000:2, 54300400:2, 54380400:2, 54407000:2, 54431200:6, 54495200:2, 54497000:2, 54545800:2, 54552800:10, 54556800:4, 54663600:2, 54664400:22, 54667800:6, 54754000:8, 54948000:4, 54977400:2, 55035400:4, 55070000:8, 55097000:2, 55150400:8, 55152400:2, 55155000:2, 55180800:6, 55299200:4, 55331400:4, 55384400:6, 55471000:2, 55472400:8, 55560800:2, 55568800:26, 55573800:4, 55587200:2, 55593800:2, 55609800:4; DNase: 53949600:4, 53956800:2, 53959000:2, 53979800:4, 53981000:2, 53992400:4, 54005400:4, 54008800:2, 54106200:2, 54157800:4, 54159200:2, 54186400:2, 54250200:6, 54270600:4, 54299600:4, 54314800:4, 54353000:2, 54380000:4, 54404600:2, 54434200:2, 54436200:4, 54441600:4, 54456400:2, 54458200:2, 54479200:2, 54502800:8, 54507200:4, 54522000:2, 54560800:2, 54636600:4, 54686400:2, 54851600:2, 54881200:2, 54984600:4, 54991400:2, 55044600:4, 55049200:2, 55055600:2, 55078200:2, 55086800:2, 55111200:2, 55117000:2, 55170400:6, 55178600:4, 55183600:4, 55185600:6, 55187000:2, 55284800:2, 55292000:4, 55298800:4, 55314600:2, 55316400:8, 55331000:4, 55383800:6, 55406800:6, 55423400:2, 55426800:2, 55428000:2, 55445200:2, 55461200:2, 55478800:2, 55487800:2, 55499000:2, 55549200:2, 55560400:4, 55577600:2, 55606400:4, 55659600:2, 55675400:4, 55676600:2, 55679600:6, 55703000:2, 55706600:2, 55735600:4, 55737400:2, 55746200:4, 55786800:2, 55867200:2, 55869600:2, 55873200:2, 55876800:2, 55887000:4.

As used herein, the term "regulatory element of ARID5B" refers to any of a class of naturally occurring functional gene regulatory elements that directly modulate the expression of the ARID5B gene (chr10:61901300-62096944), including cis and trans-acting enhancers and repressors.

ARID5B Promoter regions in chromosome 10. Forma: start-end (class). 61121001-61121200 (PromU), 61121601-61122200 (PromU), 61122201-61122800 (TssA), 61122801-61123200 (PromU), 61469401-61469600 (TssA), 61469601-61469800 (PromU), 61616201-61617200 (PromD2), 61632401-61632600 (PromD2), 61632601-61633400 (PromD1), 61633401-61633600 (PromD2), 61664801-61666000 (PromD1), 61666001-61666800 (TssA), 61666801-61668200 (PromU), 61668201-61668400 (TssA), 61668401-61668800 (PromU), 61751401-61751600 (PromU), 61842601-61843000 (PromU), 61883201-61883800 (PromU), 61899401-61900800 (PromU), 61926801-61927000 (PromU), 61927001-61927200 (TssA), 61927201-61927400 (PromU), 61946401-61946600 (PromU), 61997401-61998200 (PromU), 62059801-62060600 (PromU), 62127201-62127400 (PromU), 62331801-62333000 (PromU), 62537601-62538200 (TssA), 62538201-62539600 (PromD1), 62539601-62540400 (PromD2), 62541201-62542600 (PromD2), 62576201-62576400 (PromU), 62701201-62702400 (PromD2), 62702401-62703600 (PromD1), 62703601-62704200 (TssA), 62704201-62705000 (PromU), 63043801-63044200 (PromU).

ARID5B enhancer elements in chromosome 10 (per class, start: length). TxReg: 61663400:14; TxEnh5':61598800:6, 61636800:10, 61653600:10, TxEnh3' 61553800:6, 61559200:4; TxEnhW: 61588400:6, 61598600:2, 61615800:4, 61617200:8, 61624600:6, 61628600:2, 61632000:4, 61633600:4, 61636600:2, 61653400:2, 61654600:16, 61658200:4, 61661400:2, 61663200:2, 62540400:2, 62541000:2, 62542600:4, 62547000:2; EnhA1 61096200:10, 61142600:10, 61147200:4, 61148000:4, 61296200:8, 61321200:2, 61408600:2, 61800000:4, 61898600:8, 61900800:4, 62042800:4, 62064800:8, 62073200:2, 62074000:2, 62074400:2, 62113200:6, 62144000:4, 62144800:4, 62175000:2, 62185400:2, 62185800:4, 62186400:4, 62189000:8, 62190000:4, 62570200:8, 62576800:4, 62673800:16, 62723600:16, 63043600:2, 63061800:2, 63064000:6; EnhA2: 61096000:2, 61097200:2, 61126400:2, 61132200:8, 61147600:2, 61194400:4, 61297200:2, 61321400:8, 61408400:2, 61408800:2, 61413600:6, 61800400:2, 61803000:12, 61860400:2, 61864400:14, 61875000:4, 61882600:6, 61901200:8, 61908200:2, 61942200:8, 61945400:2, 61996600:8, 61998200:2, 62042200:6, 62043200:4, 62065600:2, 62072600:6, 62073400:6, 62074200:2, 62074600:2, 62109000:16, 62113000:2, 62113800:6, 62126800:4, 62143200:8, 62144400:4, 62145200:2, 62173800:12, 62175200:2, 62183800:4, 62185000:4, 62185600:2, 62186200:2, 62186800:2, 62188000:6, 62188800:2, 62189800:2, 62190400:2, 62193200:6, 62240600:4, 62568400:10, 62569800:4, 62571000:2, 62576600:2, 62577200:4, 62578200:6, 62587600:12, 62655600:2, 62656000:8, 62673400:4, 62675400:2, 62677400:2, 62698000:2, 62700000:12, 62715800:2, 62722800:8, 62725200:2, 62916600:12, 62924200:8, 63031000:8, 63043400:2, 63061400:4, 63063400:6, 63064600:2; EnhAF: 61075400:2, 61082600:2, 61095800:2, 61132000:2, 61133000:4, 61142200:4, 61143600:2, 61146800:4, 61147800:2, 61148400:2, 61295600:6, 61321000:2, 61344800:2, 61414200:2, 61433800:10, 61600000:2, 61804200:4, 61860200:2, 61865800:2, 61874400:6, 61875400:4, 61882000:2, 61882400:2, 61898000:2, 61902000:2, 61907800:4, 61908400:4, 61942000:2, 61945200:2, 61966600:4, 61998400:4, 62030400:2, 62041000:2, 62046800:2, 62051600:2, 62053400:8, 62064600:2, 62110600:2, 62112800:2, 62145400:4, 62183400:4, 62184800:2, 62187000:10, 62188600:2, 62190600:2, 62192800:4, 62193800:4, 62205400:6, 62569400:2, 62577600:6, 62578800:2, 62587400:2, 62655400:2, 62655800:2, 62656800:2, 62665600:2, 62675600:4, 62677200:2, 62677600:6, 62697800:2, 62698200:4, 62699800:2, 62722600:2, 62917800:2, 62918200:2, 62918600:6, 63023200:2, 63062000:6, 63064800:4; EnhW1: 60937400:2, 61120600:4, 61121200:4, 61192200:6, 61194800:4, 61297400:2, 61322200:2, 61342000:2, 61366000:4, 61383000:8, 61385600:2, 61430200:2, 61438600:6, 61668800:2, 61731600:6, 61751000:4, 61751600:6, 61756400:2, 61791400:2, 61799600:4, 61800600:2, 61814400:2, 61842200:4, 61883800:2, 61889800:6, 61898400:2, 61926600:2, 61946200:2, 61946600:2, 62060600:2, 62127400:2, 62143000:2, 62206600:4, 62241000:2, 62250000:2, 62331600:2, 62333000:2, 62336000:4, 62366200:4, 62371000:6, 62421400:4, 62517400:2, 62580400:2, 62606000:2, 62608000:6, 62705000:2, 62715600:2, 62718800:8, 62822600:6, 63073200:6; EnhW2: 60937600:2, 60989600:2, 60994000:8, 61000600:2, 61075200:2, 61082400:2, 61082800:12, 61088600:8, 61095600:2, 61097400:10, 61120200:4, 61126000:4, 61153000:8, 61192800:16, 61195200:6, 61273200:6, 61297600:4, 61320600:4, 61322400:16, 61341600:4, 61342200:2, 61366400:4, 61383800:2, 61385400:2, 61408000:4, 61409000:2, 61413400:2, 61433600:2, 61434800:6, 61439200:2, 61442000:18, 61510200:6, 61559600:2, 61574200:2, 61577600:4, 61589000:4, 61669000:2, 61754000:24, 61764400:2, 61791000:4, 61791600:14, 61799400:2, 61800800:4, 61814600:4, 61848800:4, 61859800:4, 61881800:2, 61897400:6, 61898200:2, 61902200:4, 61907600:2, 61908800:4, 61944000:12, 61949800:2, 61966400:2, 61990800:6, 61994600:6, 61998800:2, 62029800:6, 62030600:2, 62037400:2, 62040400:6, 62041200:10, 62043600:4, 62046600:2, 62047000:12, 62049600:20, 62065800:2, 62070600:2, 62072200:4, 62074800:6, 62100800:2, 62108800:2, 62110800:2, 62115200:2, 62123200:4, 62137600:2, 62142800:2, 62148600:2, 62150000:4, 62171000:2, 62173600:2, 62176600:4, 62181200:2, 62183200:2, 62184200:6, 62190800:6, 62192600:2, 62203400:2, 62206000:6, 62207000:16, 62225200:2, 62226400:2, 62239000:16, 62249600:4, 62255000:4, 62281400:4, 62296200:14, 62301200:8, 62324200:2, 62333200:2, 62366600:6, 62370800:2, 62371600:4, 62421200:2, 62422400:10, 62424400:6, 62428000:2, 62437600:2, 62517200:2, 62561000:8, 62568200:2, 62572600:4, 62579000:2, 62580600:2, 62605800:2, 62608600:2, 62612400:10, 62665400:2, 62665800:2, 62673000:4, 62679000:6, 62698600:2, 62715200:4, 62716000:8, 62719600:2, 62725400:2, 62734200:10, 62823200:4, 62838200:8, 62900400:6, 62916400:2, 62919200:10, 62935000:8, 63030800:2, 63031800:4, 63061200:2, 63062600:8, 63073000:2, 63073800:2, 63085000:4; EnhAc: 61126600:2, 61142000:2, 61146600:2, 61345000:6, 61378000:6, 61599400:6, 61804600:2, 61823200:16, 61864200:2, 61875800:2, 61882200:2, 61941800:2, 61943000:2, 61967000:8, 62051800:16, 62114400:6, 62205200:2, 62569600:2, 62594400:4, 62676800:4, 62697600:2, 62722400:2, 62788400:8, 62870000:12, 62918000:2, 62918400:2, 62925000:2, 63022000:12; DNase: 60941400:4, 60982600:2, 60994800:2, 61000400:2, 61003600:2, 61033400:2, 61043400:8, 61106200:2, 61135800:2, 61224800:4, 61265800:2, 61268000:4, 61284000:10, 61317000:2, 61340000:4, 61342400:4, 61355400:4, 61368400:6, 61371000:2, 61382200:4, 61382800:2, 61385800:4, 61415200:2, 61427800:4, 61513200:2, 61514800:2, 61517800:4, 61539400:8, 61725200:2, 61753800:2, 61764000:4, 61765800:2, 61769800:2, 61808000:2, 61930000:2, 61931200:4, 61935200:2, 61945600:6, 61947600:2, 61957000:2, 61963800:4, 61968600:2, 62037600:2, 62046400:2, 62058200:2, 62067800:2, 62083000:2, 62094800:2, 62108600:2, 62111000:4, 62123000:2, 62137800:2, 62173400:2, 62177800:2, 62194200:4, 62201400:2, 62212800:4, 62216000:2, 62225400:10, 62241200:6, 62267800:4, 62277600:2, 62281800:4, 62284400:4, 62297600:2, 62309600:2, 62403800:2, 62407000:2, 62414600:2, 62425800:6, 62428200:2, 62499400:2, 62528600:2, 62566800:2, 62580200:2, 62581600:2, 62606200:2, 62607800:2, 62718600:2, 62735400:4, 62738600:2, 62746600:2, 62752400:4, 62756200:2, 62784600:2, 62823600:4, 62841000:4, 62856800:4, 62890200:2, 62913600:2, 62920200:2, 62950400:4, 62975200:2, 63017800:2, 63040000:4, 63043000:4, 63045600:2, 63079200:8, 63081000:2, 63085400:2.

In additional embodiments, one or more agents can be used to modulate one or more gene products of IRX3, IRX5, or ARID5B. Suitable agents include, but are not limited to, a small interfering ribonucleic acid (siRNA), a microRNA (miRNA), an anti-sense ribonucleic acid (antisense RNA), an anti-sense deoxyribonucleic acid (antisense DNA), a long non-coding ribonucleic acid (lncRNA), or an antibody (or antigen binding fragments or conjugates thereof), including fully human or humanized antibodies that modulate the function of IRX3, IRX5, OBE1, ARID5B, or genetic variant rs1421085, or a combination thereof. Such agents are routinely used and known to those of skill in the art. Methods of designing, e.g., siRNA, miRNA, antisense, and antibodies are known and available in the art.

As used herein, the term "nucleic acid" refers to a polymer comprising multiple nucleotide monomers (e.g., ribonucleotide monomers or deoxyribonucleotide monomers). "Nucleic acid" includes, for example, genomic DNA, cDNA, RNA, and DNA-RNA hybrid molecules. Nucleic acid molecules can be naturally occurring, recombinant, or synthetic. In addition, nucleic acid molecules can be single-stranded, double-stranded or triple-stranded. In some embodiments, nucleic acid molecules can be modified. Nucleic acid modifications include, for example, methylation, substitution of one or more of the naturally occurring nucleotides with a nucleotide analog, internucleotide modifications such as uncharged linkages (e.g., methyl phosphonates, phosphotriesters, phosphoamidates, carbamates, and the like), charged linkages (e.g., phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like). "Nucleic acid" does not refer to any particular length of polymer and therefore, can be of substantially any length, typically from about six (6) nucleotides to about $10^9$ nucleotides or larger. In the case of a double-stranded polymer, "nucleic acid" can refer to either or both strands of the molecule.

The term "nucleotide sequence," or "sequence" in reference to a nucleic acid, refers to a contiguous series of nucleotides that are joined by covalent linkages, such as phosphorus linkages (e.g., phosphodiester, alkyl and arylphosphonate, phosphorothioate, phosphotriester bonds), and/or non-phosphorus linkages (e.g., peptide and/or sulfamate bonds).

The terms "nucleotide" and "nucleotide monomer" refer to naturally occurring ribonucleotide or deoxyribonucleotide monomers, as well as non-naturally occurring derivatives and analogs thereof. Accordingly, nucleotides can include, for example, nucleotides comprising naturally occurring bases (e.g., adenosine, thymidine, guanosine, cytidine, uridine, inosine, deoxyadenosine, deoxythymidine, deoxyguanosine, or deoxycytidine) and nucleotides comprising modified bases (e.g., 2-aminoadenosine, 2-thiothymidine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, 2-thiocytidine).

In further embodiments, one or more genome editing systems can be used to modulate one or more genes of IRX3, IRX5, ARID5B, of OBE1, or of the genetic variant rs1421085. Various methods for genome editing are known and available in the art (Gaj et al., Trends Biotech. 31(7): 397-405, 2013), and include, e.g., transcription activator-like effector nucleases (TALEN) and clustered regularly interspaced short palindromic repeat (CRISPR)-associated nuclease (e.g., Cas9) ("CRISPR/Cas9"). In a particular embodiment, the CRISPR/Cas9 system can be used to modulate one or more genes (e.g., genetic variant rs1421085) of the present invention. As those of skill in the art would appreciate, other forms of the CRISPR/Cas system can also be used.

CRISPR together with cas (CRISPR-associated) genes was first identified as an adaptive immune system that provides acquired resistance against invading foreign nucleic acids in bacteria and archaea (Barrangou et al. Science 315:1709-12 (2007)). CRISPR consists of arrays of short conserved repeat sequences interspaced by unique variable DNA sequences of similar size called spacers, which often originate from phage or plasmid DNA (Barrangou et al. *Science* 315:1709-12 (2007); Bolotin et al. *Microbiology* 151:2551-61 (2005); Mojica et al. *J Mol Evol* 60:174-82 (2005)). In its native environment, the CRISPR/Cas system functions by acquiring short pieces of foreign DNA (spacers) which are inserted into the CRISPR region and provide immunity against subsequent exposures to phages and plasmids that carry matching sequences (Barrangou et al. *Science* 315:1709-12 (2007)). The CRISPR/Cas9 system from *Streptococcus pyogenes* was first characterized as involving only a single gene encoding the Cas9 protein and two RNAs—a mature CRISPR RNA (crRNA) and a partially complementary trans-acting RNA (tracrRNA)—which were identified as necessary and sufficient for RNA-guided silencing of foreign DNAs.

Since its discovery, the CRISPR/Cas9 system has been developed to modify or silence various genes of interest in many organisms (see, e.g., WO 2014/018423; WO 2014/011237; WO 2013/176772; and WO 2013/169398). In its most widely used form, Cas9 nuclease is directed by a synthetic guide RNA (sgRNA or guide or guide RNA) to perform site-specific double-strand DNA breaks at a target nucleotide sequence within a gene of interest. Specificity is conferred by homology (or identity) of the sgRNA to the target nucleotide sequence in the genome (Cong, L. et al., *Science* 339, 819-823 (2013); Shalem, O. et al. *Science* 343, 84-87 (2014); Wang, T. et al. *Science* 343, 80-84 (2014)). The break at the target nucleotide sequence is repaired with a repair template, which can be used to insert a desired mutation or sequence into the target site, including tethering a polypeptide to a target site within the genome (the gene). Methods of using the CRISPR/Cas9 system, which comprises the cas enzyme, sgRNA, and repair template, are known in the art. In addition, methods of designing suitable sgRNA sequences are also known.

In another embodiment, the agent is an siRNA that targets the IRX3 gene. Examples of siRNA molecules that target the IRX3 gene are disclosed herein. In various embodiments, the IRX3 siRNA comprises a sequence having at least 90%, 91%, 92%, 93%, 94%, 95%, 96%, 97%, 98%, 99%, or 100% sequence identity to a sequence selected from the group consisting of SEQ ID NOs: 1-18. In a particular embodiment, the method comprises contacting an adipocyte with one or more IRX3 siRNA comprising a sequence selected from the group consisting of SEQ ID NOs: 1-3. In related embodiments, the agent is an miRNA or antisense that targets the IRX3 gene. In other embodiments, the agent is a genome editing system (e.g., CRISPR/Cas9 system) that targets and modifies a sequence in the IRX3 gene.

The term "identity" or "sequence identity" means that two nucleotide or amino acid sequences, when optimally aligned, such as by the programs GAP or BESTFIT using default gap weights, share at least, e.g., 70% sequence identity, or at least 80% sequence identity, or at least 85% sequence identity, or at least 90% sequence identity, or at least 95% sequence identity or more. For sequence comparison, typically one sequence acts as a reference sequence (e.g., parent sequence), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., *Current Protocols in Molecular Biology*). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

As used herein, "contacting" refers to any one or more known methods of introducing an agent to, e.g., a cell (e.g., adipocyte). For example, various transfection methods for introducing nucleic acid agents (e.g., siRNA or components of the CRISPR/Cas9 system) are known in the art. In some embodiments, the term "contacting" can be used synonymously with, e.g., "introducing" or "transfecting." For example, the one or more agents can be introduced into a cell by viral delivery including retrovirus, adenovirus, lentivirus, herpes simplex virus, vaccinia, and adeno-associated virus. In further examples, the one or more agents can be introduced by one or more of injection of naked DNA, electropermeabilization (e.g., electroporation), a biolistic particle delivery system (e.g., gene gun), cellular sonication (sonoporation), magnetic field-based transfection (magnetifection), and may further include use of oligonucleotides, lipoplexes, dendrimers, and inorganic nanoparticles.

In further embodiments, the agent is an siRNA that targets the IRX5 gene. Examples of siRNA molecules that target the IRX5 gene are disclosed herein. In various embodiments, the IRX5 siRNA comprises a sequence having at least 90%, 91%, 92%, 93%, 94%, 95%, 96%, 97%, 98%, 99%, or 100% sequence identity to a sequence selected from the group consisting of SEQ ID NOs: 19-26. In a particular embodiment, the method comprises contacting an adipocyte with one or more IRX5 siRNAs comprising a sequence selected from the group consisting of SEQ ID NOs: 19-21. In related embodiments, the agent is an miRNA or an antisense that targets the IRX5 gene. In other embodiments, the agent is a genome editing system (e.g., CRISPR/Cas9 system) that modifies a target sequence in the IRX5 gene.

In additional embodiments, the agent is an siRNA that targets the ARID5B gene. In various embodiments, the ARID5B siRNA comprises a sequence having at least 90%, 91%, 92%, 93%, 94%, 95%, 96%, 97%, 98%, 99%, or 100% sequence identity to a sequence selected from the group consisting of SEQ ID NOs: 34-44. In a particular embodiment, the method comprises contacting an adipocyte with one or more ARID5B siRNAs comprising a sequence selected from the group consisting of SEQ ID NOs: 37, 40 and 41. In related embodiments, the agent is an miRNA or antisense that targets the ARID5B gene. In other embodiments, the agent is a genome editing system (e.g., CRISPR/Cas9 system) that modifies a target sequence in the IRX5 gene.

In some embodiments, the agent targets the genetic variant rs1421085. In one embodiment, the agent is a CRISPR system (e.g., CRISP/Cas9) that comprises one or more sgRNAs that targets and modifies the genetic variant rs1421085. For example, the sgRNA targets and modifies T<-->C or TT<-->CC of the genetic variant rs1421085. In certain embodiments, the sgRNA that targets rs1421085 comprises the sequence set forth in SEQ ID NO: 27 or SEQ ID NO: 28. In other embodiments, the agent can include a cis-acting accessible DNA elements in OBE1 region. Examples of cis-acting enhancers or repressors in OBE1 region include, in order of predicted regulatory score indicated by starting positions (length), e.g., 54753888(864), 54114455(470), 53532966(268), 53929676(606), 55073418 (381), 54916234(821), 54288117(537), 55306066(379), 53802191(858), 53861576(569), 53878805(307), 53516100 (308), 54880622(1046), 53812975(607), 53850858(1276), 55185474(736), 53946082(539), 53728960(359), 53698614 (682), 55317851(638), 54480516(433), 53810039(361), 53766333(582), 54459432(1306), 53843094(522), 54000719(918), 55150416(386), 54200277(439), 53826439 (328), 54365092(580), 53930615(615), 55111152(326), 54691253(370), 55020391(326), 53906686(372), 53947053 (304), 54061028(360), 54496022(562), 53957870(786), 54482028(274), 53561165(273), 54040664(280), 54106189 (419), 54636584(388), 54493831(369), 53928066(242), 54397415(771), 55201565(624), 54436220(372), 54951064 (615), 55069840(481), 53980742(421), 53583843(454), 54681098(1874), 54539495(344), 54907084(234), 54157527(679), 54537370(355), 54691713(234), 55213727 (563), 55035867(302), 53818134(392), 54008637(424), 53956746(786), 54502867(722), 53779017(403), 53855335 (1008), 54389161(389), 53807161(265), 53633923(504), 53839115(261), 54018845(397), 55178568(344), 53915264 (340), 53848546(692), 55314488(407), 54111297(424), 53938275(704), 53747701(1335), 54516639(2369), 53823122(311), 54507279(472), 54683884(244), 54150030 (600), 54403771(302), 54300392(437), 54487817(329), 55010435(1134), 53850113(480), 53592597(815), 53787306(480), 53790545(338), 55071019(248), 55297845 (396), 54456107(281), 55170345(299), 53579310(406), 54856384(622), 54212130(766), 53789455(231), 53873004 (407), 54980663(735), 54186156(994), 54032928(347), 53700717(658), 54560891(310), 53790313(229), 53899316 (379), 54523143(553), 54250196(299), 54494499(172), 54205965(476), 54376201(1049), 54907633(320), 54005525(500), 53949471(570), 55283946(225), 54408497 (1055), 54276131(311), 53563479(357), 53815168(264), 54956824(540), 54169694(767), 54896259(586), 54616543 (306), 54537022(242), 54527058(221), 53580918(282), 53568872(372), 54441640(226), 54381904(320), 55055491 (472), 55307989(414), 53545138(369), 54089706(381), 54352892(311), 53926081(272), 54955394(226), 54149509 (419), 54540040(1371), 53779557(624), 54689955(410), 53549219(302), 55218065(293), 53898812(276), 53944849 (950), 54025684(403), 54127331(589), 55331728(282), 54545025(592), 54273322(477), 53977986(314), 53773816 (372), 54250552(450), 54580352(434), 53760417(445), 55115832(196), 54209482(531), 53666475(893), 53956066 (224), 55328821(339), 54664232(411), 55008320(246), 53747400(284), 54083461(478), 53992468(270), 53543910 (843), 53778411(273), 54273892(997), 54599679(645), 53969984(810), 53995005(276), 55180872(393), 53775550 (437), 54002346(382), 53965810(151), 54100373(573), 53714784(321), 54302378(200), 54159114(254), 54619978 (205), 53958992(353), 54537839(940), 53712586(316), 53800693(200), 54006929(459), 54174472(198), 54385133 (393), 54089160(345), 55331069(333), 55096459(221), 53541692(380), 54019857(525), 54839799(215), 54194954 (887), 54311775(842), 54067785(140), 54033787(271), 54152881(187), 53839440(683), 53863158(262), 54542454 (257), 53983325(680), 53595053(345), 54602880(359), 54978066(119), 54159817(184), 53702849(225), 55070398 (392), 54107242(352), 53819070(202), 55336545(342), 54400930(371), 54711339(454), 53970988(1067), 54065362(271), 54434209(258), 54393018(353), 53986327 (311), 53805702(177), 53816217(562), 53809129(541), 54360254(216), 54016575(387), 54457883(428), 54084222 (733), 55034585(248), 53803703(306), 55154389(210), 53897402(122), 53660758(467), 53996062(157), 55019702 (229), 53632541(265), 54097036(325), 54211486(587), 54471368(222), 53723614(285), 53857115(282), 54851544 (165), 54096292(426), 54359582(276), 54666413(501), 53751627(149), 53569965(403), 54724298(191), 55112991 (377), 53933033(134), 53875728(483), 54299546(532), 54314822(178), 54667892(268), 53553711(358), 53575300 (254), 55160502(124), 54456436(473), 54465961(115), 54509263(157), 53795985(196), 54723379(384), 53979947 (156), 54101149(336), 53837458(386), 55152559(463), 53534768(208), 53883499(283), 53777131(138), 53947945 (184), 54618989(659), 53786501(284), 54439407(383), 54061470(231), 54060455(456), 54877356(232), 54242136 (386), 53807711(375), 55149989(106), 54957901(599), 53852188(195), 53871456(230), 53814008(225), 54233481

(371), 53685332(244), 54985708(121), 55276482(373), 54533402(274), 53774359(401), 53804627(309), 54687018 (151), 54508761(170), 53874484(215), 54104575(548), 54101530(289), 54002066(250), 53631806(268), 54025084 (405), 53987440(69), 55282447(326), 54852004(434), 54909458(261), 54724741(123), 54002941(160), 55326331 (452), 54083102(142), 54543393(337), 55299484(169), 53600792(254), 53926507(487), 54490231(199), 55104766 (394), 54527289(702), 54395722(388), 54022970(185), 54269154(431), 54275650(187), 53821414(197), 55096910 (351), 53933413(308), 54378587(197), 54665785(180), 53795226(189), 53798094(193), 54721002(156), 55171527 (196), 53916341(113), 54204824(231), 54301995(207), 53523783(226), 55274854(296), 54611495(460), 54249469 (276), 54957505(285), 54396629(343), 55181699(261), 53510097(102), 54068752(128), 54160948(203), 53805898 (185), 54088463(187), 53986925(84), 54160058(555), 55179730(264), 53983073(164), 54162878(222), 54176925 (154), 53954737(538), 53665626(276), 53775040(365), 54088001(131), 54480210(202), 53863756(144), 53803457 (122), 55013374(78), 53860473(474), 54177927(228), 54354910(337), 54095652(339), 53750077(277), 53706408 (229), 54210878(155), 54087837(76), 54115216(495), 53947453(229), 55223266(54), 54093459(208), 54233949 (134), 55135037(98), 54152036(162), 55176474(122), 53713036(140), 53514438(144), 54459132(177), 54390407 (148), 54146491(99), 53815472(102) In another embodiment, the agent can include a trans-acting activator or repressor protein of OBE1 and of the genetic variant rs1421085 (e.g., ARID5B).

In other embodiments, the agent targets and modifies (e.g., inhibits or enhances) one or more epigenomic region (e.g., a promoter or distal enhancer) of a gene. For example, the agent is one or more sgRNA that targets, e.g., a promoter, distal enhancer, or both, of the IRX3, IRX5, or ARID5B gene. In other embodiments, the agent is a chemical compound that modifies one or more epigenomic region.

As those of skill in the art will appreciate, any one or more of the target genes can be manipulated to produce either an anti-cachectic or anti-obesity effect. The table below (Table 1) provides non-limiting examples of target manipulation to achieve an anti-cachectic or anti-obesity effect. The manipulations indicated in Table 1 can be combined in any combination to produce the desired effect.

TABLE 1

Manipulation Table

| Target | Manipulation | Mechanism Details | Effect | Direction of Effect |
| --- | --- | --- | --- | --- |
| ARID5B | Knock-down | siRNA, risk & non-risk patients | Increased FTO enhancer activity, increased IRX3/IRX5 in non-risk allele carriers | Obesity |
| ARID5B | Knock-down | siRNA, risk & non-risk patients | Decreased oxygen consumption and glycerol release in in non-risk allele carriers | Obesity |
| IRX3 | Knock-down | siRNA in risk & non-risk patients | Increased oxygen consumption | Anti-obesity |
| IRX5 | Knock-down | siRNA in risk & non-risk patients | Increased oxygen consumption | Anti-obesity |
| IRX3 | Over-expression | Plasmid, ME3 beige adipocytes containing human IRX3 | UCP1 reduction | Obesity |
| IRX5 | Over-expression | Plasmid, ME3 beige adipocytes containing human IRX5 | UCP1 reduction | Obesity |
| IRX3 | Repression | Adipose dominant negative, mouse | Fat mass ratio 60% reduction, resistance to high-fat diet, increased energy dissipation, size reduction of all fat stores, fat cell size reduction in all stores, increased UCP1 | Anti-obesity |
| IRX3 | Repression | Adipose dominant negative, mouse | No weight gain in high-fat, reduced fat stores, reduced fat weight, increased lean mass percentage, increased appetite as body weight percentage, no change in activity, increased lipid catabolism, decreased lipid storage | Anti-obesity |
| IRX3/5 | Knock-out | Double knock-out, MEF-derived adipocytes | Reduced lipid cells, reduced lipid anabolism, reduced lipid accumulation | Anti-obesity |
| IRX3 | Over-expression | Double knock-out, MEF-derived adipocytes | Increased lipid accumulation, increased lipid expression, increased fat cell size | Obesity |

TABLE 1-continued

Manipulation Table

| Target | Manipulation | Mechanism Details | Effect | Direction of Effect |
|---|---|---|---|---|
| IRX5 | Over-expression | Double knock-out, MEF-derived adipocytes | Increased lipid accumulation, increased lipid expression, increased fat cell size | Obesity |
| rs1421085 | T-->C | from non-risk to risk individuals | Enhancer activity in adipocytes | Obesity |
| rs1421085 | T<-->C | non-risk <--> risk individuals | Enhancer inactive <--> Enhancer active | Anti-obesity <--> Obesity |
| rs1421085 | T<-->C | non-risk <--> risk individuals | Mitochondrial function: high <--> low | Anti-obesity <--> Obesity |
| rs1421085 | T<-->C | non-risk <--> risk individuals | Lipid catabolism: high <--> low | Anti-obesity <--> Obesity |
| rs1421085 | T<-->C | non-risk <--> risk individuals | Lipid anabolism: low <--> high | Anti-obesity <--> Obesity |
| rs1421085 | TT-->CC | CRISPR/Cas9 non-risk --> risk | IRX3, IRX5 expression increase | Obesity |
| rs1421085 | TT-->CC-->TT | CRISPR/Cas9 non-risk --> risk --> non-risk | IRX3, IRX5 expression increase --> then decrease back | --> Obesity--> Anti-obesity |
| rs1421085 | CC-->TT | CRISPR/Cas9 rescue risk --> non-risk | IRX3, IRX5 repression | Anti-obesity |
| rs1421085 | CC-->TT | CRISPR/Cas9 rescue risk --> non-risk | IRX3, IRX5 repression in early adipocyte differentiation | Anti-obesity |
| rs1421085 | CC-->TT | CRISPR/Cas9 rescue risk --> non-risk | Increased mitochondrial activity and biogenesis | Anti-obesity |
| rs1421085 | CC-->TT | CRISPR/Cas9 rescue risk --> non-risk | Increased oxygen consumption | Anti-obesity |
| rs1421085 | CC-->TT | CRISPR/Cas9 rescue risk --> non-risk | Reduced lipid storage, increased lipid catabolism | Anti-obesity |

In further embodiments, the agent is a dominant negative construct that targets the IRX3 gene, IRX5 gene, or ARID5B gene.

As understood by those of skill in the art, a "dominant negative" is used to denote a class of naturally or non-naturally occurring mutations to genomic DNA that result in an altered gene product that acts antagonistically to the "normal" or typical form of the gene. Dominant negative mutations frequently result in an altered molecular function and are characterized by a dominant phenotype.

As will be appreciated by those of skill in the art, the present methods can be manipulated for either an anti-cachectic or an anti-obesity effect to achieve a benefit therapeutically. For example, the compositions and methods of the present invention can be used to treat obesity (e.g., anti-obesity effect) or to treat cachexia (e.g., to promote an anti-cachectic effect), as described herein. Accordingly, in other aspects, the present invention provides a method of treating a disorder in a patient in need thereof, comprising administering an effective amount of one or more agents that modulate one or more of IRX3, IRX5, ARID5B, genetic variant rs1421085, and OBE1 function, wherein the disorder is mediated by (e.g., caused by, or persists as a result of) dysregulation of thermogenesis in an adipocyte. In certain embodiments, the method comprises administering an effective amount of two or more agents that modulate two or more of IRX3, IRX5, ARID5B, genetic variant rs1421085, and OBE1 function.

As used herein, "treat," "treating," "treatment," and the like refer to reducing, ameliorating, or delaying a disorder mediated by a dysregulation of the thermogenesis pathway.

As will be appreciated by those of skill in the relevant art, treating a disorder mediated by a dysregulation of the thermogenesis pathway does not require that the disorder be completely eliminated. Thus, a treatment is not necessarily curative, and may reduce the effect of a disorder mediated by the thermogenesis pathway by a certain percentage over an untreated disorder mediated by a dysregulation of the thermogenesis pathway. In particular embodiments, the percentage reduction or diminution can be from 10% up to 20, 30, 40, 50, 60, 70, 80, 90, 95, 99 or 100%.

In certain embodiments, "treating" also encompasses preventing a disorder mediated by a dysregulation of the thermogenesis pathway. As used herein, "preventing" refers to reducing the probability of developing a disorder mediated by a dysregulation in the thermogenesis pathway in a patient who may not have the disorder, but may be at risk or may have a genetic predisposition to developing such a disorder. As used herein, "at risk," "susceptible to," or "having a genetic predisposition to," refers to having a propensity to develop a disorder mediated by a dysregulation in the thermogenesis pathway. For example, a patient having a genetic mutation in a gene associated with a disorder mediated by a dysregulation in the thermogenesis pathway has increased risk (e.g., "higher predisposition") of developing the disorder relative to a control subject having a "lower predisposition" (e.g., a patient without a genetic mutation in a gene associated with a disorder mediated by a dysregulation in the thermogenesis pathway. In certain embodiments, a gene associated with the disorder is, e.g., IRX3, IRX5, ARID5B, OBE1, or genetic variant rs1421085.

As used herein, a "dysregulation" of the thermogenesis pathway refers to a change or the presence of a risk allele in one or more of the genes and/or proteins within the network of genes and proteins that regulate or maintain thermogenesis (the "thermogenesis circuitry") that leads or has the potential to lead to a negative or undesirable consequence (e.g., obesity or cachexia). In some embodiments, the negative or undesirable consequence is a result of a change in the function of one or more of IRX3, IRX5, ARID5B, or genetic variant rs1421085. As used herein, the "disorder" refers to a disorder mediated by a dysregulation as defined herein. In some embodiments, the dysregulation is a result of a change in the gene or gene product of one or more of IRX3, IRX5, ARID5B, and genetic variant rs1420185.

In certain embodiments, the disorder includes, e.g., obesity, cardiovascular disease, type 2 diabetes, high blood pressure, stroke, abnormal blood fats, osteoarthritis, sleep apnea, obesity hypoventilation syndrome, or metabolic syndrome. In some embodiments, the disorder includes, e.g., cancer, cachexia, heart failure, kidney failure, physical incapacitation, thrombocytosis, heart arrhythmia, endocrine disorders including hypothyroidism, or opportunistic infections. "Obesity" as used herein refers to clinical obesity, as defined by the World Health Organization (WHO), and includes a BMI of, e.g., greater than 25 kg/m$^2$. In certain embodiments, obesity refers to a BMI of greater than 30 kg/m$^2$. The terms "cachexia" and "wasting syndrome" are used interchangeably. In further embodiments, the cachexia is cachexia associated with cancer, infectious diseases (e.g., AIDS and tuberculosis), chronic obstructive lung disease, autoimmune disorders (e.g., multiple sclerosis), congestive heart failure, familial amyloid polyneuropathy, gadolinium poisoning, mercury poisoning, or hormonal deficiency.

In further aspects, the present invention also provides a method of modulating energy consumption (e.g., thermogenesis) in a cell (e.g., adipocyte), comprising contacting the cell with an effective amount of a genome editing system that modifies genetic variant rs1421085.

In particular embodiments, the genome editing system is a CRISPR/Cas9 system. In one embodiment, the CRISPR/Cas9 system comprises a synthetic guide RNA (sgRNA) comprising the sequence set forth in SEQ ID NO: 27 or SEQ ID NO: 28. For example, the sgRNA targets and modifies T<-->C or TT<-->CC of the genetic variant rs1421085.

In additional embodiments, the cell is an adipocyte, as described herein.

In various embodiments, the one or more agents are administered to a cell, a tissue, or a patient as a pharmaceutical composition, as described herein.

As used herein, "a patient in need thereof" refers to any human subject receiving or who may receive medical treatment, in need of treatment, or desires treatment—e.g., voluntary weight loss. Therefore, in one embodiment, a patient in need thereof includes a patient desiring weight loss.

As used herein, a "therapeutically effective amount" refers to the amount of an agent or composition required to improve, inhibit, or ameliorate a condition of a patient, or a symptom of a disorder, in a clinically relevant manner. Any improvement in the patient is considered sufficient to achieve treatment. As those of skill in the art will appreciate, a sufficient amount of an active agent used to practice the present invention for the treatment of a disorder mediated by a dysregulation of the thermogenesis pathway will vary depending upon, e.g., the manner of administration, the age, body weight, genotype, and general health of the patient. Moreover, an effective amount will also depend upon whether an agent is administered as the sole therapeutic agent, or in combination with another agent of the present invention (as described herein), or in combination with other therapeutics known to have a beneficial effect on the disorder. Ultimately, the prescribers or researchers will decide the appropriate amount and dosage regimen. Such determinations are routine to those of skill in the art.

Various therapeutics (additional therapeutic agents) beneficial for the disorders disclosed herein are known, and can be used in combination with any one or more of the agents described herein. From a therapeutic perspective, antihypertensives (such as diuretic medicines, beta-blocking agents, calcium-channel blockers, renin-angiotensin system agents), lipid-modifying medicines, nitrates, and antiarrhythmic medicines are considered strong candidates for a disorder mediated by a dysregulation of the thermogenesis pathway. Further aspects of the invention relate to the administration of antihypertensives (such as diuretic medicines, beta-blocking agents, calcium-channel blockers, renin-angiotensin system agents), lipid-modifying medicines, nitrates, and antiarrhythmic medicines separately to individuals in need thereof that may also possess different gene variants associated with a favorable response to each type of administration.

In other embodiments, treatment of the disorder may also include administration of, e.g., aspirin, statins and/or epigenetic modifiers. The epigenetic modifiers may be non-specific DNA synthesis inhibitors, such as DNA methyltransferase inhibitors (such as, but not limited to 5-aza-2'-deoxycytidine or 5-azacytidine) or histone deacetylase inhibitors (such as varinostat, romidepsin, panobinostat, belinostat and entinostat).

In related embodiments, the additional therapeutic agent can be administered before, simultaneously with, or after the administration of a composition comprising one or more agent of the present invention. Accordingly, a composition of the present invention and an additional therapeutic agent can be administered together in a single formulation (e.g., a tablet, capsule, powder, injectable liquid, etc.), or can be administered in separate formulations, e.g., either simultaneously or sequentially, or both. The duration of time between the administration of a composition of the present invention and one or more additional therapeutic agents will depend on the nature of the therapeutic agent(s). In addition, a composition of the present invention and the additional therapeutic agent(s) may or may not be administered on similar dosing schedules. For example, one or more agents of a composition of the present invention and the additional therapeutic agent may have different half-lives and/or act on different time-scales such that the composition of the present invention is administered with greater frequency than the additional therapeutic agent, or vice-versa. The number of days in between administration of therapeutic agents can be appropriately determined by persons of ordinary skill in the art according to the safety and pharmacodynamics of each drug.

As described herein, therapy or treatment according to the invention may be performed alone or in conjunction with another therapy (e.g., adjuvant therapy), and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of the disorder, and how the patient responds to the treatment. Additionally, a patient having a greater risk of developing the disorder can receive prophylactic treatment to inhibit or delay symptoms of the disorder.

In related aspects, the present invention also provides compositions, e.g., pharmaceutical compositions, comprising an effective amount of one or more agents that modulate the function of one or more of IRX3, IRX5, ARID5B, OBE1, or genetic variant rs1421085 in an adipocyte. In another embodiment, the pharmaceutical composition comprises two or more agents that modulate the function of two or more of IRX3, IRX5, ARID5B, OBE1, or genetic variant rs1421085 in an adipocyte. In other embodiments, the pharmaceutical composition comprises three or more agents that modulate the function of three or more of IRX3, IRX5, ARID5B, OBE1, or genetic variant rs1421085 in an adipocyte. In further embodiments, the pharmaceutical composition comprises four or more agents that modulate the function of IRX3, IRX5, ARID5B, OBE1, and genetic variant rs1421085 in an adipocyte. In additional embodiments, the pharmaceutical composition comprises one or more agents that modulate the function of one, two, three, or all of IRX3, IRX5, ARID5B, OBE1, and genetic variant rs1421085 in an adipocyte.

In related embodiments, the pharmaceutical composition further comprises one or more pharmaceutically acceptable excipients, vehicles diluents, stabilizers, preservatives, solubilizers, emulsifiers, adjuvants and/or carriers. For example, such pharmaceutical compositions can include diluents of various buffer content (e.g., Tris-HCl, phosphate), pH and ionic strength; additives such as detergents and solubilizing agents (e.g., Polysorbate 20, Polysorbate 80), anti-oxidants (e.g., ascorbic acid, sodium metabisulfite), preservatives (e.g., Thimerosol, benzyl alcohol) and bulking substances (e.g., lactose, mannitol). The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York. See also, e.g., *Remington's Pharmaceutical Sciences*, 18th Edition (1990, Mack Publishing Co., Easton, Pa.) pages 1435:1712, incorporated by reference herein.

Depending on the intended mode of administration, the pharmaceutical formulations can be in a solid, semi-solid, or liquid dosage form, such as, for example, tablets, pills, capsules, microspheres, powders, liquids, suspensions, emulsions, solutions, gels including hydrogels, pastes, ointments, creams, plasters, drenches, delivery devices, suppositories, enemas, injectables, implants, sprays, or aerosols or the like, possibly contained within an artificial membrane, preferably in unit dosage form suitable for single administration of a precise dosage.

Administration of pharmaceutical compositions according to the methods of the present invention may be by any suitable means that results in a compound concentration that is effective for treating or inhibiting (e.g., by delaying) the development of the disorder. The agent is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The composition may be provided in a dosage form that is suitable for parenteral or non-parenteral administration, e.g., oral, rectal, intravenous, intramuscular, subcutaneous, inhalation, nasal, topical, transdermal, or ophthalmic administration.

Energy Consumption Pathway in Diagnostics

In further aspects, the present invention provides a method for identifying and selecting a subject with increased risk of developing a disorder mediated by a dysregulation of the energy consumption (e.g., thermogenesis) pathway, comprising the steps of: (a) sequencing at least part of a genome comprising one or more genes selected from the group consisting of ARID5B, OBE1, rs1421085, IRX3 and IRX5 or a downstream target thereof, in a cell of the subject, and (b) identifying from said sequencing one or more alleles in one or more genes selected from the group consisting of ARID5B, rs1421085, OBE1, IRX3 and IRX5 or a downstream target thereof, wherein presence of one or more risk alleles indicates an increased risk of developing a disorder mediated by a dysregulation of the energy consumption (e.g., thermogenesis) pathway. For example, the presence of the obesity-risk allele C in rs1421085 (CC in homozygous individuals) indicates that the subject is at risk of developing obesity. In another example, the presence of the obesity protective allele (also referred to as the cachexia-risk allele) TT in rs1421085 indicates that the subject is at risk of developing cachexia, if also diagnosed with a disease as described herein (e.g., cancer, tuberculosis, multiple sclerosis, AIDS).

In certain embodiments, the cell is obtained from a sample of the subject, e.g., tissue (e.g., blood) sample. In one embodiment, the subject is a human subject.

In additional embodiments, the part of the genome is an exome. In various embodiments, the sequencing is whole exome sequencing (WES).

In other aspects, the present invention also provides a method for identifying and selecting a subject with an increased risk of developing a disorder mediated by a dysregulation of the energy consumption (e.g., thermogenesis) pathway and providing a personalized medicine method, said method comprising the steps of: (a) sequencing at least part of a genome comprising one or more genes selected from the group consisting of ARID5B, rs1421085, OBE1, IRX3 and IRX5 or a downstream target thereof of one or more cells in a blood sample of the subject, (b) identifying from said sequencing one or more mutations in one or more genes selected from the group consisting of ARID5B, rs1421085, O B E 1, IRX3 and IRX5 or a downstream target thereof, wherein presence of said mutation(s) indicates an increased risk of developing a disease involving an adipose regulatory pathway, and (c) initiating a treatment or monitoring regimen to suppress said mutation(s) or their effects in the subject, thereby decreasing risk of developing a disorder mediated by a dysregulation of the energy consumption (e.g., thermogenesis) pathway. In certain embodiments, the treatment relates to a method of genome editing (e.g., CRISPR/Cas).

In some embodiments, the one or more mutations are any one or more of frameshift mutations, nonsense mutations, missense mutations or splice-site variant mutations.

In additional embodiments, the part of the genome is an exome. In various embodiments, the sequencing is whole exome sequencing (WES). In another aspect, the present invention provides a method of identifying a patient with increased risk of developing a disorder associated with dysregulation of energy consumption in an adipocyte, the method comprising: a) sequence or genotyping at least part of a genome comprising IRX3, IRX5, ARID5B, OBE1, genetic variant rs1421085, or a combination thereof, in a sample from the patient; and b) identifying from said sequence or genotyping one or more mutations in at least part of a genome comprising IRX3, IRX5, ARID5B, OBE1, genetic variant rs1421085, or a combination thereof wherein the presence of one or more mutation indicates that the patient has an increased risk of developing a disorder associated with dysregulation of energy consumption in an adipocyte.

In some embodiments, the disorder is obesity, cardiovascular disease, or type 2 diabetes. In certain embodiments, the disorder is associated with one or more mutations that confer increased function or one or more of IRX3, IRX5, OBE1, and genetic variant rs1421085, as described herein. For example, increased function can include increased expression of IRX3 and/or IRX5, or enhanced functional activity of IRX3 or IRX5. In some embodiments, the disorder is associated with one or more mutations that confer decreased activity of ARID5B (e.g., decreased expression or decreased binding ability to rs1421085).

In some embodiments, the method identifies a cancer patient who may be at risk of developing cachexia. In certain embodiments, the disorder is associated with one or more mutations that confer decreased function of IRX3, IRX5, or OBE1, or a combination thereof. For example, a decreased function of IRX3 can be decreased expression or an inactive form of IRX3 that does not have function (e.g., misfolded IRX3). Decreased function of OBE1 includes, e.g., a decreased ability for this region to bind to an enhancer. In some embodiments, the disorder is associated with one or more mutations that confer increased function of ARID5B (e.g., increased expression or enhanced binding ability to rs1421085).

In further aspects, the present invention also provides a method of identifying a patient with increased risk of developing a disorder associated with dysregulation of energy consumption in an adipocyte, the method comprising: a) measuring an expression level of IRX3, IRX5, or ARID5B, or a combination thereof, in a sample from the patient; and b) comparing the expression level measured in step a) with a control level of IRX3, IRX5, or ARID5B, or a combination thereof wherein an increase or decrease in the measured level as compared to the control level indicates that the patient has an increased risk of developing a disorder associated with dysregulation of energy consumption in an adipocyte.

In some embodiments, the disorder is obesity, cardiovascular disease, or type 2 diabetes, wherein IRX3 function is increased, IRX5 function is increased, OBE1 function is increased, or ARID5B function is decreased, or a combination thereof.

In other embodiments, the disorder is cachexia, wherein IRX3 function is decreased, IRX5 function is decreased, OBE1 function is decreased, or ARID5B function is increased, or a combination thereof.

In some embodiments, the methods described herein further comprise determining a method of treatment after identifying that a patient has an increased risk of developing, e.g., obesity. For example, if it is determined that the patient has the T to C variant at rs1421085, or has increased expression of IRX3 and/or IRX5, then it is desirable to treat the patient with one or more agents as described herein to modulate energy consumption to enhance energy dissipation. Alternatively, if it is determined that the patient does not have the T to C obesity risk allele, or a mutation that otherwise indicates the patient is not at risk of developing, e.g., obesity, as described herein, then a medical professional may choose to treat the patient using alternative anti-obesity therapeutics.

In another aspect, the present invention provides a method of evaluating the efficacy of a treatment in a patient undergoing treatment for a disorder mediated by a dysregulation of energy consumption, the method comprising: a) measuring an expression level of IRX3. IRX5, or ARID5B, or a combination thereof in a first sample from the patient; b) administering an agent that modulates energy consumption in an adipocyte of said patient; and c) subsequently measuring an expression level of IRX3, IRX5, or ARID5B, or a combination thereof in a second sample from the patient; wherein a decrease in IRX3, decrease in IRX5, or increase in ARID5B, or combination thereof in the second sample relative to the first sample indicates that the treatment is effective. In a related embodiment, the disorder is obesity, cardiovascular disease, type 2 diabetes, high blood pressure, stroke, abnormal blood fats, or metabolic syndrome.

In further aspects, the present invention provides a method of evaluating the efficacy of a treatment in a patient undergoing treatment for a disorder mediated by a dysregulation of energy consumption, the method comprising: a) measuring an expression level of IRX3, IRX5, or ARID5B, or a combination thereof in a first sample from the patient; b) administering an agent that modulates energy consumption in an adipocyte of said patient; and c) subsequently measuring an expression level of IRX3, IRX5, or ARID5B, or a combination thereof in a second sample from the patient; wherein an increase in IRX3, increase in IRX5, or decrease in ARID5B, or combination thereof in the second sample relative to the first sample indicates that the treatment is effective. In a related embodiment, the disorder is cancer, cachexia, heart failure, kidney failure, physical incapacitation, thrombocytosis, heart arrhythmia, or opportunistic infection.

In other aspects, the present invention also provides a method of identifying a cancer patient with increased risk of developing cachexia, the method comprising: a) sequencing at least part of a genome comprising a genetic variant rs1421085 in a sample from the patient; and b) detecting presence of a thymine or an adenine at genetic variant rs142105; wherein the presence of a thymine indicates that the cancer patient has an increased risk of developing cachexia.

In further aspects, the present invention provides kits useful for screening nucleic acids isolated from one or more subjects for any of the mutations (e.g., somatic mutations) described herein, and instructions for using the kit to detect variation in the nucleotide corresponding to one or more of the mutations, such as, e.g., one or more genes selected from the group consisting of ARID5B, rs1421085, OBE1, IRX3 and IRX5 or a downstream target thereof, of the isolated nucleic acid.

To determine the genotype of a subject according to the methods of the present invention, a sample of genomic DNA is obtained from the subject. That sample of genomic DNA may be obtained from a sample of tissue or cells taken from the subject. The tissue sample includes, but is not limited to, hair (including roots), skin, buccal swabs, blood, or saliva. The amount/size of sample required is known to those skilled in the art.

Methods of nucleic acid (e.g., DNA) isolation are known in the art. See, e.g., U.S. Pat. Nos. 6,548,256 and 5,989,431. DNA may be extracted from a patient specimen using any other suitable methods known in the art.

Methods for determining the genotype of a patient and for identifying or analyzing whether a given DNA sample contains a particular somatic mutation are known in the art. Any method for determining genotype can be used for determining genotypes in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, nucleic acid hybridization, polymerase chain reaction (PCR), RFLP analysis and size chromatography (e.g., capillary or gel chromatography), all of which are known and available to one of skill in the art.

The methods of the present invention, such as whole exome sequencing and targeted amplicon sequencing, have commercial applications in diagnostic kits for the detection of the somatic mutations in patients. A test kit according to the invention may comprise any of the materials necessary for whole exome sequencing and targeted amplicon sequencing, for example. In one embodiment, a diagnostic for the present invention may comprise testing for any of the genes disclosed herein. The kit further comprises additional means, such as reagents, for detecting or measuring the sequences of the present invention, as well as a positive and negative control.

Identifying Compounds that Modulate the Energy Consumption Pathway

In further aspects, the present invention is directed to a method of identifying therapeutic agents that can modulate the energy consumption (e.g., thermogenesis) pathway and that have anti-obesity or anti-cachectic effects.

In further aspects, the present invention also relates to identifying molecules (e.g., therapeutics), advantageously small molecules or biologics, that have anti-obesity or anti-cachectic effects by modulating one or more of the genes or proteins including ARID5B, rs1421085, OBE1, IRX3 and IRX5, their upstream regulators, and their downstream targets. The invention contemplates screening libraries of small molecules or biologics (e.g., antibodies or RNAs) to identify compounds involved in suppressing or inhibiting expression of somatic mutations or alter the cells phenotypically so that the cells with mutations behave more normally in one or more of ARID5B, rs1421085, IRX3 and IRX5 or a downstream target thereof.

High-throughput screening (HTS) can be used for identifying small molecules or biologics involved in suppressing or inhibiting expression of somatic mutations in one or more of ARID5B, rs1421085, IRX3 and IRX5 or a downstream target thereof. The flexibility of the process has allowed disparate areas of biology to engage with an equally diverse palate of chemistry (see, e.g., Inglese et al., Nature Chemical Biology 3, 438-441 (2007)). Diverse sets of chemical libraries, containing more than 200,000 unique small molecules, as well as natural product libraries, can be screened. This includes, for example, the Prestwick library (1,120 chemicals) of off-patent compounds selected for structural diversity, collective coverage of multiple therapeutic areas, and known safety and bioavailability in humans, as well as the NINDS Custom Collection 2 consisting of a 1,040 compound-library of mostly FDA-approved drugs (see, e.g., U.S. Pat. No. 8,557,746). Thus, in one aspect, the present invention provides a method of identifying an agent that modulates energy consumption in an adipocyte, said method comprising: a) measuring a first expression level of IRX3, IRX5, or ARID5B, or a combination thereof, in an adipocyte sample; b) contacting the sample with a candidate agent; and c) measuring a second expression level of IRX3, IRX5, or ARID5B, or a combination thereof, in the sample; wherein an increase or decrease in the second expression level as compared to the first expression level indicates that the candidate agent is an agent that modulates energy consumption in an adipocyte. In a related embodiment, the candidate agent can be, e.g., an siRNA, miRNA, antisense RNA, antisense DNA, or an antibody that acts on IRX3, IRX5, or ARID5B gene or protein. Methods of measuring protein expression levels are available and well known in the art.

In an alternative aspect, the present invention provides a method of identifying an agent that modulates energy consumption in an adipocyte, said method comprising: a) measuring a first activity level of IRX3, IRX5, ARID5B, or OBE1, or a combination thereof, in an adipocyte sample; b) contacting the sample with a candidate agent; and c) measuring a second activity level of IRX3, IRX5, ARID5B, or OBE1, or a combination thereof, in the sample; wherein an increase or decrease in the second activity level as compared to the first activity level indicates that the candidate agent is an agent that modulates energy consumption in an adipocyte.

The NIH's Molecular Libraries Probe Production Centers Network (MLPCN) offers access to thousands of small molecules—chemical compounds that can be used as tools to probe basic biology and advance the understanding of the disorders described herein. Small molecules can help researchers understand the intricacies of a biological pathway or act as starting points for novel therapeutics. The Broad Institute's Probe Development Center (BIPDeC) is part of the MLPCN and offers access to a growing library of over 330,000 compounds for large scale screening and medicinal chemistry. Any of these compounds may be utilized for screening compounds involved in suppressing or inhibiting expression of somatic mutations in one or more of ARID5B, rs1421085, OBE1, IRX3 and IRX5 or a downstream target thereof.

EXAMPLES

As provided in detail herein, the present methods used epigenomics, comparative genomics, human genetics, genome editing, and directed perturbations in patient samples and in mice, to dissect the regulatory circuitry and mechanistic basis of the FTO obesity-associated locus. Epigenomic annotations across 127 human cell types and haplotype-specific enhancer assays were used to predict preadipocytes as the cell type where the genetic variant likely acts. Long-range chromatin interactions in the 2 Mb region surrounding FTO were used to define eight potential target genes. In addition, expression quantitative trait locus (eQTL) analysis in primary human adipocytes from risk and non-risk homozygous participants was used to establish IRX3 and IRX5 as genetic targets. Regulatory motif conservation and regulator expression in patients were quantified to predict disruption of ARID5B repressor binding by the T-to-C single-nucleotide variant rs1421085 as responsible for IRX3 and IRX5 dysregulation. ARID5B knockdown and overexpression in adipocytes of risk and non-risk participants, and bidirectional single-nucleotide rs1421085 alterations were performed to establish causality and epistasis. Further, functional enrichment of genes that are coordinately regulated with IRX3 and IRX5 across patients were used to hypothesize that the FTO obesity variant reduces mitochondrial activity and increases lipid storage. Knockdown and overexpression of IRX3 and IRX5 in primary human adipocytes from subcutaneous fat of risk and non-risk participants were used to examine target gene causality on mitochondrial respiration and thermogenesis. Additionally, adipose Irx3 and Irx5 perturbations in mice were performed to establish tissue-autonomous obesity roles at the cellular and organismal levels. Further, CRISPR/Cas9 editing of primary adipocytes from risk and non-risk participants was performed to establish cell-autonomous causality of the rs1421085 variant for IRX3 and IRX5 expression and for the thermogenesis and energy regulation phenotypic signatures of obesity in humans.

Primary human adipose-derived progenitor cell cultures were obtained from subcutaneous adipose tissue of 100 healthy Europeans 20 to 50 years of age who had a normal body mass index (BMI) (20 to 24 kg/m$^2$). These participants included 48 homozygous protective and 52 homozygous risk carriers for genome wide association study (GWAS) reported tag variant rs9930506 and associated variants rs1421085 and rs1558902. Primary cell cultures were used for mitochondrial and nuclear mRNA preparation, qPCR gene expression analysis, mitochondrial function/thermogenesis assays, lipolysis rate, siRNA-mediated knock-down, doxycycline-mediated overexpression, and CRISPR/Cas9 genome editing. In addition, whole adipose tissue and adipose-derived progenitor cells were obtained and RNA was isolated from a second European cohort of non-genotyped participants, including 12 severely-obese patients undergoing bariatric surgery (BMI 35 to 52 kg/m$^2$) and 22 healthy non-obese participants undergoing elective surgery (BMI 18 to 28 kg/m$^2$). The studies were approved by the local ethics committees in Germany, Norway and Sweden. All participants gave written informed consent.

Materials and Methods

A. Identifying the Cell Type of Action of Obesity-Associated Variants

1. Computational Prediction of Cell Type of Action Using Epigenomic Annotations

In protein-coding genes, gene expression levels can be used to predict where a gene is most likely to act. Since this is not possible for non-coding regions, epigenomic annotations associated with regulatory region activity were used to predict, in an unbiased way, the cell type in which the genetic variants may act.

Chromatin State Segmentations

Figure 5A:
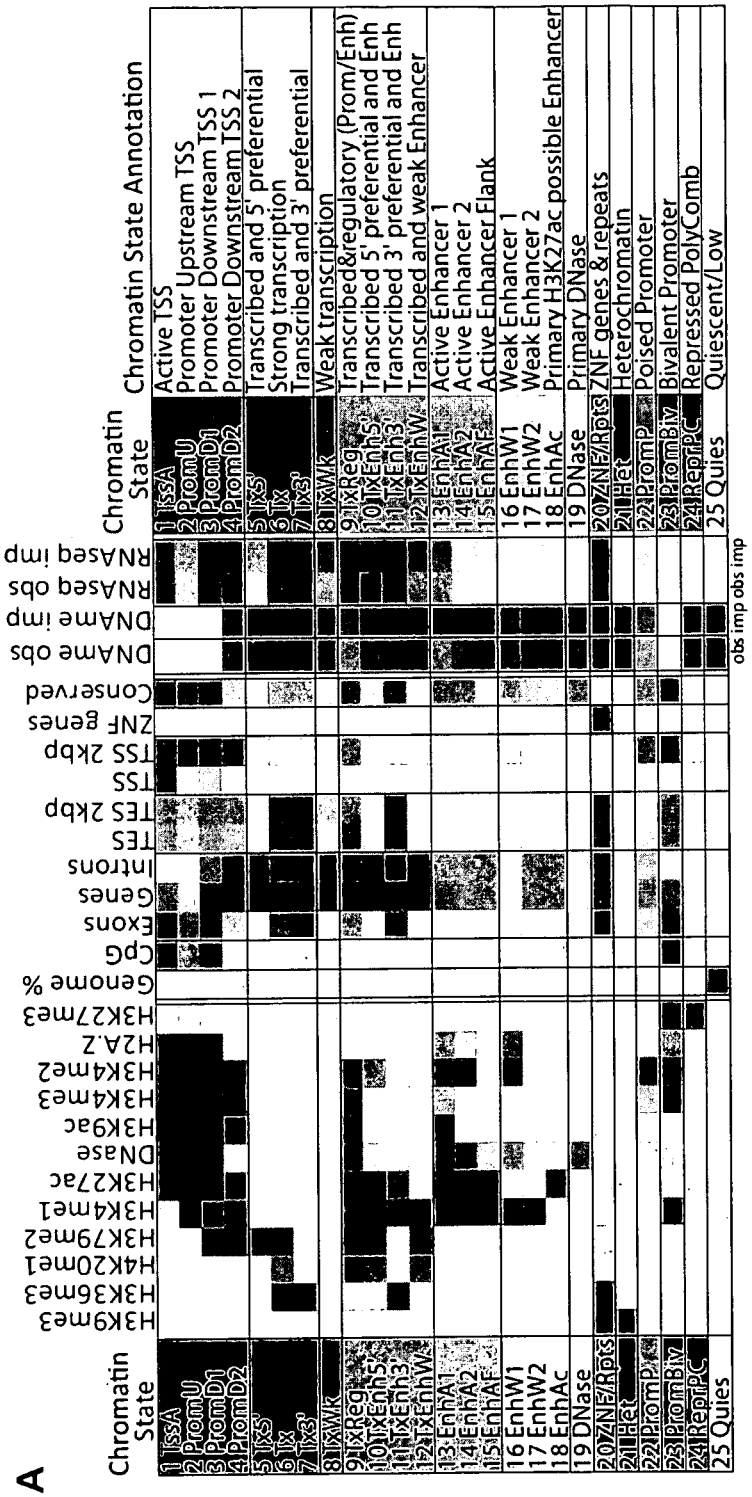
FIGS. 5A-5D. Cell type specificity and epigenomic annotations.
Figure 5B:
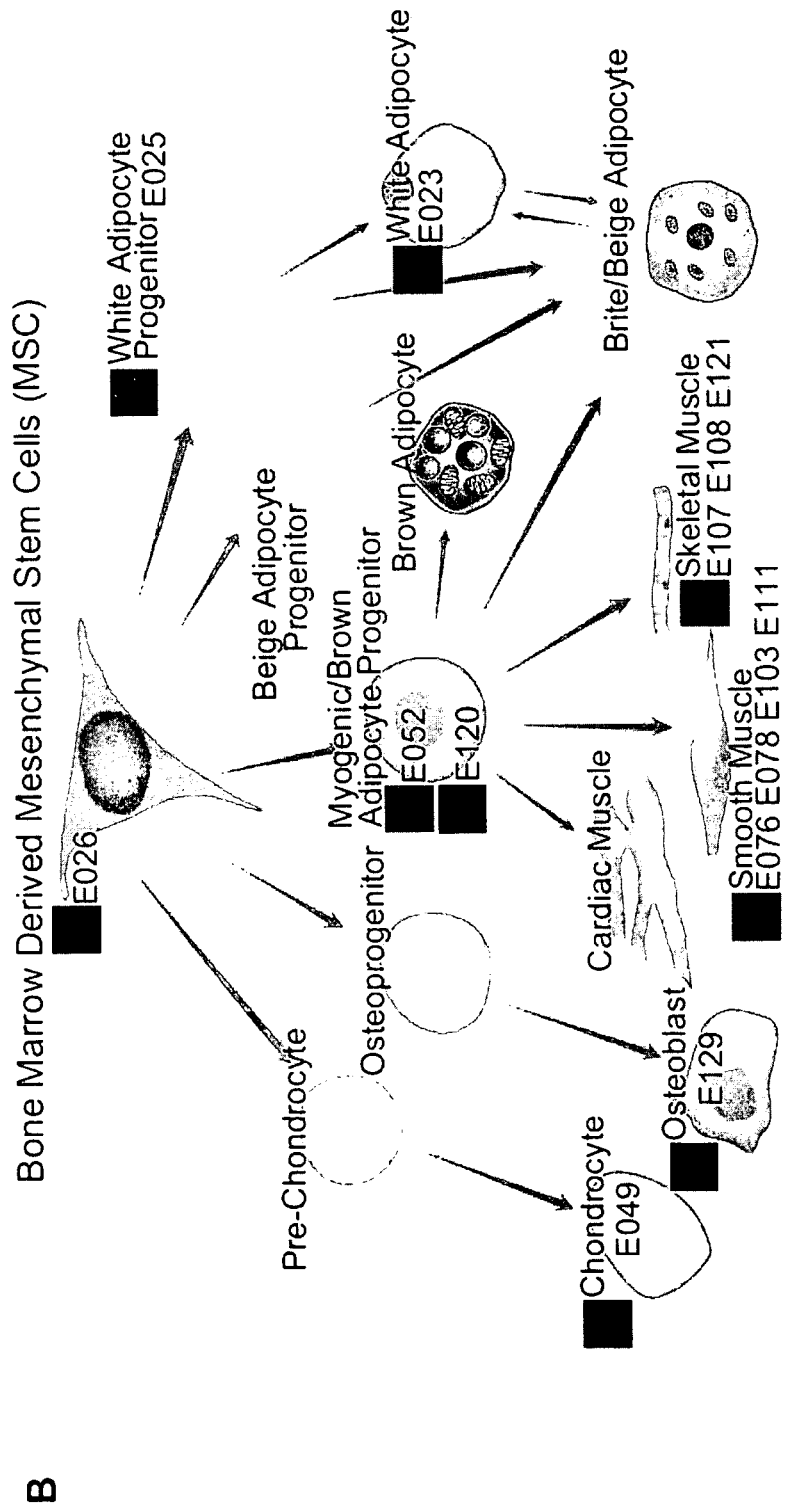

Publicly-available datasets of chromatin state annotations in 127 reference epigenomes (FIG. 1B, 5A) were used from the Roadmap Epigenomics1 and ENCODE2 projects. These include a large number of primary cells and tissue types, enabling an unbiased approach for predicting relevant cell types (FIG. 5B). These are available for download at www-.compbio.mit.edu/roadmap/ and can be visualized in the WashU Epigenome Browser (Zhou et al., Nat. Methods 8:989-90, 2011). Annotations of chromatin states were used, based on combinations of histone modification marks, using a 25-state model predicted by ChromHMM4, using 12 histone modification marks imputed by ChromImpute.

Enhancer Annotations

Figures 5C, 5D:
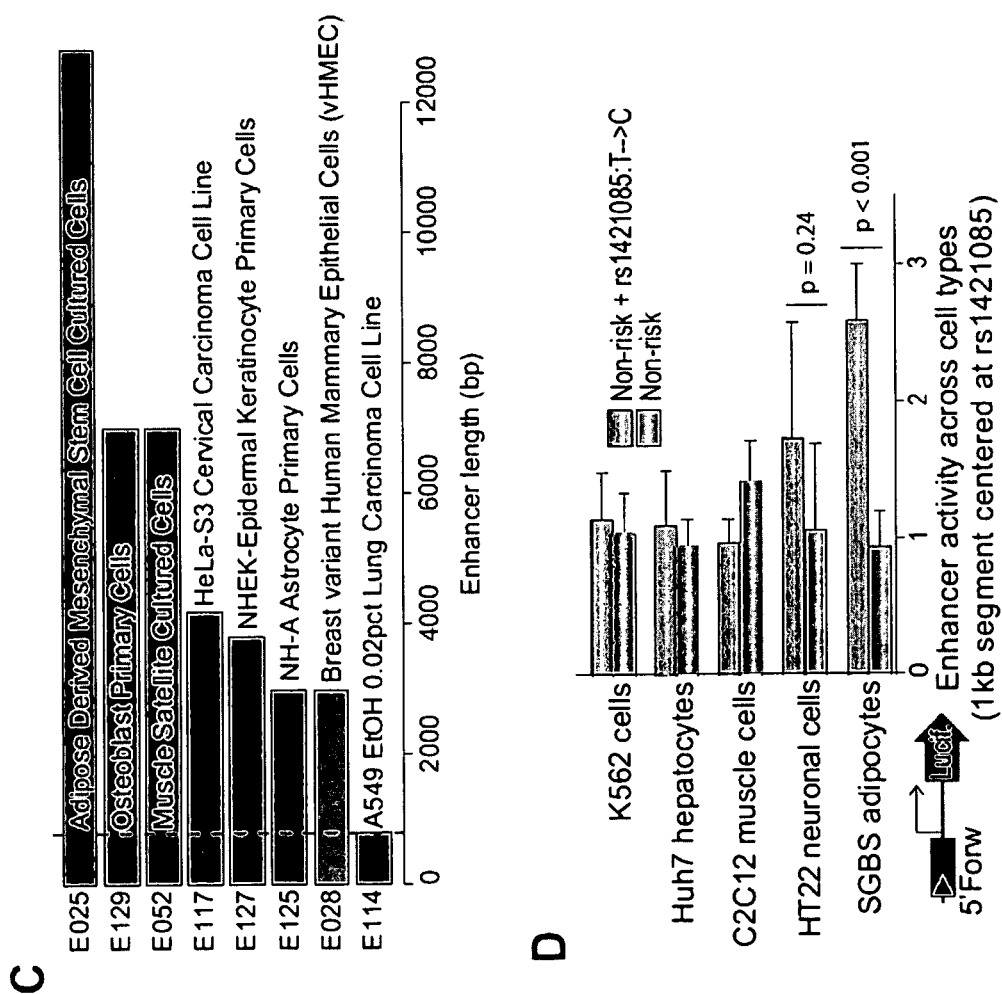

To identify putative distal regulatory elements, enhancer states (states 9-18) were examined, defined by high levels of enhancer-associated marks (H3K4me1 and H3k27ac) and lower levels of promoter-associated marks (H3K4me3, H3K4me2, H3K9ac). To recognize master regulatory loci, consecutive enhancer elements were combined into clusters, and evaluated total cluster length (FIG. 5C). Transcribed enhancers (states 9-12) that also show transcription-associated marks (H3K36me3, H4K20me1, 5 H3K79me2), active enhancers (states 13-15) that show relatively-stronger H3K27ac, and weak enhancers (states 16-18) that show relatively weaker H3K27ac were included.

2. Experimental Validation of Enhancer Activity in a Human Adipocyte Cell Line

The region showing epigenomic signatures associated with enhancer function in adipocyte cell types from the Roadmap Epigenomics project1 (Adipose-Derived Mesenchymal Stem Cells, E025) was experimentally validated as functioning as an enhancer in human adipocytes (FIG. 5D), as predicted by its epigenomic signatures.

Luciferase-Based Enhancer Reporter Assays

Luciferase reporter gene assays in human SGBS (Simpson-Golabi-Behmel Syndrome) adipocytes were performed to examine enhancer activity. Specifically, the activity of candidate regulatory elements was evaluated by cloning them upstream of a luciferase gene, transferring the resulting reporter construct into cell lines, and measuring expression of the luciferase reporter gene to quantify the activity of the enhancer.

Cloning of Reporter Constructs

For the promoter construct, a 752 bp thymidine kinase (TK) promoter was cloned upstream of the firefly luciferase gene into the EcoRV and BglII sites of the pGL4.22 firefly luciferase reporter vector (Promega). Enhancer regions were subcloned upstream of the TK promoter into the KpnI and SacI sites of the pGL4.22-TK vector in forward orientations.

SGBS Adipocyte Cell Culturing

The human preadipocyte SGBS cell line was cultured as previously described (Fischer-Posovszky et al., Obes. Facts 1:184-89, 2008) in DMEM/Ham's F12 (1:1) medium (supplemented with 10% FCS, 17 µM biotin, 33 µM pantothenic acid and 1% penicillin/streptomycin). To promote adipose differentiation of the SGBS cell line, cells were grown to confluence. For induction of adipocyte differentiation, cells were cultured in serum free MCDB-131/DMEM/Ham's F12 (1:2) medium supplemented with 11 µM biotin, 22 µM pantothenic acid, 1% penicillin/streptomycin, 10 µg/ml human transferrin, 66 nM insulin, 100 nM cortisol, 1 nM triiodothyronine, 20 nM dexamethasone, 500 µM 3-isobutyl-1-methyl-xanthine (Serva, Germany) and 2 µM rosiglitazone (Alexis, Germany). Cells were maintained at 37° C. and 5% $CO_2$.

Transfection in SGBS Adipocytes

SGBS adipocytes (12-well plate, 8×104/well) were transfected at day four after the induction of differentiation (80% confluence) with 2 µg of the respective pGL4.22-TK construct and 2 µl LIPOFECTAMINE® reagent. Firefly luciferase constructs were co-transfected with the ubiquitin promoter-driven *Renilla* luciferase reporter vector pRL-Ubi to normalize the transfection efficiency. Twenty-four hours after transfection, cells were washed with PBS and lysed in 1× passive lysis buffer (Promega, Germany) on a rocking platform for 30 min at room temperature.

Measurement of Luciferase Activity

Firefly and *Renilla* luciferase activity (substrates D-luciferin and Coelenterazine from PJK, Germany) was measured using a LUMINOSKAN ASCENT® microplate luminometer (Thermo) and a Sirius tube luminometer (Berthold). The ratios of firefly luciferase expression to *Renilla* luciferase expression were calculated and normalized to the TK promoter control vector, i.e. enhancer activity.

3. Validation of Genetic Control and Narrowing Down Candidate Region Using Enhancer Assays in Risk and Non-Risk Haplotypes Having established that the region underlying the enhancer signatures can function as an enhancer, genetic control by the FTO obesity-associated variants was examined, by separately testing the risk and the non-risk haplotypes.

Enhancer Tiling Assays

Given the large size of the obesity-associated region, tiling assays were used to narrow down the region of association. The 47 kb FTO obesity risk locus was tiled in five 10 kb segments, and synthesized each as a plasmid vector (Life Technologies). The five 10 kb tiles were: segment 1: chr16:53799507-53809507; segment 2: chr16: 53809507-53819507; segment 3: chr16:53819507-53829507; segment 4: chr16:53829507-53839507; segment 5: chr16:53839507-53849507. A 1 kb interval centered on the rs1421085 variant was also tested (chr16: 53,800,454-53,801,454).

Comparison of Risk-Allele and Protective-Allele Enhancer Constructs

For each 10 kb interval (FIG. 1C), both risk (obesity-associated) and non-risk (protective) haplotypes were synthesized using HapMap individual information (www.hapmap.ncbi.nlm.nih.gov). For the 1 kb interval centered on rs1421085 (FIG. 5D), site-directed mutagenesis (QUICK-CHANGE® II Site-Directed Mutagenesis Kit, Stratagene, Santa Clara, Calif.) was performed to introduce the C risk allele by T-to-C substitution in the non-risk T background haplotype. The identity of each construct clone by was verified by DNA sequencing. Genomic DNA segments upstream of the TK promoter were cloned into the KpnI and SacI sites of the pGL4.22-TK vector in forward orientation. Transfection in human SGBS adipocytes was performed as described above (section A2). A paired t-test was used to compute P-values comparing luciferase expression from risk and non-risk alleles. Human SGBS adipocytes were transfected as described above (section A2).

4. Validation of Adipocyte Specificity by Enhancer Assays in Diverse Cell Types

Given the cell type specific nature of epigenomic signatures of enhancer activity, it was predicted that the observed enhancer would function in a cell type specific way. In order to validate this prediction, the 1 kb enhancer reporter assay constructs (FIG. 5D) were validated in multiple cell types using both the risk and the non-risk alleles of rs1421085.

Cell Types Tested

To examine cell type specific enhancer activity for the risk and the protective allele enhancer assays were performed in multiple cell lines, including human SGBS (Simpson-Golabi-Behmel Syndrome) cells, human Huh7 hepatoma, mouse C2C12 myoblasts, HT22 neuronal cells and human embryonic kidney K562 cells.

Cell Culturing

The human Huh7 hepatoma, mouse C2C12 myoblasts, HT22 neuronal cells and human embryonic kidney K562 cells were cultured in DMEM medium (supplemented with penicillin/streptomycin and 10% FBS). The human preadipocyte SGBS (Simpson-Golabi-Behmel Syndrome) cell line was cultured as described above (section A2). All cells were maintained at 37° C. and 5% $CO_2$.

Cloning of Luciferase Reporter Gene Constructs

The promoter construct, a 752 bp thymidine kinase (TK) promoter upstream of the firefly luciferase gene, was cloned as described above (section A2). Enhancer regions were cloned upstream of the TK promoter into the KpnI and SacI sites of the pGL4.22-TK vector in forward orientations.

Transfection in Multiple Cell Types

Huh7 cells (96-well plate, $1.1 \times 10^4$/well) were transfected one day after plating with approximately 90% confluence, K562 cells (12-well plate, $8 \times 10^4$/well) three days after plating with approximately 90% confluence, SGBS adipocytes (12-well plate, $8 \times 10^4$/well) at day eight after the induction of differentiation with approximately 80% confluence and C2C12 cells (12-well plate, $2 \times 10^5$/well) at day four after induction of differentiation with approximately 90% confluence. Huh7 cells were transfected with 0.5 µg of the respective firefly luciferase reporter vector and 1 µl LIPOFECTAMINE® 2000 transfection reagent (Invitrogen, Germany), differentiated C2C12 myocytes were transfected with 1 µg of the respective pGL4.22-TK construct and 2 µl LIPOFECTAMINE® reagent, and both K562-cells and differentiated SGBS adipocytes were transfected with 2 µg of the respective pGL4.22-TK construct and 2 µl LIPOFECTAMINE® reagent. The firefly luciferase constructs with the ubiquitin promoter-driven *Renilla* luciferase reporter vector pRL-Ubi were co-transfected to normalize the transfection efficiency. Twenty-four hours after transfection, cells were washed with PBS and lysed in 1× passive lysis buffer (Promega, Germany) on a rocking platform for 30 min at room temperature.

Luciferase Measurements

Firefly and *Renilla* luciferase activity (substrates D-luciferin and Coelenterazine from PJK) was measured using a LUMINOSKAN ASCENT® microplate luminometer (Thermo Scientific™) and a Sirius tube luminometer (Berthold). The ratios of firefly luciferase expression to *Renilla* luciferase expression were measured and normalized to the TK promoter control vector, i.e. enhancer activity. Luciferase expression between risk and nonrisk alleles were compared using the P-value of a paired t-test.

B. Identifying the Target Genes of the Obesity-Associated Variants

As genetic variants can act at potentially large distances, the genes that are potentially targeted by the regulatory region harboring the FTO association with obesity were examined, as their expression may be affected by the risk haplotype.

1. Predict Putative Target Genes Using Three-Dimensional Chromatin Interactions

To predict putative target genes, topologically-associated domains surrounding the FTO locus (FIG. 1D) were first examined using chromatin conformation capture (Hi-C) (Lieberman-Aiden et al., Science 326:289-93, 2009), representing three-dimensional interactions between genomically-distal chromosomal regions that are proximal when folded in three dimensions within the nucleus (FIG. 1E), reasoning that genes within topologically-associated domains (Smemo et al., 507:371-75, 2014) may also be genetic targets.

Hi-C Data Processing and Visualization

Figure 1C:
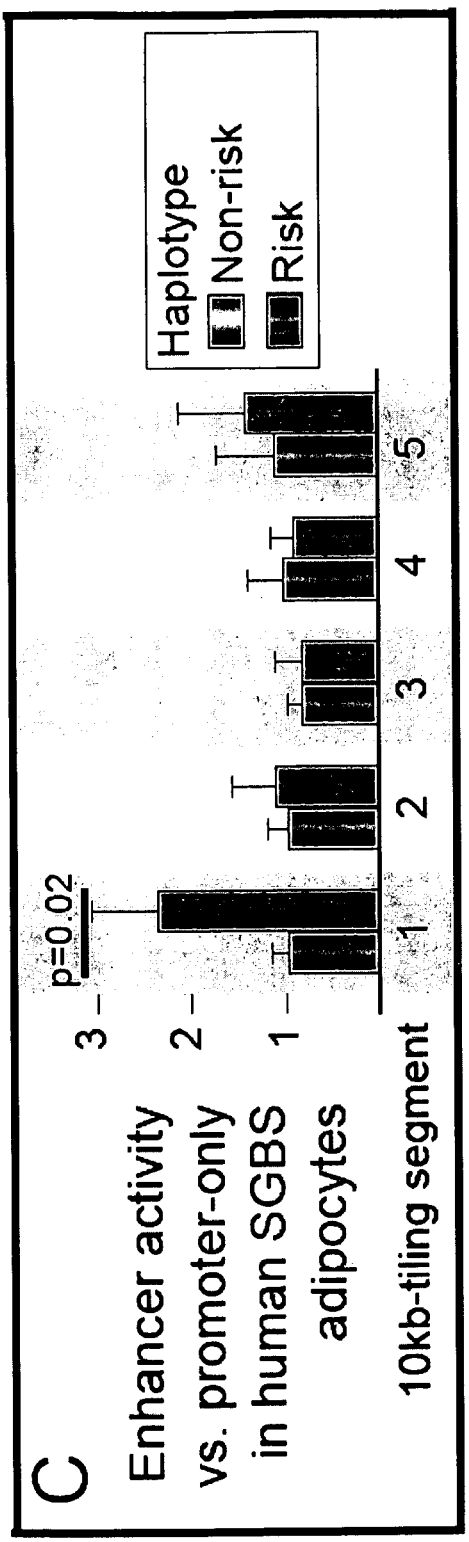

Hi-C data were obtained for a human IMR90 myofibroblastic cell study (Dixon et al., Nature 485:376-80, 2012) from GEO (accession number: GSE35156), mapped to human genome assembly hg19, and processed as described in Imakaev et al., Nature Methods 9:999-1003, 2012. Interaction heatmap patterns were visualized using the matplotlib package for Python (www.python.org). The region chr16: 52800000:56000000, binned at 40 kb resolution, was visualized (FIG. 1E, top right). Pairwise LD $r^2$ values were also visualized in Europeans, derived from 1000 Genomes Phase 1 call set and binned at 40 kb resolution. The mean $r^2$ values were plotted in each bin (FIG. 1E, bottom left).

Prediction of Candidate Target Genes

All genes in the two topologically associated domains surrounding the FTO genetic locus were considered as potential candidates. This resulted in a total of eight genes, for which eQTL analysis was undertaken, as described herein.

2. eQTL Analysis of Putative Target Genes to Identify Targets Under Genetic Control To identify the genetic target genes whose expression is altered by the obesity-associated variants, targeted expression quantitative trail locus (eQTL) analysis was performed for all potential target genes (FIG. 1F) using primary human adipocytes using patient samples from risk and protective allele carriers.

Primary Subcutaneous Adipose Tissue Isolation

Isolated cells from subcutaneous adipose tissue excisions for 38 healthy European persons 20 to 50 years of age and with a normal body-mass index (BMI) (20 to 24 kg/m$^2$) were obtained. Written informed consent was obtained from each participant. Approval by the local ethics committee of the Faculty of Medicine of the Technical University of Munich, Germany, or the Regional Committee for Medical Research Ethics (REK) of Haukeland University Hospital, Bergen, Norway was also obtained.

Selection of Homozygous Risk and Non-Risk Participants

The 38 participants were selected to consist of 18 homozygous carriers of the protective genotype, and 20 homozygous carriers of the risk genotype. No heterozygous participants were selected. Genotyping for both the GWAS reported tag SNP and the predicted causal variant rs1421085 were performed.

Cell Culturing and Differentiation

For each participant, primary mesenchymal adipocyte progenitors were isolated as previously described (Veum et al., Int. J. Obes. (London) 36:1195-202, 2012) with some modifications. Briefly, after expansion and freezing, the cells were cultured in DMEM/F12 (1:1) medium (supplemented with 10% FCS and 1% penicillin/streptomycin) for 18 h, followed by expansion in DMEM/F12 medium (supplemented with 2.5% FCS, 1% penicillin/streptomycin), 33 µM biotin, 17 µM pantothenic acid, 132 nM insulin, 10 ng/ml EGF, and lng/ml FGF until confluence. Adipogenic differentiation was induced for two days by supplementing with 66 nM insulin, 100 nM cortisol, 10 µg/ml transferrin, 1 nM triiodo-L-thyronin (T3), 2 µM rosiglitazone, 25 nM dexamethasone and 0.5 mM 3-isobutyl-1-methylxanthine (IBMX).

Sample Preparation and qPCR Gene Expression Measurements

Total RNA was extracted with TRIZOL® (Invitrogen). Copy DNA was synthesized (cDNA) with High-Capacity cDNA Reverse Transcription Kit (Applied Biosystems) or M-MLV reverse transcriptase (Invitrogen) with oligo(dT). qPCR was performed using SYBR™ Green with 60° C. annealing temperature. Relative gene expression was calculated according to the standard delta delta Ct method. Target gene expression was normalized to expression of HPRT12 or TBP.

Whole-Adipose Tissue qPCR

The analysis was repeated for IRX3 and IRX5 using whole subcutaneous adipose tissue from the same participants (FIG. 6A), in order to recognize whether the effect found in preadipocytes is also visible at the whole-tissue level for the same individuals. The presence of a strong eQTL signal at the preadipocyte level and absence of an eQTL signal at the whole-tissue level for the same set of individuals indicates that the genetic locus likely functions in a cell type specific way, and that the majority of cells represented in whole-adipose tissue (including mature adipocytes, connective tissue, blood vessels, accessory cells such as monocytes and macrophages, T cells) do not show expression differences associated with the obesity-associated variants for IRX3 and IRX5.

C. Examining Cellular Processes Affected by Obesity-Associated Variants in Humans Having identified two master regulators (IRX3 and IRX5) as genetic targets of the obesity-associated variants in preadipocytes, the correlation with their expression patterns was used to predict the cellular processes affected by the obesity-associated variants, which was validated by molecular and cellular phenotyping in risk and non-risk individuals.

1. Predict Target Cellular Processes Using Expression Correlation Across Participants To predict the cellular processes affected by obesity-associated variants, an unbiased approach was used based on genome-wide correlations in gene expression patterns. Expression in adipose tissue was measured from a separate cohort of 10 nongenotyped participants, and identified genes showing strong positive or strong negative correlation with IRX3 and IRX5 in their expression patterns.

Participants and Genome-Wide Expression Analysis

Perirenal white adipose tissue containing brown adipocytes from a separate cohort of 10 healthy kidney donors were collected; the donors were not previously genotyped and were not selected for obesity. The tissue was obtained laparoscopically under the incision plane created in the renal fascia (Greotas fascia) proximal to the renal vein. Total RNA was extracted with RNEASY® Lipid Tissue Kit (Qiagen, Hilden, Germany). Gene expression was measured using Affymetrix Gene 1.0 ST microarrays (Affymetrix, Santa Clara, Calif.), as previously described (Svensson et al., Obesity (Silver Spring) 2014).

Gene Ontology Enrichment in Positively- and Negatively-Correlated Genes

All genes were ranked by their absolute correlation with IRX3 and also with IRX5 (Pearson coefficient), and measured over-representation of gene function categories for the 500 most-correlated genes (Table 2). Table 2 shows categories with enrichment p-value<0.05. Gene expression was measured by Affymetrix microarrays in human perirenal white adipose tissue containing brown adipocytes (10 healthy persons). The two Gene Ontology terms (FIG. 2A) most enriched in the positively-correlated set with IRX5 (FXR/RXR activation) and most negatively-correlated set with both IRX3 and IRX5 (mitochondrial function) were selected, to predict roles of the obesity-associated variants in switching from energy dissipation (mitochondrial activity) to energy storage (lipid storage). Over-represented categories were determined with the PANTHER (Protein ANalysis THrough Evolutionary Relationships) Classification System (www.pantherdb.org), based on binomial statistics with Bonferroni-correction for multiple testing.

TABLE 2

Enrichment in functional categories for genes co-expressed with IRX3 and IRX5

| Gene ontology term | p-value | Correlated genes (Pearson's r > 0.5 or <−0.5) |
| --- | --- | --- |
| NEGATIVE CORRELATION WITH IRX5 | | |
| Mitochondrial Dysfunction | 0.008 | COX7B, NDUFA9, NDUFB5, ATP5S, MT-CO2, ATP5E, NDUFA2, VDAC2, CASP9, GPD2, MT-CYB, NDUFAB1, ATP5J2, NDUFB6, ATPAF1, MT-CO3, PARK2, COX4I1, AIFM1, MT-CO1, SDHA, MAPK8, MAPK9, SDHC, VDAC3, GPX7, UQCRB, MT-ND1, MT-ND5, COX11, ATP5L2, NDUFV2, CAT, MAPK10, NDUFA12, SDHD, MT-ND3, UQCRQ |
| Aryl Hydrocarbon Receptor Signaling | 0.014 | TRIP11, POLA1, NQO2, RBL1, RARG, PTGES3, ARNT, SP1, ALDH3A2, GSTM4, ALDH6A1, ALDH5A1, GSTK1, ATM, MGST1, RBL2, MED1, GSTA4, GSTM3, CYP2C18, CDK6, MAPK8, ALDH9A1, RXRG, ALDH1L2, CYP3A4, NFIA, CYP3A43, NFIB, DHFR, DCT, CDKN1B, ESR1, MGST3, MCM7 |
| TR/RXR Activation | 0.022 | PIK3C2B, AKT2, AKR1C1/AKR1C2, MED1, UCP1, ME1, THRSP, RXRG, PDE3B, SREBF1, PIK3C3, NCOA1, NCOA4, ACACA, STRBP, PIK3CB, TBL1XR1, THRB, PPARGC1A, ATM |
| POSITIVE CORRELATION WITH IRX5 | | |
| FXR/RXR Activation | 0.002 | G6PC2, IL1A, APOA4, SLC10A1, PKLR, APOH, FOXA1, APOA2, APOC4, VTN, C9, APOC2, IL1F10, HNF1A, SLC27A5, NR0B2, SLC51A, CYP19A1, RARA, SLC10A2, CYP7A1, GC, HNF4A, FGF19, TTR, SDC1, FETUB, IL36A, MAPK12, SULT2A1, A1BG, SERPINF2, APOA1, FABP6, FOXO1, ORM1, FOXA2, IL36RN, G6PC, SLC51B, FGA, FOXA3, APOC3 |
| Hepatic Cholestasis | 0.004 | SLC22A6, IL1R2, IL1RL2, NR0B2, ADCY5, PPRC1, RARA, OSM, HNF4A, NFKBIB, IL1RAP, FGF19, CXCL8, IL36A, MAPK12, IL36RN, PRKACG, ESR1, RELA, IL1A, IL12A, SLC10A1, IL17C, IL1RL1, IL1F10, HNF1A, IL25, IL17B, IRAK1, NFKBIA, NGFR, SLC10A2, IL17D, CYP7A1, PRKAR1B, PRKCE, CHUK, ADCY8, TNFRSF1B, ADCY2, IL3, RELB, IL1R1, IRAK3, PRKCG, GCG, TRAF2, FABP6, IL12B, LTA, ADCY1, IL11 |
| Vasopressin-induced Genes in Inner Medullary Renal Collecting Duct Cells (Rat) | 0.017 | AQP3, WNK4, WNK1, AQP4, AQP2 |
| Increases Liver Hepatitis | 0.023 | TNFRSF18, LEP, LTB, STAT3, IL1R1, IL17RA, TBX21, IL25, NR0B2, IL12B, CNR2, LTA, BID, SERPINE1, TNFRSF1B, CYR61, ESR1, PDX1 |
| Cytochrome P450 Panel-Substrate is a Vitamin (Human) | 0.025 | CYP24A1, CYP26C1, CYP26A1, CYP27B1 |
| LXR/RXR Activation | 0.027 | RELA, IL1A, LPA, APOA4, APOH, ABCG4, IL1RL1, APOA2, APOC4, VTN, C9, APOC2, IRF3, IL1F10, IL1R2, IL1RL2, NGFR, CYP7A1, NOS2, TNFRSF1B, GC, IL1RAP, TTR, RELB, IL36A, APOA5, IL1R1, A1BG, SERPINF2, APOA1, ORM1, IL36RN, NCOR2, FGA, MMP9, APOC3, CCL7 |
| Cardiac Hypertrophy | 0.036 | CHGA, TCF15, TNNC1, TNNT2, CACNA1H, CORIN, ATP2A2, SOD2, GAL, mir-15, TXN, SERPINE1, MYH7, STAT3, HMGA1, CSF3, DES, MYL9, AKAP13, IRX4, HPRT1, AGTR2, EPO, CA2, MB, GUCY2C, IL1RL1, HSPB8, MYLK3, SIRT7, mir-1, F2RL1, UCN, FGF23, PRKCE, VDR, LTK, SCNN1B, MMP1, HTR2A, ENDOG, ALOX15, SLC4A1, FLT1, MYOD1, XIRP1, mir-30, SLC6A4, ADORA2A, CSRP3, INHA, HAND1, FKBP1B, OSM, CAV3, ELN, MIF, HDAC4, RRAD, IL6R, RAPGEF3, INHBA, BMP10, LMCD1, ANKRD1, APLN, mir-210, SMTN, MMP7, LEP, TERT, MKL1, NFATC1, PGF, KCNJ11, SHC1, NFKBIA, CYP19A1, FOXO3, NOS2, ACTC1, RASSF1, TIMP3, EPAS1, TRIM55, CKM, PPARD, NFATC4, BIRC5, HOPX, NKX2-5, mir-208, ADRA2C, CYP2J2, RCAN2, COL9A2, MMP9, GATA4, MYBPC3, IL11 |

TABLE 2-continued

Enrichment in functional categories for genes co-expressed with IRX3 and IRX5

| Gene ontology term | p-value | Correlated genes (Pearson's r > 0.5 or <−0.5) |
| --- | --- | --- |
| Protection from Hypoxia-induced Renal Ischemic Injury (Rat) | 0.037 | VEGFA, EPO, SLC2A1 |
| Cardiac Fibrosis | 0.04 | TNNT2, CACNA1H, ATP2A2, HTR1B, SOD2, PDCD1, CNR2, SERPINE1, CAV3, PTX3, SNAI1, TNNI3, STAT3, CSF3, DES, TLR2, AGTR2, PVRL2, EPO, GPX1, TBXA2R, HSPB8, MYLK3, PPP1CB, SIRT7, MAPK11, mir-34, DTNA, mir-1, CYP11B2, VDR, NOS2, ACTC1, RASSF1, TIMP3, SLC4A1, LIMS2, XIRP1, let-7, F3, PLG, HOPX, mir-30, APOA1, CAPNS1, mir-208, SLC6A4, ADRA2C, CSRP3, MMP9, MYBPC3 |
| Cardiac Necrosis/Cell Death | 0.043 | XDH, CTSG, GHRH, VEGFA, mir-154, CASR, SOD2, BAG1, ADCY5, CNR2, FOSL1, JUND, mir-320, CAV3, ABCB8, RRAD, LCN2, STAT3, CSF3, THBD, mir-144, BMP10, INHBA, BACH1, TLR2, BCL2L1, MPO, APLN, PPP1R15A, E2F1, ZYX, CYR61, WNT1, PVRL2, EPO, LEP, TERT, MYLK3, HSPB8, SIRT7, CAMK2N2, E2F3, MAPK11, RNASE3, mir-34, IRAK1, NRG1, FSTL1, mir-1, UCN, MANF, FOXO3, SST, CACNB2, MAPKAPK2, NOS2, ACTC1, GHRL, ADAMTS13, MT1A, BIRC5, STAR, GCG, NKX2-5, APOA1, WISP1, CYP2J2, CXADR, GATA4, MYBPC3, CALCA |
| NEGATIVE CORRELATION WITH IRX3 | | |
| Mitochondrial Dysfunction | 1.47E−12 | MAP2K4, NDUFA9, UQCR11, NDUFB5, ACO2, NDUFB8, MT-CO2, VDAC2, NDUFB10, PDHA1, NDUFS1, NDUFA5, MAOB, NDUFA10, UQCRFS1, GPX4, ATP5F1, NDUFA8, ATP5J, COX7C, SDHC, COX7A1, PRDX3, ATP5B, TXN2, NDUFA6, UQCRC2, MAPK10, NDUFA12, MT-ND3, COX7B, ATP5H, COX7A2L, ATP5S, NDUFA2, MT-CYB, NDUFAB1, ATP5J2, ATPAF1, MT-CO3, NDUFB6, PARK2, OGDH, COX4I1, NDUFS4, AIFM1, MT-CO1, NDUFAF1, UCP2, ATP5O, MAPK8, MAPK9, LRRK2, VDAC3, NDUFS3, UQCRB, MT-ND5, MT-ND1, COX11, ATP5L2, NDUFV2, UQCR10, CYC1, CAT, SDHD, COX15 |
| TR/RXR Activation | 0.003 | AKT2, PIK3CA, AKR1C1/AKR1C2, UCP2, MED1, NCOA6, THRA, ME1, PIK3R4, THRSP, F10, NCOA2, PDE3B, PIK3C3, NCOA1, NCOA4, ACACA, STREP, PIK3CB, TBL1XR1, THRB, RXRB, ATM, PPARGC1A |
| RAR Activation | 0.004 | MAP2K4, PRKACB, NSD1, PIK3CA, ADH1C, PDPK1, SMAD5, MNAT1, PRKAG1, TRIM24, ALDH1A1, KAT2B, CSNK2A1, GTF2H5, SMAD4, RXRB, PRKD3, CITED2, PNPLA4, GTF2H3, SMAD2, AKT2, GNAS, MED1, NRIP2, MAPK8, MAPK9, SNW1, PARP1, CSNK2A2, MAPK14, PRKAR2B, SMARCA2, PRKCD, ERCC3, MAPK10, NCOA1, PRKACA, PIK3CB, HLTF, PPARGC1A, RBP4 |
| Biogenesis of Mitochondria | 0.008 | PTCD2, PRDX3, GNAS, TFAM, CAV2, CEBPA, ADRB3, PPARGC1A |
| Fatty Acid Metabolism | 0.009 | ADH1C, ACAA2, HADHB, ALDH2, ADH1A, ALDH1A1, ECI2, ALDH3A2, ACAD8, ACADM, HSD17B4, HADHA, ALDH5A1, ALDH7A1, ECHS1, ACAA1, ACOX1, ECH1, ALDH9A1, ACADS, ACADL, AUH, ACAT1, CPT2, ADH1B, IVD, ADHFE1, HADH, ACSL1 |
| POSITIVE CORRELATION WITH IRX3 | | |
| Primary Glomerulonephritis Biomarker Panel (Human) | 3.70E−05 | TYMS, ELF3, EGR1, HBEGF, IER3, SERPINE1, SAMD4A, MAFF, MCL1 |
| Cardiac Necrosis/Cell Death | 4.10E−05 | SOCS3, LIF, SPRR1A, XDH, IL6, NOS3, GHRH, NTN1, mir-154, BBC3, SOD2, PIM1, JUND, FOSL1, CAV3, ABCB8, MCL1, RRAD, LCN2, TRIM54, STAT3, CSF3, THBD, INHBA, BACH1, DAXX, MPO, APLN, PPP1R15A, E2F1, THBS2, ZYX, MAP2K3, MDK, CYR61, CDK2, WNT1, mir-21, PVRL2, EPO, MYH6, LEP, PTK2B, HSPB8, MYLK3, TNFAIP3, SIRT7, HIF1A, CAMK2N2, E2F3, MAPK11, mir-34, FAS, RNASE3, IRAK1, NRG1, FSTL1, TIMP1, UCN, MANF, SST, NAMPT, MAPKAPK2, MAP2K1, GHRL, PLAT, IFNG, ADAMTS13, PPIF, CXCR4, MT1A, BIRC5, |

TABLE 2-continued

Enrichment in functional categories for genes co-expressed with IRX3 and IRX5

| Gene ontology term | p-value | Correlated genes (Pearson's r > 0.5 or <−0.5) |
|---|---|---|
| | | IL17A, STAR, GCG, IVNS1ABP, GNAI2, APOA1, CDKN1A, BRCA2, CYP2J2, NPPA, CXADR, MYBPC3, CALCA |
| Hepatic Cholestasis | 4.46E−05 | GCGR, LIF, IL6, SLC22A6, CYP8B1, ATP8B1, IL1RL2, NR0B2, RARA, PPRC1, ABCC1, OSM, NFKBIB, HNF4A, IL17F, IL1RAP, FGF19, TNFRSF11B, MAP3K14, CXCL8, PRKCQ, SLCO1A2, NFKB2, MAPK12, PRKACG, IL36RN, TGFB3, ESR1, RELA, IL1A, IL12A, IL17C, NFKBIE, IL1F10, SLC22A7, HNF1A, PRKCZ, IRAK1, IL17D, NGFR, SLC10A2, CYP7A1, PRKCE, LBP, TNFRSF1B, ABCB1, IFNG, TNFRSF1A, RELB, IL1R1, FL17A, GCG, TRAF2, SLCO3A1, LTA, ADCY1, ABCC3, IL11 |
| Cardiac Hypertrophy | 1.33E−04 | CHGA, CTGF, TNNT2, CACNA1H, HRAS, IL6, NOS3, ATP2A2, EEF1D, CABIN1, FHL2, SOD2, GAL, TCAP, GAA, PNKD, TXN, SERPINE1, AHR, CACNA1C, HBEGF, MYH7, HMGA1, STAT3, IER3, CSF3, DES, MNT, AKAP13, TRIM63, IRX4, MAP2K3, MAPK7, AGTR2, mir-21, EPO, MB, GUCY2C, HSPB8, MYLK3, SIRT7, DUSP5, UCN, FGF23, PRKCE, VDR, LTK, SCNN1B, MMP1, HTR2A, PLAT, RGS2, PTGIR, GRB2, XIRP1, mir-30, MYOCD, CDKN1A, ADORA2A, INHA, LIF, SMAD3, FKBP1B, PIM1, OSM, CAV3, MIF, ATF3, RRAD, IL6R, TRIM54, INHBA, LMCD1, ANKRD1, ADRA2A, DUSP1, APLN, mir-210, SMTN, ABCC4, S100A6, ANGPT2, MYH6, LEP, PDGFA, DACT1, TNFAIP3, MKL1, HIF1A, NFATC1, KCNJ11, HTR2C, SHC1, TIMP1, GATA6, MAP2K1, RASSF1, VAV2, EPAS1, UCN2, TRIM55, PPARD, NFATC4, BIRC5, GNAI2, RCAN1, NFATC2, ADRA2C, CYP2J2, NPPA, RCAN2, MYBPC3, IL11 |
| Liver Necrosis/Cell Death | 6.81E−04 | mir-146, SOCS1, SOCS3, INHA, CD40LG, LIF, SMAD3, HRAS, IL6, CCND1, PTGER1, MYC, F11, CXCL3, SOD2, BBC3, NR0B2, CPB2, OSM, JUND, IGFBP1, HNF4A, SERPINE1, NFKBIB, AHR, MCL1, HRH2, SELE, IL6R, HBEGF, STAT3, IER3, INHBA, MNT, DAXX, SELP, E2F1, FGA, ESR1, EPO, SIGIRR, RELA, GADD45B, SLC26A1, UGCG, FKBP1A, SMPD1, IRF3, USP2, FAS, TACR1, SHC1, FGF4, FLNA, TIMP1, PROS1, NGFR, CIT, NR1I3, PTPN1, CYP7A1, SST, TNFRSF1B, MAP2K1, RRBDD3, SLC20A1, MYCN, IFNG, IL10, TNFRSF1A, IL15, XBP1, PLK1, BAX, IL17A, BUB1, PLG, LDLR, ABL2, CDKN1A, MAP3K8, TNFSF14 |
| Cardiac Fibrosis | 8.39E−04 | SMAD3, TNNT2, CACNA1H, HRAS, NOS3, ATP2A2, F11, HTR1B, SOD2, PDCD1, NDUFS6, PNKD, SERPINE1, CAV3, AHR, PTX3, ATF3, SNAI1, HBEGF, TNNI3, LMNA, CACNA1C, STAT3, CSF3, BUB1B, DES, DIO3, ADRA2A, THBS2, mir-21, AGTR2, PVRL2, EPO, MYH6, ANGPT2, TBXA2R, MYLK3, HSPB8, TNFAIP3, SIRT7, MAPK11, mir-34, TIMP1, VDR, RASSF1, PLAT, VAV2, IFNG, PTGIR, GRB2, EGR1, XIRP1, let-7, PLG, APOA1, mir-30, ADRA2C, MYBPC3 |
| Increases Liver Damage | 9.43E−04 | LTB, SMPD1, IL6, F2, FAS, PRKCZ, PTGER1, NR0B2, TICAM1, PDCD1, PTPN1, CYP7A1, OSM, LBP, SERPINE1, TNFRSF1B, ALDH3A1, FGR, PLAT, IFNG, MIF, TNFRSF1A, EGR1, IL6R, XBP1, STAT3, IL1R1, GH1, CSF3, IL17A, PLG, FOXA2, LTA, CDKN1A, CD44, MAP3K3, GSTP1 |
| Increases Liver Hyperplasia/Hyperproliferation | 0.002 | S100A6, LEP, LIF, HMMR, NCAPG, LTB, HRAS, TLX1, CXCL5, IL6, CCND1, TGFBR2, MYC, mir-26, NR1I3, OSM, GHRL, AHR, FGF19, CXCR4, PCSK9, RRM2, AGO2, STAT3, FOXM1, BIRC5, IGFBP2, HPN, BUB1, LTA, E2F1, CENPA, mir-I92, TGFA, mir-17, IL11 |
| Increases Renal Nephritis | 0.003 | IFNG, CD19, CD40LG, LIF, LEP, TNFRSF1A, IL10, IL21R, COL4A3, IL17A, MPO, CSF1, PIM1, LTA, GP1BA, ICOS, TNFSF14 |
| Liver Proliferation | 0.005 | mir-146, SOCS3, CTGF, XDH, SMAD3, HRAS, LTB, IL6, CCND1, F2, MYC, TGFBR2, CXCL3, RARA, CPB2, SLC7A5, OSM, OSMR, JUND, IGFBP1, HNF4A, AHR, FGF19, IL4R, IL6R, HBEGF, INHBA, E2F1, MDK, CDK2, mir-21, WNT1, EPO, LEP, SMPD1, HNF1A, FAS, TNFRSF12A, TIMP1, THBS1, PROS1, NGFR, NR1I3, CIT, GDF2, SULF2, TNFRSF1B, |

TABLE 2-continued

Enrichment in functional categories for genes co-expressed with IRX3 and IRX5

| Gene ontology term | p-value | Correlated genes (Pearson's r > 0.5 or <−0.5) |
|---|---|---|
|  |  | SLC20A1, IFNG, S1PR2, EDNRB, PPARD, CXCR4, TNFRSF1A, NPPC, XBP1, FOXM1, PLG, WNT3A, LY9, RETN, LTA, CDKN1A, CSHL1, TGFA |
| Increases Liver Hepatitis | 0.008 | IFNG, TNFRSF18, LEP, TNFRSF1A, IL10, LTB, IL6, STAT3, IL1R1, FAS, IL17A, CCL2, NR0B2, LTA, SERPINE1, TNFRSF1B, CYR61, ESR1, PDX1 |
| Hepatic Fibrosis | 0.01 | IGFBP4, IL1A, CD40LG, ICAM1, LEP, PDGFA, SMAD3, COL4A3, VTN, IL6, TGFBR2, TNC, CCL2, ECE2, THBS1, TIMP1, IGFBP1, MMP1, AHR, CXCL8, IFNG, SDC1, IL10, BGN, IGFBP2, ACTA2, CSF1, THBS2, TGFA, TGFB3, mir-21 |
| Hepatic Stellate Cell Activation | 0.011 | CXCL8, RELA, IFNG, IL10, PDGFA, TGFBR3, NFKB2, IL6, TGFBR2, CCL2, TIMP1, TGFA, TGFB3, KLF2 |
| Genes associated with Chronic Allograft Nephropathy (Human) | 0.024 | TNC, VCAM1, ICAM1, CCL2, PDGFA, THBS1, TIMP1, MATN1, CCL19 |
| Acute Renal Failure Panel (Rat) | 0.034 | GAS2, VCAM1, ATF3, RRAD, SLC9A3, EGR1, LCN2, FKBP1A, IL6, PRODH2, TNFRSF12A, MYC, ACTA2, CDKN1A, SPHK1, CD44, TAGLN, FOSL1, IGFBP1, COL18A1 |
| Positive Acute Phase Response Proteins | 0.044 | C4A/C4B, SOD2, APCS, C9, CRP, LBP, SERPINE1, FGA, HMOX2, SERPINF2, FGG |
| FXR/RXR Activation | 0.045 | IL1A, APOA4, PKLR, APOF, FOXA1, APOA2, VTN, C9, AMBP, APOC2, IL1F10, SLC22A7, HNF1A, CYP8B1, C4A/C4B, SLC27A5, NR0B2, SLC51A, RARA, SLC10A2, CYP7A1, HNF4A, FGF19, SDC1, FETUB, AHSG, MAPK12, SULT2A1, SERPINF2, APOA1, ORM1, FOXA2, IL36RN, FGA, FOXA3, APOC3 |
| Genes Downregulated in Response to Chronic Renal Failure (Rat) | 0.045 | CYP1A1, SLC22A12, SLC17A1, SLC22A7, SLC22A6 |
| LXR/RXR Activation | 0.045 | RELA, IL1A, LPA, APOA4, APOF, APOA2, VTN, C9, AMBP, ABCG1, APOC2, IRF3, IL6, IL1F10, C4A/C4B, CCL2, IL1RL2, NGFR, CYP7A1, LBP, TNFRSF1B, IL1RAP, TNFRSF11B, TNFRSF1A, RELB, AHSG, NFKB2, IL1R1, SERPINF2, LDLR, APOA1, ORM1, IL36RN, FGA, APOC3 |
| Decreases Depolarization of Mitochondria and Mitochondrial Membrane | 0.049 | ABCC1, CDKN1A, PLIN3, MAP2K1, ATP2A2, BIRC5, FAS, MCL1 |

2. Provide Expression Support for Roles in Adipocyte Browning and Thermogenesis

Given the correlation of IRX3 and IRX5 gene expression with energy balance genes, their potential differential expression between white and brown fat in human were examined; their potential correlation with thermogenesis regulator UPC1 was also examined. Specifically, given their positive correlation with lipid storage and negative correlation with mitochondrial activity, their higher expression in white fat tissue, lower expression in brown fat tissue, and negative correlation with thermogenesis regulator UCP1 was predicted.

Figures 6A, 6B, 6C, 6D:
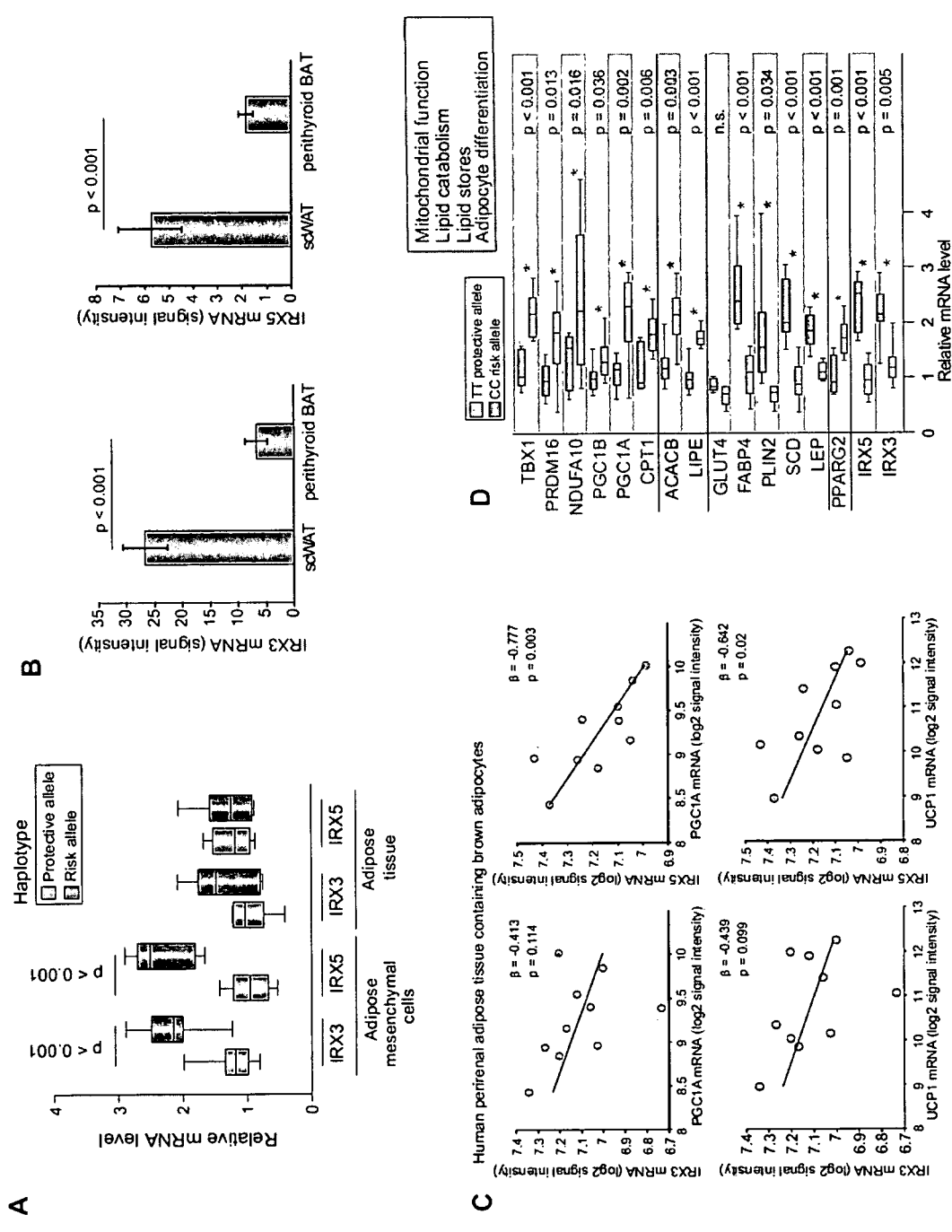

Evaluate Differential IRX3 and IRX5 Expression Between Brown and White Fat Tissue To evaluate differential IRX3 and IRX5 expression levels in brown and white fat, 9 brown (perithyroid) and 9 paired subcutaneous white adipose tissue biopsies from healthy participants using Affymetrix microarrays (IRX3 probe set 229638_at, IRX5 probe set 210239_at) were analyzed (FIG. 6B).

Evaluate Expression Correlation of IRX3 and IRX5 with Thermogenesis Regulators UCP1 and PGC1A Using Affymetrix microarray data, UCP1 and PGC1a, genes coexpressed with IRX3 and IRX5, were analyzed in perirenal white adipose tissue containing brown adipocytes obtained from healthy kidney donors (n=10) (FIG. 6C).

3. Validate Genetic Control of Expression for Energy Balance Genes in Adipocytes To establish that the pathways positively- and negatively-correlated with IRX3 and IRX5 across participants are indeed under the genetic control of the obesity-associated variants at the FTO locus, qPCR was used to evaluate the expression of key marker genes of mitochondrial function and lipid storage in risk and non-risk homozygous participants.

Targeted qPCR of Energy Balance Regulators in Risk and Non-Risk Participants

Isolation, culturing, and differentiation of primary human adipose progenitor cells were performed as described above (section B2). RNA was extracted using TRIZOL® (Invitrogen) from primary human adipose progenitors at day 2 of differentiation from 18 homozygous non-risk and 20 homozygous risk allele carriers. cDNA was synthesized with High-Capacity cDNA Reverse Transcription Kit (Applied Biosystems, Waltham, Mass.). qPCR was performed using SYBR™ Green with 60° C. annealing temperature and calculated relative gene expression by the delta delta Ct method. Target gene expression was normalized to expression of HPRT12 or TBP (human).

Trans-eQTL Analysis of Targeted Genes

Figure 6F:
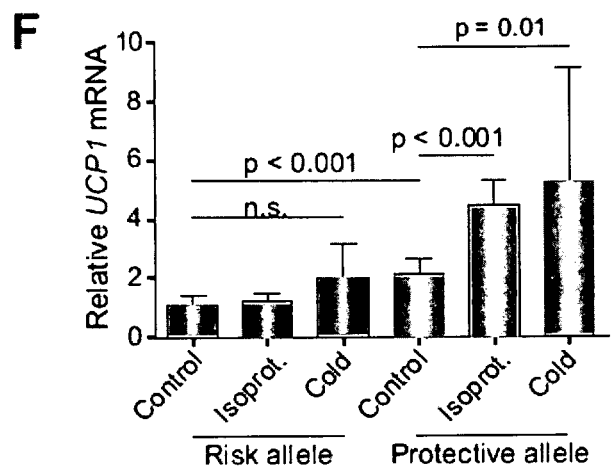

For each targeted gene, a UMann-Whitney test P-value was calculated to detect statistically-significant differences in the expression of risk and non-risk participants. Significant differences (P<0.05) for all targeted genes were found (FIGS. 6D and 6E), with risk participants showing significantly increased expression of lipid storage genes, and significantly increased expression of mitochondrial function and lipid catabolism genes. This indicates that these distally-located genes are trans-acting expression quantitative locus (trans-eQTL) targets of the obesity-associated genetic variants, indicating genetic control of energy balance genes by the FTO locus in human adipocytes. To verify whether genes in the predicted energy balance pathways are under genetic control by the obesity-associated variants, regulation of UCP1 gene expression under thermogenic stimulatory conditions was evaluated (FIG. 6F). For stimulation experiments, cells were stimulated with isoproterenol (1 µmol/l) for 12 hours or exposed to 30° C. for 6 hours before mRNA was harvested.

4. Validate Genetic Control of Browning-Associated Cellular Phenotypes in Humans The participants at risk showed reduced expression in mitochondrial, browning and respiration genes, and higher expression for lipid storage markers, indicating a shift from energy dissipation to storage. Whether those expression differences are also reflected in cellular signatures of obesity was tested.

Triglyceride Accumulation in Primary Human Adipocytes

Figure 2A:
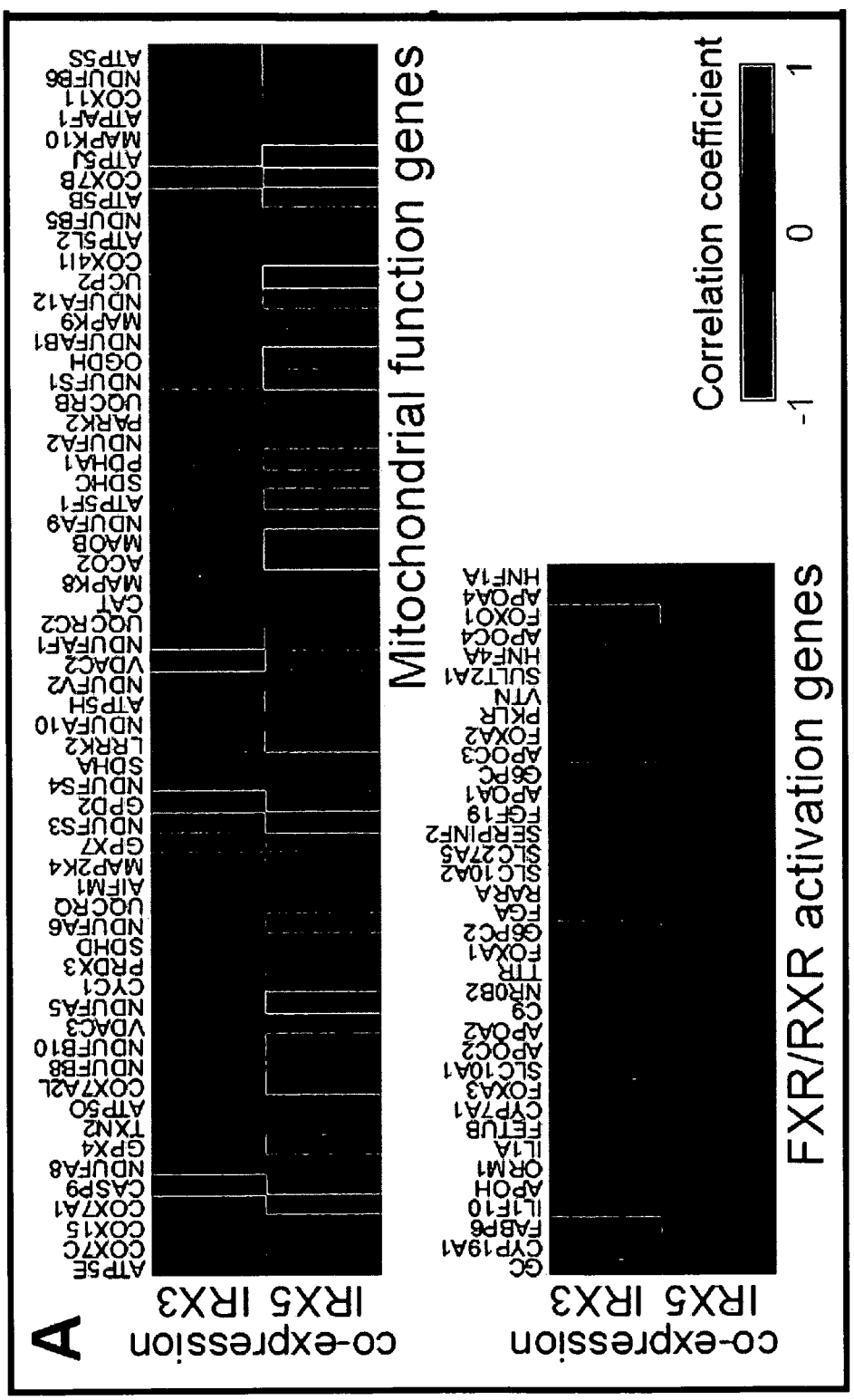
FIGS. 2A-2D. IRX3 and IRX5 regulate obesity-associated cellular phenotypes in human adipocytes.
Figures 2B, 2C, 2D:
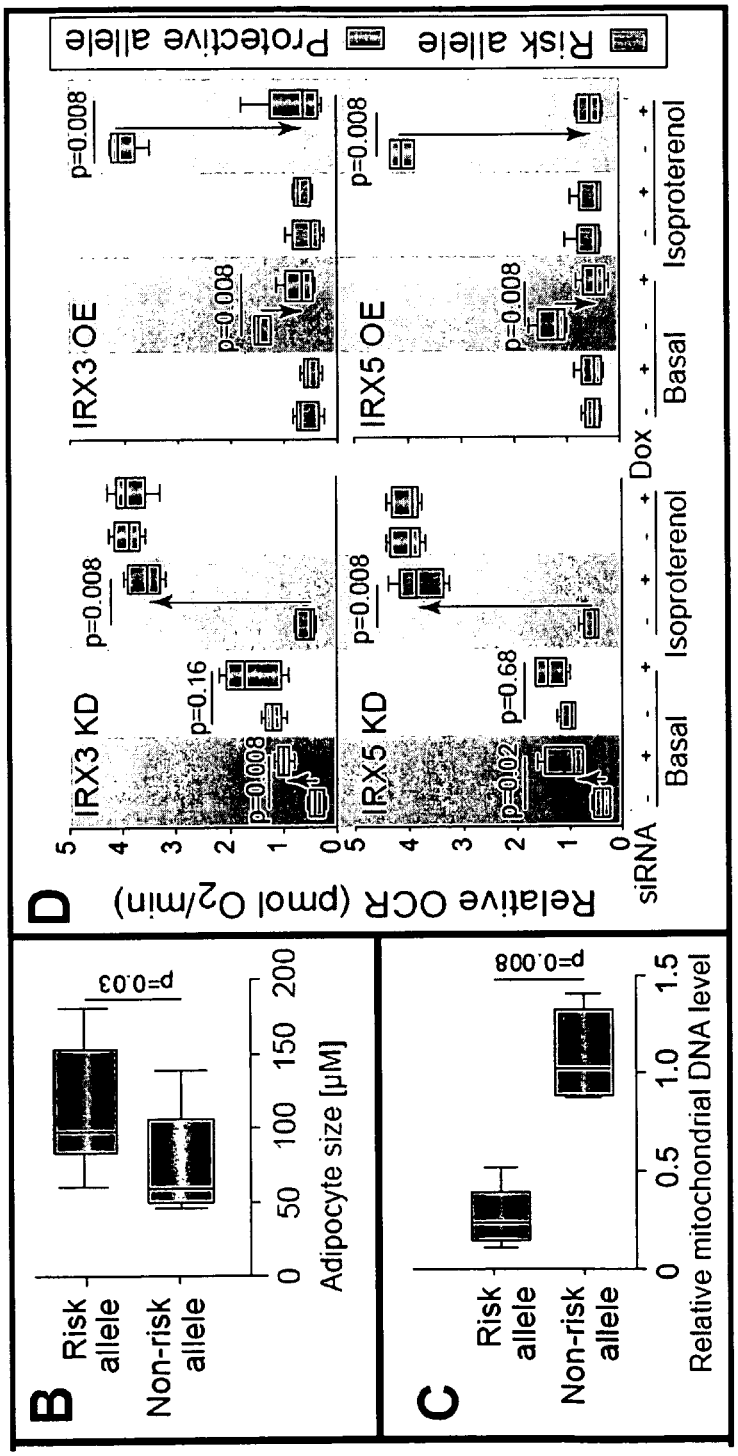

To assess the extent of triglyceride accumulation in adipocytes from risk compared to protective allele participants, cell size in isolated differentiated adipocytes was measured (FIG. 2B). For preparation of mature adipocytes and cell size determination, subcutaneous adipose tissue from rs1421085 CC risk (n=16) and TT non-risk (n=26) allele carriers were minced and digested in Krebs-Ringer-Phosphate buffer (KRP; 154 mm NaCl, 100 mm NaH2PO4, 154 mm KCl, 154 mm MgSO4, 110 mm $CaCl_2$), pH 7.4) containing 100 U/ml collagenase and 4% BSA for 60 min at 37° C. in a shaking water bath. After this step, the undigested tissue was removed by filtration through a nylon mesh with a pore size of 250 µm (VWR, Darmstadt, Germany). The floating adipocytes were washed three times with KRP containing 0.1% BSA and used to assess the mean cell diameter based on the measurement of 100 cells from each fraction under the microscope. Genotyping was performed by MassARRAY (Sequenom, San Diego, Calif.), Omni express (Illumina, San Diego, Calif.) or Sanger Sequencing.

Mitochondrial Biosynthesis in Primary Human Adipocytes

To examine an association of the rs1421085 variant with mitochondrial mass, as a surrogate measure of cellular respiratory capacity, mitochondrial DNA (mtDNA) content in primary human adipose cell cultures of CC risk was compared to TT non-risk allele carriers (n=8 per group) (FIG. 2C). The relative amount of mtDNA was quantified by comparison of the mitochondrial MTCO2 gene with a nuclear target (18S) by qPCR. mtDNA content was given as ratio between mtDNA (MTCO2) and 18S. Isolation, culturing, and differentiation of primary human adipose progenitor cells were carried out as described above (section B2).

Oxygen Consumption Rate (OCR) in Primary Human Adipocytes

Figure 6G:
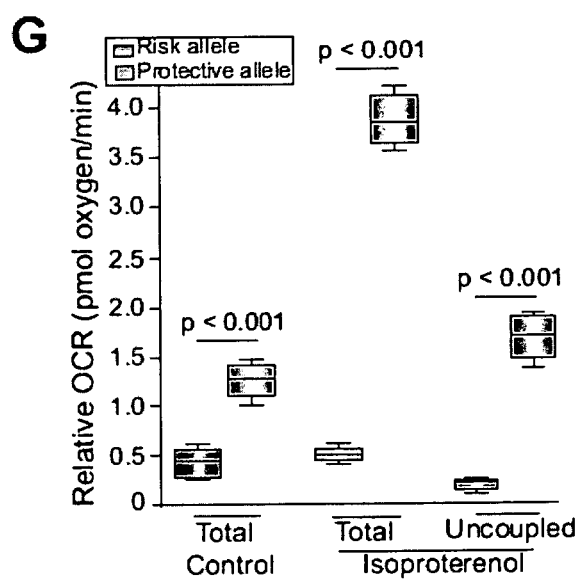

To assess directly effects of the rs1421085 on mitochondrial function, oxygen consumption rate (OCR) measurements were performed under basal and isoproterenol-stimulated conditions (FIG. 6G). Genotyped adipocyte progenitor cells isolated from BMI-matched persons were seeded (21 rs1421085 CC risk and 21 TT non-risk) at 70% confluence and induced to differentiate ($6 \times 10^4$ cells/well) the next day. On day 2 of differentiation, the medium was exchanged by XF Assay Medium (1 g/L glucose, 2 mM L-glutamine, 2 mM Na pyruvate) and 2% fatty acid-free BSA before 2 h incubation at 37° C. without $CO_2$. Cells were treated with isoproterenol (1 µmol/l) or DMSO (basal) for 4 hours. Total OCR was measured using the Seahorse XF24 (Seahorse Bioscience) and subtracted the minimum OCR level after rotenone/antimycin A treatment (5 µM) from the initial level without treatment, according to the manufacturer's protocol. Furthermore, to assess more directly effects on mitochondrial thermogenesis, uncoupled respiration (proton leak) was calculated by subtracting the minimum OCR level after rotenone/antimycin from the minimum level after oligomycin treatment (5 µM). The protocol was run with 3 min mixing and 2 min measuring. Isolation, culturing, and differentiation of primary human adipose progenitor cells were carried out as described above (section B2). The OCR method was re-used as described herein in sections C4 and D3.

Conditional Oxygen Consumption Rate Analyses in Primary Human Adipocytes

To establish causality, an ARID5B knock-down study was performed in primary human adipocytes of risk and nonrisk participants; oxygen consumption rate was measured conditional on the presence of ARID5B by qPCR (FIG. 10K). siRNA-mediated ARID5B knockdown was performed with ON-TARGET-plus SMARTpool siRNA (Dharmacon) and HiPerFect (Qiagen); ARID5B cDNA derived from SGBS total cDNA, which was inserted into the doxycycline-inducible Tet-on system (Tet-OnR Advanced Inducible Gene Expression System, BD Biosciences, Clontech, San Diego, Calif., USA) was used for over-expression. Sample preparation of primary human adipose cells, cDNA preparation, and qPCR analysis of IRX3 and IRX5 were carried out as described above (section B2).

Lipolysis Rate in Primary Human Adipocytes

Figures 10A, 10B:
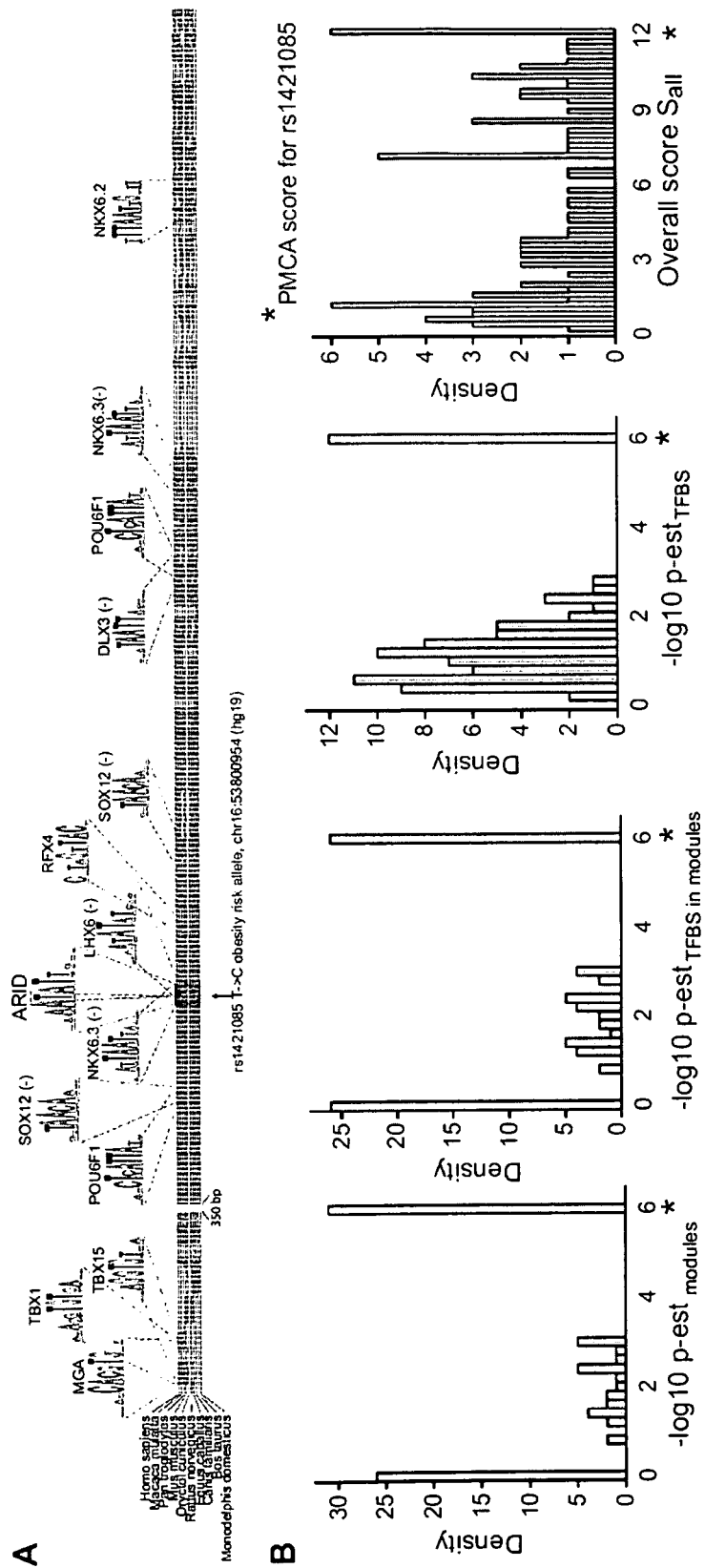
FIGS. 10A-10M. Regulatory circuitry of ARID5B, rs1421085, IRX3 and IRX5 in human adipocytes.
Figures 10C, 10D, 10E:
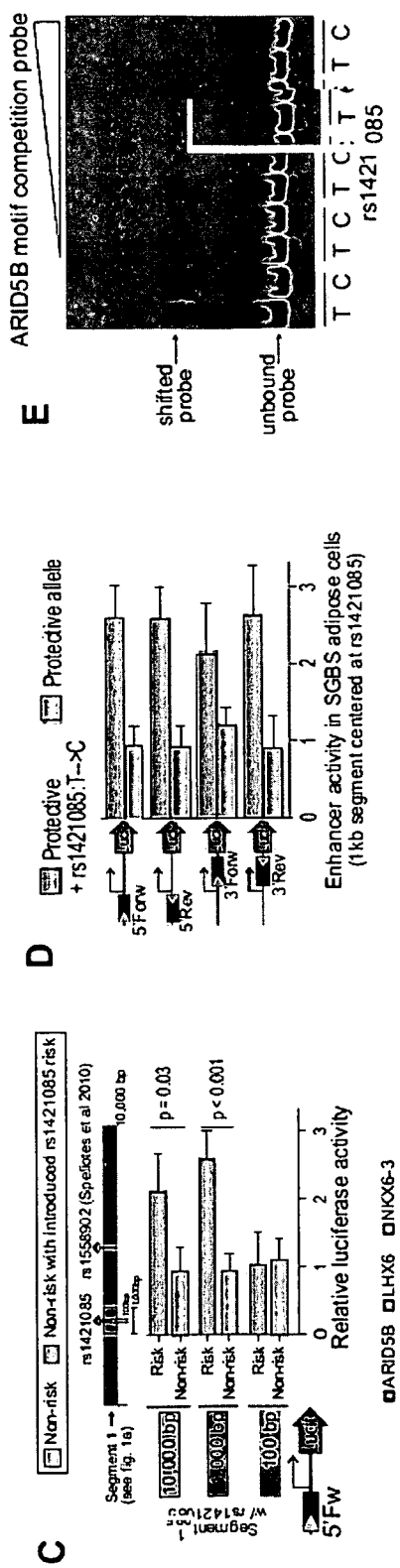
Figures 10F, 10G:
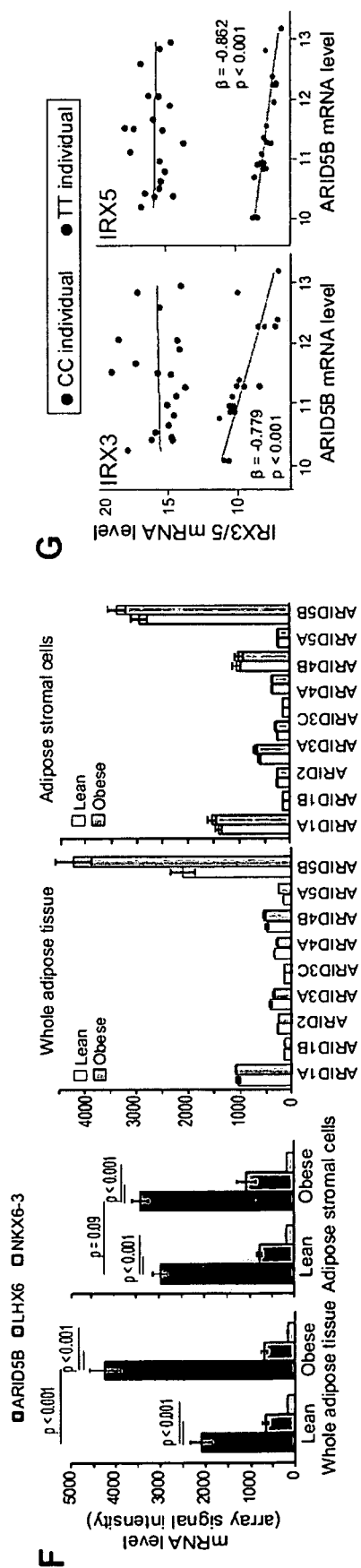
Figures 10H, 10I, 10J, 10K, 10L, 10M:
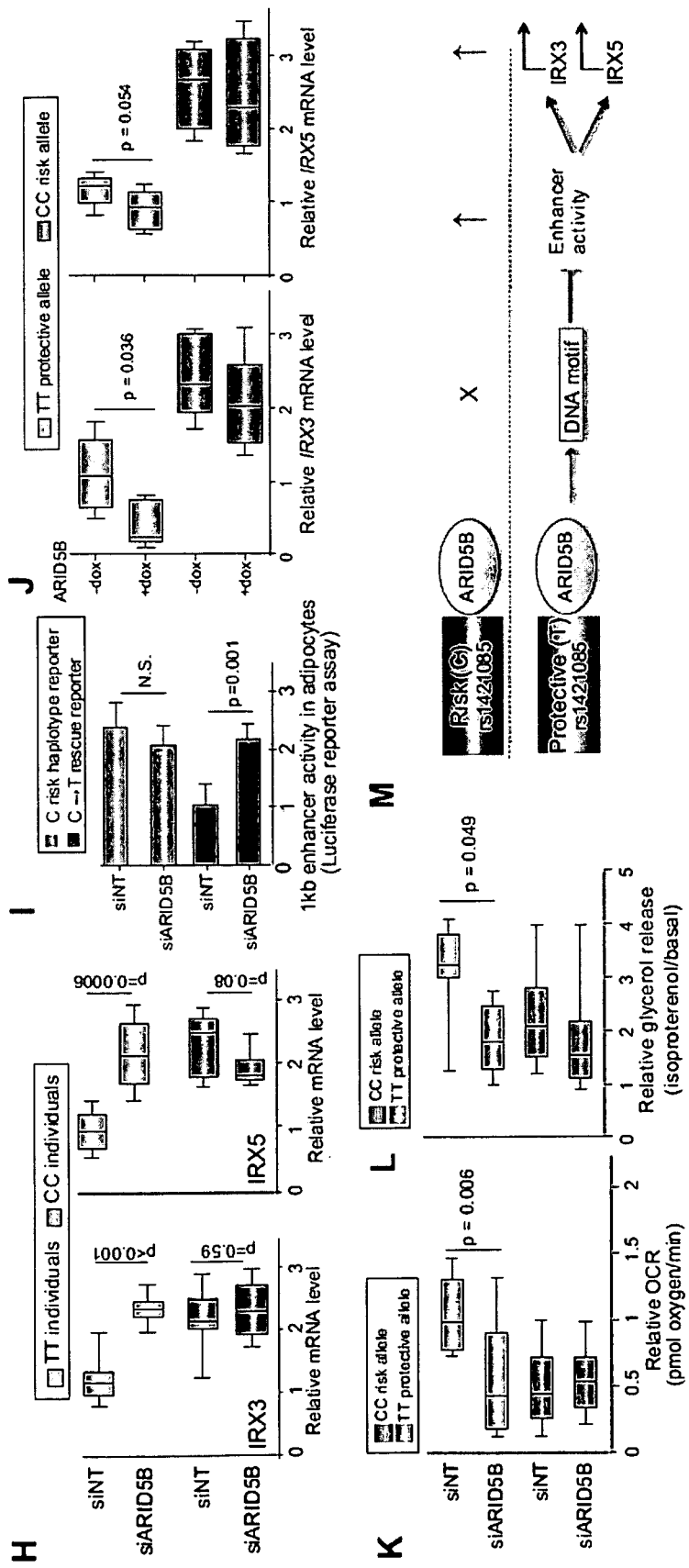

Since increased release of glycerol and free fatty acids from adipose cells through lipolysis may indicate reduced lipid storage (an anti-obesity phenotype), glycerol in the medium was measured after an 18-h incubation comparing primary human adipose cell cultures of risk (n=20) and non-risk (n=18) allele carriers (FIG. 10L). Glycerol was measured spectrophotometrically using a glycerol 3-phosphate oxidase trinder kit (Sigma). For stimulated lipolysis measurements, 1 µmol/l isoproterenol (Sigma) was added for 1 hour. Isolation, culturing, and differentiation of primary human adipose progenitor cells were carried out as described above (section B2).

D. Demonstrating Causal Roles for IRX3 and IRX5 in Adipocyte Thermogenesis and Obesity in Humans and Mice Having established that the obesity-associated genetic variants in the FTO locus are also associated with molecular and cellular differences in mitochondrial function and lipid storage, the effect of altered expression of target genes IRX3 and IRX5 on these phenotypes was examined by direct manipulation of IRX3 and IRX5 in humans and mice, followed by cellular and organismal phenotyping.

1. Validation of Molecular and Cellular Phenotypes of Thermogenesis in Humans

To examine causal roles for IRX3 and IRX5 on energy balance regulation in human adipocytes, the effect of their manipulation on downstream target gene expression and thermogenesis was quantified in primary human adipocytes from both risk and non-risk participants.

IRX3 and IRX5 Perturbations

To establish epistasis, IRX3 and IRX5 knock-down and overexpression in primary human adipocytes of homozygous risk (n=8) and homozygous non-risk (n=10) participants (FIG. 2D, FIG. 7A-7C) were employed. siRNA-mediated IRX3 and IRX5 knock-down was performed with ON-TARGET-plus SMARTpool siRNA (Dharmacon) or siRNA from Life Technologies for IRX3/5 and HiPerFect (Qiagen). For overexpression of IRX3 and IRX5, cDNAs derived from human SGBS total cDNA were inserted into the doxycyclineinducible Tet-on system (Tet-OnR Advanced Inducible Gene Expression System, BD Biosciences, Clontech, San Diego, Calif., USA). Isolation, culturing, and differentiation of primary human adipose progenitor cells were carried out as described above (section B2).

qPCR Validation of Causal Roles of IRX3 and IRX5 in Humans

Having established the genetic control of mitochondrial function and lipid accumulation of the FTO association with obesity, the causal role of IRX3 and IRX5 in target gene regulation was evaluated (FIG. 3A-3C). siRNA-mediated IRX3 and IRX5 knockdown and IRX3 and IRX5 overexpression were carried out in patient samples (n=18 homozygous non-risk, n=20 homozygous risk) and measured regulation of downstream targets by qPCR. Isolation, culture, and differentiation of primary human adipose progenitor cells were carried out as described above (section B2).

Oxygen Consumption Rate (OCR) after IRX3 and IRX5 Perturbations

To show that IRX3 and IRX5 levels recapitulate the impact of FTO genetic variant on thermogenesis and adipocyte browning, OCR was measured (FIG. 2D). First, siRNA mediated IRX3 and IRX5 knockdown, and IRX3 and IRX5 overexpression were carried out in patient samples. Both basal and isoproterenol-stimulated respiratory rate of primary human adipocytes from risk and non-risk participants (n=8 homozygous non-risk, n=10 homozygous risk) were measured. Cells were treated with isoproterenol (1 µmol/l) or DMSO (basal) for 4 hours. Total OCR was measured using the Seahorse XF24 (Seahorse Bioscience) and subtracted the minimum OCR level after rotenone/antimycin A treatment (5 µM) from the initial level without treatment. Isolation, culturing, and differentiation of primary human adipose progenitor cells and OCR assays are described in more detail herein in sections B2 and C3, respectively.

2. Anti-Obesity Effects of Irx3 Adipose Dominant Negative in Mice

Figures 8A, 8B, 8C, 8D:
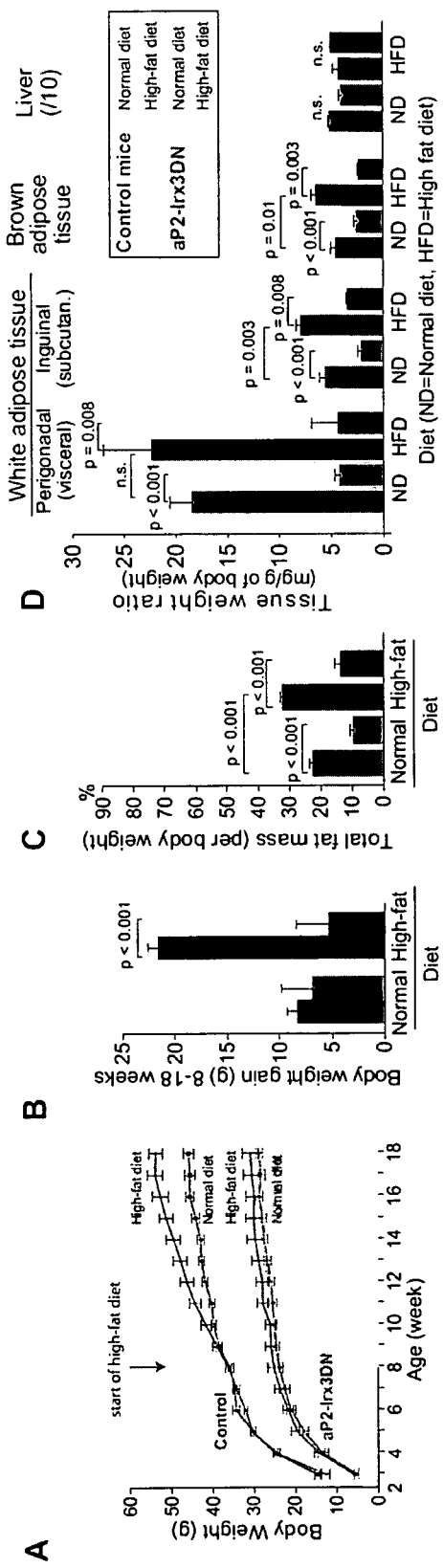

Having established the molecular and cellular phenotypic roles of IRX3 and IRX5, the effects of adipose repression of Irx3_at the organism level (FIG. 8A-8R) were examined. Adipose dominant negative Irx3 mice (aP2-Irx3DN) were used.

Generation of Mice

All animal studies were approved by Animal Care Committee of the Toronto Centre of Phenogenomics and conformed to the standards of the Canadian Council on Animal Care. Rosa26$^{EnR-Irx3}$ conditional transgenic mice (Irx3EnR) (Smemo et al., Nature 507:371-75, 2014), aP2-Cre mice (Shan et al., FASEB J. 27:277-87, 2013), and Irx3/5 double knockout mice were used, as described previously (Li et al., Dev. Cell 29:233-40, 2014). For generating adipose aP2-Irx3DN, aP2-Cre male mice were crossed with Rosa26$^{EnR-Irx3}$ homozygous female mice. We used Rosa26$^{EnR-Irx3}$ heterozygous mice as a control group to compare with Adipo-Irx3DN (aP2-Cre; Rosa26$^{EnR-Irx3}$) mice. Mice were genotyped by PCR assay using following sets of primers. The primer set for EnR-Irx3 transgene consists of ROSA-FP (5'-AAAGTCGCTCTGAGTTGTTAT-3' SEQ ID NO: 29), ROSA-WT-RP (5'-GGAGCGGGAGAAATGGATATG-3' SEQ ID NO: 30) and ROSA-MUT-RP (5'-GC-GAAGAGTTTGTCCTCAACC-3' SEQ ID NO: 31). The expected size of the specific PCR products are 600 base pair (bp) for wild-type and 350 bp for EnR-Irx3 transgene. The primer set for Cre gene are forward (5'-ATC-CGAAAAGAAAACGTTGA-3' SEQ ID NO: 32) and reverse (5'-ATCCAGGTTACGGATATAGT-3' SEQ ID NO: 33). The expected size of the PCR product is 600 bp. Only male mice were used in this study. Mice were maintained on 12-hour light/dark cycles and provided with food (Harlan #2918) and water ad libitum. For diet-induced obesity studies, 8 week old male mice were subjected to 45% high-fat diet (Research Diets) for 10 weeks. Body weight was measured every week from 3 to 18 weeks of age (FIG. 8A-8F, 8J-8K, 8P).

Histological Analysis

Figures 8E, 8F, 8G:
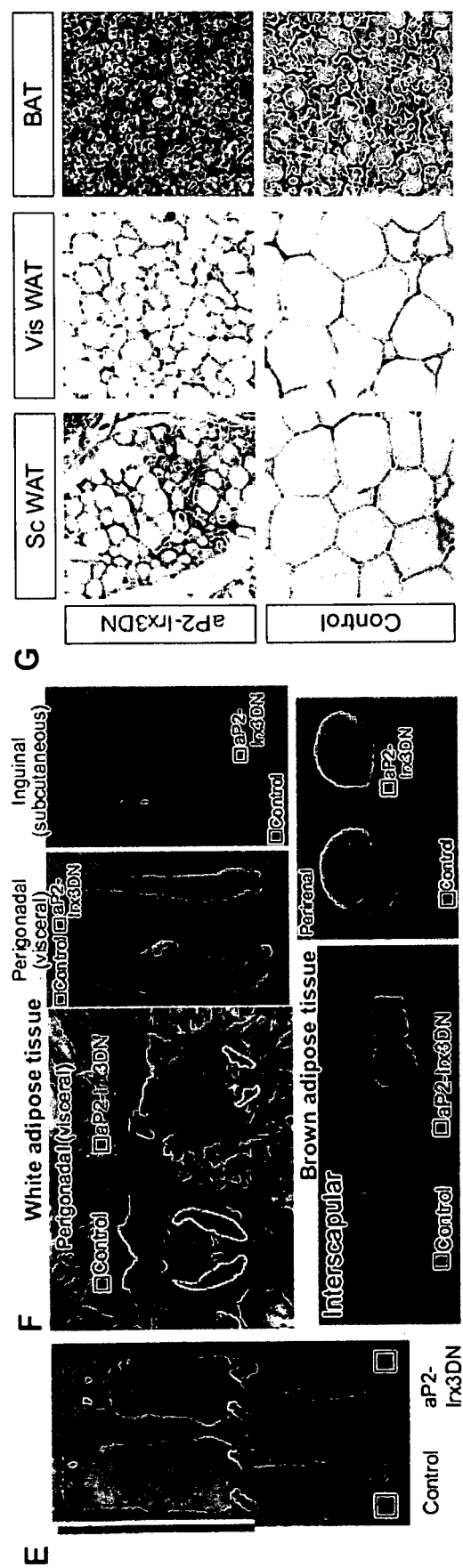
FIG. 8E shows reduced body size of aP2-Irx3DN transgenic mice expressing a dominant negative form of Irx3 in adipose cells (aP2-Cre; Irx3EnR).
FIG. 8F shows reduced adipose tissue mass in aP2-Irx3DN vs. controls measured at 18 weeks of age after a high-fat diet introduced at 8 weeks.
FIG. 8G shows 4-fold reduced adipocyte size in white and brown fat sections upon high-fat diet for aP2-Irx3DN mice vs. control.

After assessment of energy metabolism, mice were sacrificed to harvest tissues for organ weight measurement, gene expression analysis and histological analysis (FIG. 8G). For histological analysis, tissues were fixed in 4% paraformaldehyde and embedded in paraffin. Hematoxylin and eosin (H&E) were used for staining of 5 µm sections.

Metabolic Phenotyping

Figures 8H, 8I, 8J, 8K, 8L:
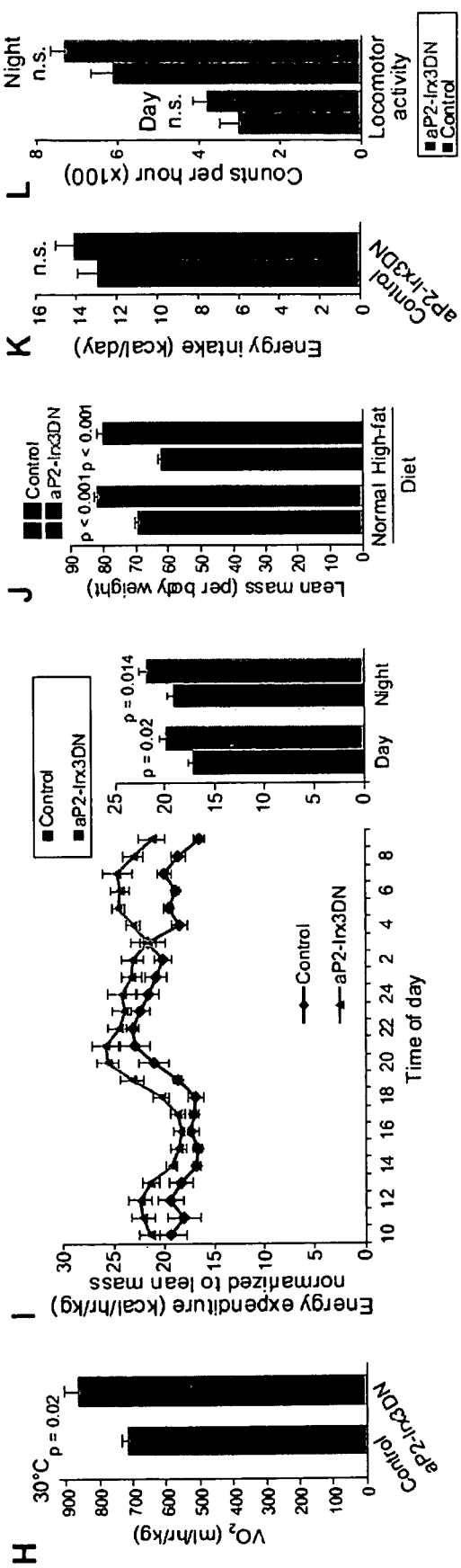
FIG. 8H shows increased energy expenditure for aP2-Irx3DN mice vs. controls after 8 days at thermoneutrality (30° C.), measured by indirect calorimetry (n=3 per group).
FIG. 8I shows increased oxygen consumption in aP2-Irx3DN vs. controls (normalized to lean mass), a marker of increased energy expenditure. Difference is seen both during the day and during the night, indicating that it is not due to increased locomotor activity.
FIG. 8J shows increased fraction of lean mass per body weight in aP2-Irx3DN mice vs. controls.
FIG. 8K shows unchanged energy intake in aP2-Irx3DN mice vs. controls.
FIG. 8L shows unchanged locomotor activity in aP2-Irx3DN mice vs. controls.

To examine body composition by measuring fat and lean mass as well as free water, 18 week old mice were subjected to an ECHOMRI™ device (Echo Medical Systems). Indirect calorimetry (Oxymax System, Columbus Instruments) was used to measure energy metabolism of the mice. Each mouse was added to the airtight chamber and provided with about 20 g of chow and water bottle. From measurement over periods of 24 hours, oxygen consumption ($VO_2$), carbon dioxide production ($VCO_2$), respiratory exchange ratio ($RER=VCO_2/VO_2$) were recorded from each chamber every 15 minutes (FIG. 8I). Locomotor activity of each mouse was simultaneously measured using the break counts of infrared beams (FIG. 8L). Energy expenditure was calculated by multiplying oxygen consumption ($VO_2$) by the calorific value ($CV=3.815+1.232 \times$ respiratory exchange ratio) and normalized by lean mass measured by a ECHOMRI™ (FIG. 8J). After 24 hours of measurement, the amount of food left in the cage was weighed to calculate food intake (FIG. 8K).

Thermoneutrality $VO_2$ Measurements

For a mouse, room temperature (22° C.) is a cold stress, requiring increased heat generation to maintain body temperature, compared to mice in the thermoneutral zone (30° C.). The smaller body size in AdipoIrx3DN mice could lead to the development of a browning phenotype due to higher heat loss. To exclude this possibility and to ensure measurement of energy expenditure without thermal stress, energy expenditure was measured in mice adapted to thermoneutrality (FIG. 8H). Mice were housed at 30° C. for 8 days with free access to food and water. After acclimation under thermoneutral condition, mice were subjected to anesthesia (sodium pentoabarbital, 66 mg/kg i.p.) to exclude potential influence from physical activity. $O_2$ consumption ($VO_2$) was then measured using the indirect calorimeter and normalized with lean mass.

Figures 8M, 8N:
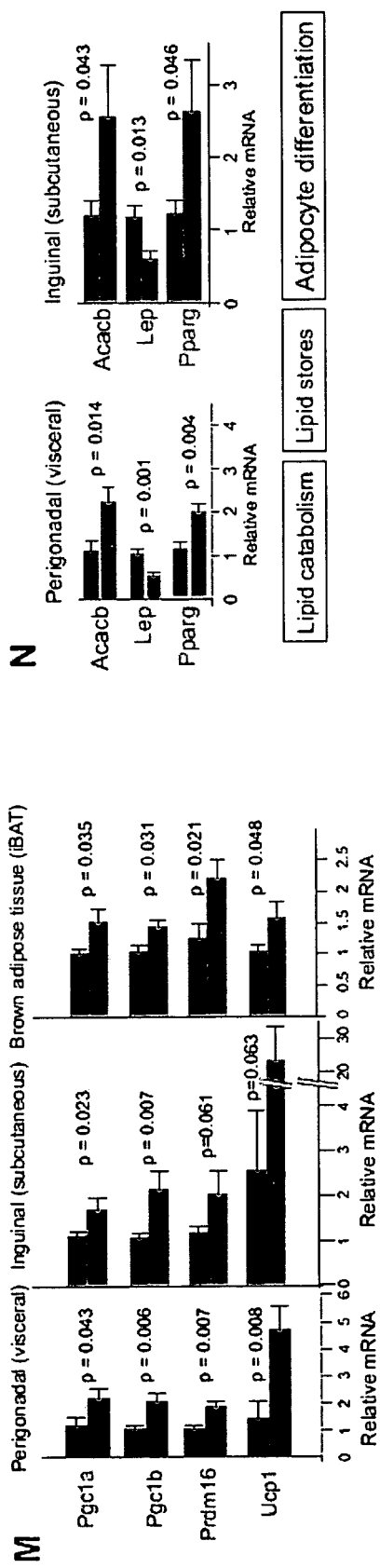
FIG. 8M shows increased expression of mitochondrial function genes in adipose tissues of aP2-Irx3DN mice vs. controls.
FIG. 8N shows increased expression of lipid catabolism marker Acacb in aP2-Irx3DN mice vs. controls, decreased expression of lipid storage marker Lep, and increased expression of adipocyte differentiation marker Pparg, measured by qPCR with normalization to β-actin (Actb) mRNA. (n=9-11).

Targeted qPCR Analysis of Energy Balance Regulators in Adipose Dominant Negative Irx3 Mice Versus Littermate Controls RNA was extracted using TRIZOL® (Invitrogen) from different adipose tissue depots of the aP2-Irx3DN mice and controls, including perigonadal, inguinal and brown adipose tissue and measured mRNA levels from regulators of mitochondrial function, thermogenesis, lipid catabolism, lipid stores, and adipocyte differentiation (FIGS. 8M and 8N). We synthesized cDNA with High-Capacity cDNA Reverse Transcription Kit (Applied Biosystems). qPCR was performed using SYBR™ Green with 60° C. annealing temperature and calculated relative gene expression by the standard delta delta Ct method. Target gene expression was normalized to expression of Actb (mouse).

qPCR Analysis of EnR in Different Tissues

Figures 8O, 8P, 8Q, 8R:
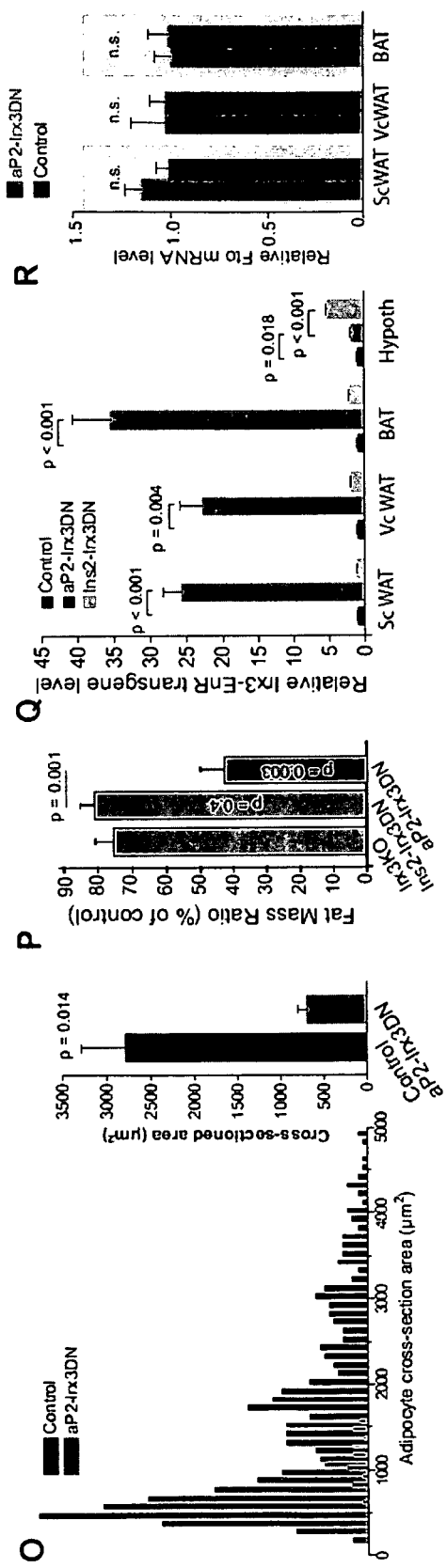

To evaluate expression of Adipo-IRX3DN adipose-specific dominant negative Irx3-EnR transgene in all measured adipose tissues, and robust expression of Hypo-IRX3DN hypothalamus-specific dominant negative Irx3-EnrR transgene in Hypothalamus, but without significant expression in the wrong tissues, qPCR analysis of EnR mRNA levels was performed in the respective tissue from adipose dominant negative aP2-Irx3DN mice and hypothalamus dominant Ins2-Irx3DN mice (Smemo et al., Nature 507:371-75, 2014) (FIG. 8Q).

Adipocyte Size Measurements in Adipose Dominant Negative Irx3 Mice Versus Littermate Controls The size of an adipocyte as cross-sectional surface area was measured using Image J by manual tracing of inguinal adipocytes on three randomly selected hematoxylin and eosin (H&E or HE) stained sections per mouse (FIG. 8O). Histological analysis was performed as described herein (section D2). Histograms of adipocyte cross-sectional area were analyzed using Origin 8.0.

3. Validation of Energy Balance Phenotypes Using Irx3 and Irx5 Manipulations in Mouse Adipocytes To confirm tissue-autonomous effects of Irx3 and Irx5 on energy balance, the effects of Irx3 and Irx5 knockout and overexpression on lipid accumulation and/or UCP1 activation were evaluated in three cellular mouse models (FIG. 9A-9E). First, a double knock-out of Irx3 and Irx5 was performed; mouse embryonic fibroblasts (MEFs) was extracted and differentiated in vitro into adipocytes. Second, Irx3 and Irx5 were overexpressed in mouse 3T3-L1 preadipocytes and differentiated in vitro. Third, to examine a causal role of IRX3 and IRX5 in mitochondrial thermogenesis repression, ME3 cells were used as a model of beige adipocytes. IRX3 and IRX5 were overexpressed in ME3 cells and UCP1 reporter studies were performed.

Mouse Embryonic Fibroblasts (MEFs) from Irx3/Irx5 Knockout Mice

Figures 9A, 9B, 9C, 9D, 9E:
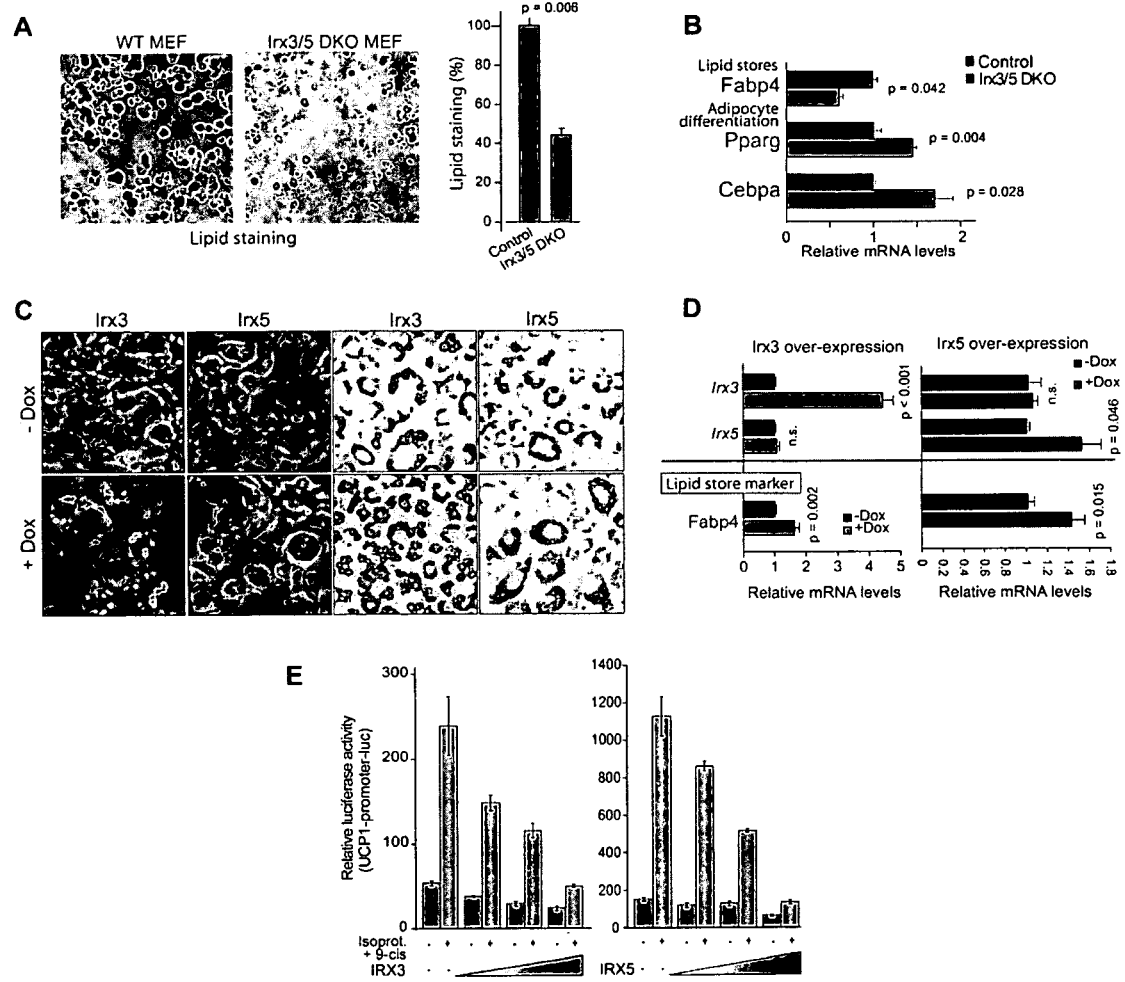
FIGS. 9A-9E. Cell-autonomous regulation of obesity phenotypes by Irx3 and Irx5 in mouse adipocytes.

MEFs were isolated from E14.5 embryos of wild-type and Irx3/5 double knockout mice, as described previously (Li et al., Development 139:4152-61, 2012). MEFs were cultured in DMEM supplemented with 10% fetal bovine serum (FBS). Two days after cells become 100% confluent, either 3T3-L1 cells or MEFs were induced to differentiate into adipocytes by administrating DMEM containing 10% FBS, 500 μM 3-isobutyl-1-methylxanthine, 1 μM dexamethasone, and 10 μg/ml insulin. Two days after induction, cells were switched to the maintenance medium containing 10% FBS and 10 μg/ml insulin and cultured for 6-8 more days (up to 8-10 days after differentiation induction). Subsequently cells were stained with Oil Red 0 to examine lipid accumulation (FIG. 9A) or were harvested for gene expression analysis (FIG. 9B).

Over-Expression of Irx3 and Irx3 in 3T3-L1 Pre-Adipocytes

3T3-L1 preadipocytes were cultured in DMEM supplemented with 10% fetal bovine serum (FBS). Overexpression of Irx3 and Irx5 was achieved in 3T3-L1 cells by either piggyBAC™ transposon system (Woltjen et al., Nature 458:766-70, 2009) or infection with adenovirus carrying Irx3 or Irx5. For piggyBAC™transposon-mediated overexpression, cDNAs encoding Irx3 and Irx5 were subcloned into the PB-TAC vector. Then a mixture of the PB-TAC, PB-RB (i.e. the reverse tetracycline transactivator) and PBase (i.e. PB transposase) plasmids was transfected at a ratio of 5:1:1 into undifferentiated 3T3-L1 cells. One day after transfection, drug selection was begun with puromycin and G418 (Geneticin) and continued until the end of the experiment. When cells were 80% confluent, 1 μg/mL doxycycline was added to culture media in order to induce Irx3 and Irx5 overexpression and maintained throughout the experiment. For adenovirus-mediated overexpression, 3T3-L1 cells were infected with adenovirus at multiplicity of infection (MOI) of 50, when cells reached confluence. After overnight infection, cells were washed and added with fresh culture media. Two days after cells become 100% confluent, 3T3-L1 cells were induced to differentiate to adipocytes by administrating DMEM containing 10% FBS, 500 μM 3-isobutyl-1-methylxanthine, 1 μM dexamethasone, and 10 μg/ml insulin. Two days after induction, cells were switched to the maintenance medium containing 10% FBS and 10 μg/ml insulin and cultured for 6-8 more days (up to 8-10 days after differentiation induction). Then cells were stained with Oil Red O to examine lipid accumulation (FIG. 9C) or were harvested for gene expression analysis (FIG. 9D).

ME3 Cells Over Expressing IRX3 and IRX5

ME3 cells were derived from RB−/− mouse embryos, as a model of beige adipocytes (Lukas et la., Mol. Cell Biol. 15:2600-11, 1995; Hansen et al., PNAS 101:4112-17, 2004). Cells were cultured in AMNIOMAX® C100 basal medium (Life Technologies) containing 7.5% AMNIOMAX® C100 Supplement (Life Technologies), 7.5% foetal bovine serum (FBS) (Life Technologies), 2 mM L-glutamine (Lonza) and Penicillin-Streptomycin (Sigma-Aldrich). On day 0, 50,000 cells were seeded in each well of a 24-well plate. Cells were transfected on day 1 using Superfect Transfection Reagent (Qiagen) and OPTI-MEM® Reduced Serum Medium (Life Technologies), with 0.5 μg pGL3 Basic UCP1 reporter plasmid and three different concentrations (0.1 μg, 0.5 μg and 1.0 μg) of pCMV6-XL5 IRX5 (SC128090, Origene) or pCMV6-AC IRX3 (SC319551, Origene). The total concentration of plasmid was adjusted using the empty vector pCMV6-XL4 (pCMV6-XL4, Origene). UCP1 expression was induced with 100 nM isoproterenol (Sigma-Aldrich) and 1 μM 9-cis-retinoic acid (Sigma-Aldrich). Controls were given an equivalent volume of DMSO. All experiments were performed in triplicate. Cells were lysed with a buffer containing 10% glycerol, 25 mM TAE (pH 7.8), 1% Triton X100, 1 mM EDTA and 2 mM DTT. Luciferase activity was measured using FLUOSTAR® Optima (BMG Labtech) according to manufacturer's protocol, with 50 μl ATP Substrate (Bio-Thema) and Luciferin Substrate (BioThema) added to each well (FIG. 9E).

E. Identification and Validation of the Causal Variant Rs1421085

Given that the resolution of GWAS is limited by the haplotype structure of the human genome (a common variant in the population is usually strongly genetically linked to dozens of neighboring variants), the probability that the reported marker SNP of the FTO locus is indeed the causal SNP driving the phenotypic association with obesity was confirmed (the FTO obesity locus harbors 89 common variants in high linkage disequilibrium). The causal variant underlying the FTO association with obesity was confirmed.

1. Computational Prediction of Causal Nucleotide

To predict the causal variant that confers the increased risk of obesity in the population, several conservation scores were used based on a phylogenetic framework, i.e. Phylogenetic Module Complexity Analysis (PMCA) (Claussnitzer et al., Cell 156:343-58, 2014), which analyses evolutionary conservation of cis-regulatory modules across related species. Consistent with the chromatin state annotations across 127 human cell types and our tiling experiments, the highest Phylogenetic Module Complexity Analysis (PMCA) scores occur in the first 10 kb interval of the locus. The conservation analysis predicted variant rs1421085 at position chr16: 53,800,954 (hg19) as a conserved motif module with the highest score of any of the non-coding variants.

PMCA Functional Conservation Analysis

Figures 3A, 3B, 3C, 3D:
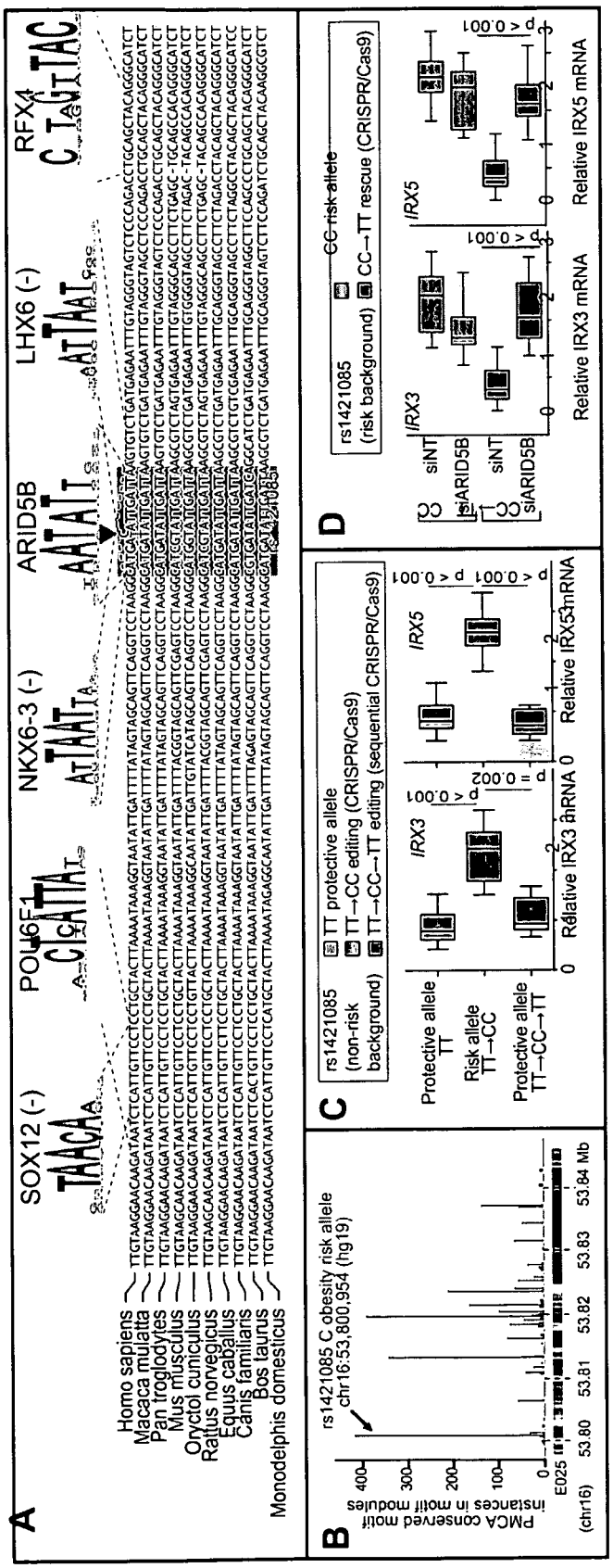
FIGS. 3A-3D. Causal nucleotide rs1421085 disrupts a conserved ARID5B repressor motif in humans.

To predict the causal variant underlying the FTO association with obesity, the PMCA method described in (Claussnitzer et al., Cell 156:343-58, 2014) was used with several modifications. Briefly, 972 position weight matrices grouped in 192 motif matrix families (Cartharius et al., Bioinformatics 21:2933-42, 2005) (Genomatix, Munich, Germany) were used to scan variant-flanking regions of the human reference genome (variant at mid-position) and its orthologous regions for cross-species functionally conserved motif modules (a module is defined as a set of binding site motifs, whose order and distance range is conserved across species) (Claussnitzer et al., Cell 156:343-58, 2014). See FIG. 3A and FIG. 10A (showing comparison for *Homo sapiens* with *Macaca mulatta*, *Pan troglodytes*, *Mus musculus*, *Oryctol cuniculus*, *Rattus norvegicus*, *Equus caballus*, *Canis familiaris*, *Bos taurus*, and *Monodelphis domesticus*). This method counts instances of conserved single motifs, motifs within conserved modules and conserved modules within a variant flanking region and computes the enrichment for any of those features using randomizations of orthologous sets (120 bp centered on the variant) (FIG. 3B, FIG. 10B). Randomizations were done by local shuffling and an experimentally validated scoring scheme was applied as described in Claussnitzer et al., Cell 156:343-58, 2014, with the following modification: background probabilities were computed using a set of 10,000 shuffled orthologous sequence sets.

2. Experimental Validation that Predicted Nucleotide Alters Enhancer Activity

To validate that the single-nucleotide T-to-C rs1421085 alteration leads to a robust and reliable increase in enhancer activity, enhancer luciferase assays were used in human SGBS adipocytes for elements of varying sizes (FIG. 10C) and cloned in different orientations (FIG. 10D) in the reporter gene construct.

Allelic Enhancer Activity Assays for Elements of Varying Sizes

To assay the enhancer context of rs1421085 allelic activity, fragments of different sizes were synthesized, including a 10 kb, 1000 bp and 100 bp fragment encompassing rs1421085 at mid-position (segment 1_10 kb: chr16: 53799507-53809507; segment 1_1 kb: chr 16:53800454-53801454; segment 1_100 bp: chr16: 53800904-53801004) (FIG. 10C). 10 kb and 1000 bp regions were synthesized as plasmid vectors (Life Technologies) and 100 bp as double-stranded oligonucleotides (MWG, Germany). Complementary oligonucleotides were annealed and purified on a 12% polyacrylamide gel. For each of these fragments, constructs carrying both alternate alleles were generated.

Cloning of Constructs with Elements of Varying Sizes

Genomic DNA segments with three different sizes (100 bp, 1 kb, 10 kb) were subcloned upstream of the TK promoter into the KpnI and SacI sites of the pGL4.22-TK vector in forward orientation as described above (section A2). Site-directed mutagenesis (QUICKCHANGE® II Site-Directed Mutagenesis Kit, Stratagene) was performed to introduce the T-to-C substitution in the 10 kb and 1000 bp fragments. The identity of each construct clone was verified by DNA sequencing. Transfection in human SGBS adipocytes was performed and enhancer activity was measured as described herein above (section A2).

Allelic Enhancer Activity Assays with Elements in Different Orientations

To confirm enhancer function of the rs1421085 surrounding regulatory region for the C risk allele, reporter gene construct that harbors the identified enhancer element in the forward or reverse orientation and upstream or downstream orientation of the reporter gene was used (FIG. 10D).

Cloning of Constructs in Different Orientations to the Luciferase Gene

Genomic DNA segments were subcloned either upstream of the TK promoter into the KpnI and SacI sites of the pGL4.22-TK vector or downstream of the luciferase gene into the BamHI site of the pGL4.22-TK vector in both forward and reverse orientations. Site-directed mutagenesis (QUICKCHANGE® II Site-Directed Mutagenesis Kit, Stratagene) was used to introduce the T-to-C substitution in the non-risk background. The identity of each construct clone was verified by DNA sequencing. Transfection was performed in human SGBS adipocytes as described herein above (section A2).

3. Experimental Validation that Predicted Nucleotide Alters Transcription Factor Binding To test if the risk allelic enhancer activity and increase in IRX3 and IRX5 expression is provoked by differential transcription factor binding, Electrophoretic Mobility Shift Assays (EMSA) was performed using adipocytic nuclear extract.

Electrophoretic Mobility Shift Assays (EMSA)

To test if the variant rs1421085 shows allele-specific binding transcriptional regulators electrophoretic mobility shift assays (EMSA) was performed using the rs1421085 surrounding sequence in the two allelic forms (FIG. 10E). EMSA was performed with Cy5-labelled oligonucleotide probes. rs1421085-flanking region oligonucleotides were commercially synthesized containing either the risk or the protective allele (MWG). Cy5-labelled forward strands were annealed with non-labeled reverse strands, and the double-stranded probes were separated from single-stranded oligonucleotides on a 12% polyacrylamide gel. Complete separation was visualized by DNA shading. The efficiency of the labeling was tested by a dot plot, which confirmed that all of the primers were labeled similarly. Nuclear protein extracts were prepared from SGBS human adipose cells with adapted protocols based on the method described in Claussnitzer et al., Cell 156:343-58, 2014. The supernatant was recovered and stored at −80° C. DNA-protein binding reactions were conducted in 50 mM Tris-HCl, 250 mM NaCl, 5 mM $MgCl_2$, 2.5 mM EDTA, 2.5 mM DTT, 20% v/v glycerol and the appropriate concentrations of poly (dI-dC). For DNA-protein interactions, 3-5 µg of nuclear protein extract from the respective cell line was incubated for 10 min on ice, and added Cy-5-labelled genotype-specific DNA probe for another 20 min.

F. Prediction and Validation of the Upstream Regulator ARID5B

Hypothesizing that the rs1421085 T-to-C substitution alters a transcription factor binding site motif, conservation algorithms were used to predict the binding regulator and expression and enhancer assays were performed to validate the causal role of the binding regulator.

1. Computational Prediction of Candidate Regulators Based on Motif Matches

To establish the binding regulator, the sequence surrounding rs1421085 was analyzed and searched for evolutionary conserved transcription factor binding site (TFBS) motif modules across mammalian species and determined disturbed TFBS motifs as described herein above (section D1).

2. Expression-Based Prediction of Likely Causal Regulator in Humans

Given that the T-to-C substitution at rs1421085 disrupts three AT-rich regulatory motifs for NKX6-2, LHX6, and the ARID (AT-rich interaction domain) motif family, suggesting them as putative upstream regulators, gene expression analysis was performed in whole human adipose tissue biopsies and isolated human adipose progenitor cells (FIGS. 10F and 10G). Subsequently, diverse members of the ARID family of transcription factors were tested for the expression patterns.

Microarray Analysis in Whole Adipose Tissue and Isolated Primary Human Adipocyte Progenitor Cells Global gene expression was measured in whole abdominal subcutaneous adipose tissue from 13 lean and 17 obese persons using Illumina HumanRef-8 v. 3 BeadChip microarrays, as described previously (Dankel et al., PLoS One 5:e11033, 2010) (FIG. 10F). For isolated human adipose progenitor cells from human abdominal subcutaneous adipose tissue (12 lean and 12 obese persons), about 700-800 mg of tissue was fractionated by collagenase immediately after biopsy collection, as described previously (Methlie et al., Obesity (Silver Spring) 21:2495-503, 2013). See FIG. 10F. The human adipose progenitor cells were analyzed by Illumina HumanHT-12 v. 3 BeadChip microarrays. Signal intensities were quantile normalized.

Sample Preparation for Microarray Analyses

Total RNA was extracted with RNEASY® Lipid Tissue Kit (Qiagen).

qPCR-Based Correlation Analysis of IRX3/IRX5 with ARID5B

The correlation of gene expression of IRX3 and IRX5 was analyzed with ARID5B in isolated human adipose progenitor cells from 18 participants carrying the TT homozygous non-risk allele haplotype and 20 patients carrying the CC risk haplotype (FIG. 10G).

Sample Preparation for qPCR Analysis

Total RNA was extracted with TRIZOL® (Invitrogen). Copy DNA (cDNA) was synthesized with High-Capacity cDNA Reverse Transcription Kit (Applied Biosystems) as described above (section B2). qPCR was performed using SYBR™ Green with 60 C annealing temperature. Relative gene expression was calculated by the delta delta Ct method. We normalized target gene expression to expression of HPRT12 or TBP (human). All genotyping was done for both the GWAS reported tag SNP and the identified variant rs1421085.

3. Experimental Validation of the Predicted Regulator ARID5B in Human Cells

To validate the repressor function of ARID5B specifically for the rs1421085 non-risk allele, cis/trans conditional enhancer assays and cis/trans endogenous gene expression analyses were performed in primary human adipocytes from patients and controls (FIG. 10H-10J, regulatory model in FIG. 10M).

Conditional Gene Expression Analyses in Primary Human Adipocytes

To establish causality, ARID5B knock-down (FIG. 10H) and overexpression (FIG. 10J) in primary human adipocytes of risk and non-risk participants were performed, and regulation of IRX3 and IRX5 and regulation of downstream targets conditional on the presence of ARID5B by qPCR were assessed. siRNA-mediated ARID5B knock-down was performed with ON-TARGET-plus SMARTpool siRNA (Dharmacon) and HiPerFect (Qiagen), and overexpression was performed with ARID5B cDNA derived from SGBS total cDNA, which was inserted into the doxycycline-inducible Tet-on system (Tet-OnR Advanced Inducible Gene Expression System, BD Biosciences, Clontech, San Diego, Calif., USA). Sample preparation of primary human adipose cells, cDNA preparation, and qPCR analysis of IRX3 and IRX5 were carried out as described herein above (section B2).

Conditional Enhancer Activity Assays

To test for a causal role of ARID5B in regulating the enhancer at the FTO obesity locus, ARID5B knock-down enhancer studies were performed. siRNA-mediated ARID5B knock-down was performed with ON-TARGET-plus SMARTpool siRNA (Dharmacon) or siRNA from Life Technologies for IRX3/5 and HiPerFect (Qiagen) (FIG. 10I). Enhancer activity assays were performed as described above (section A2).

4. Experimental Validation of Regulator Binding

To further validate that ARID5B is the binding repressor, competition experiments were performed where the labeled DNA-protein complex is competed away by increasing concentrations of unlabeled oligonucleotides containing the ARID5B consensus sequence (FIG. 10E).

EMSA Competition Experiments

EMSA assay was performed as described herein above (section D3). For competition experiments 11-, 33- and 100-fold molar excess of unlabeled probe as competitor was included with the reaction prior to addition of Cy5-labeled DNA probes (FIG. 10E). Binding reactions were incubated for 20 min at 4° C. The DNA-protein complexes were resolved on a nondenaturation 5.3% polyacrylamide gel in 0.5×Tris/borate/EDTA buffer. Fluorescence was visualized with a Typhoon TRIO+ imager (GE Healthcare, Germany).

G. Validation of Variant Causality by Genome Editing

The effect of the single-nucleotide alteration in its endogenous context (e.g., effect of ARID5B binding; IRX3 and IRX5 expression; effect on mitochondrial function, thermogenesis and adipocyte browning—the effect on the mechanistic model) was demonstrated to establish causality using CRISPR/Cas9 genome editing in primary human patient samples (FIGS. 3C and 3D, FIG. 4A-4C).

1. Genome Editing Methodology

CRISPR/Cas9 Genome Editing

To establish causality of the single-nucleotide alteration in its endogenous context for obesity cellular phenotypes, CRISPR/Cas9 genome editing was performed in primary human adipose cells to alter the rs1421085 single-nucleotide polymorphism (SNP) from TT non-risk allele to CC risk allele and vice versa. The hCas9 plasmid and the guide RNAs (gRNA) cloning vector were purchased from Addgene. To change the T to the C allele and the C to the T allele, respectively, we performed Site-directed Mutagenesis using the Q5R Site-Directed Mutagenesis Kit (New England Biolabs). The mutagenesis primer 5'-TAAGGCATGACATTGATTAAGTGTC-3' (SEQ ID NO: 34) was used, both forward and reverse. To exclude off-target effects, reversion was carried out after initial editing with a separate guide RNA. Synthetic guide RNAs (sgRNAs) were designed using the CRISPR design online tool from the Zhang lab (crispr_mit_edu). The following guide RNAs were used: 5' CAC-CGCTGGAAGGAACGCGTTTGTT-3' (SEQ ID NO: 27), 5'-CACCGGGACAGTGCGTAGACTAAAC-3' (SEQ ID NO: 28). For transfection, GFP and Cas9 were cotransfected with sgRNAs, the homology vector, and pMACS plasmid 4.1 (Miltenyi Biotec, Cambridge, Mass.) in human adipose progenitor cells using the AMAXA® NUCLEOFECTOR® device (program U-033) (Lonza Group Ltd., Portsmouth, N.H.). Cells were sorted using the MACSelect™ Transfected Cell Selection cell sorting kit (Miltenyi Biotec, Cambridge, Mass.). Sorted cells were cultured for 3-5 days and clones propagated from a single cell were picked out. Nucleotide exchange was confirmed by DNA sequencing.

2. Bi-Directional Editing of Risk and Non-Risk Adipocytes

Bi-directional editing of the rs1421085 variant was performed using CRISPR/Cas9 genome editing from both the protective and the risk allele. The study was begun from isolated adipose-derived mesenchymal cells from one patient carrying the non-risk haplotype (FIG. 3C). The converse editing event was also carried out, starting with a CC homozygous risk participant (FIG. 3D). Genomic DNA was amplified from the respective rs1421085 CC risk allele carrier and TT nonrisk allele carrier. Genome editing was performed as described herein above (section G1).

3. Establishment of Causality for Repression and Temporal Context Dependency

Figures 4A, 4B, 4C, 4D:
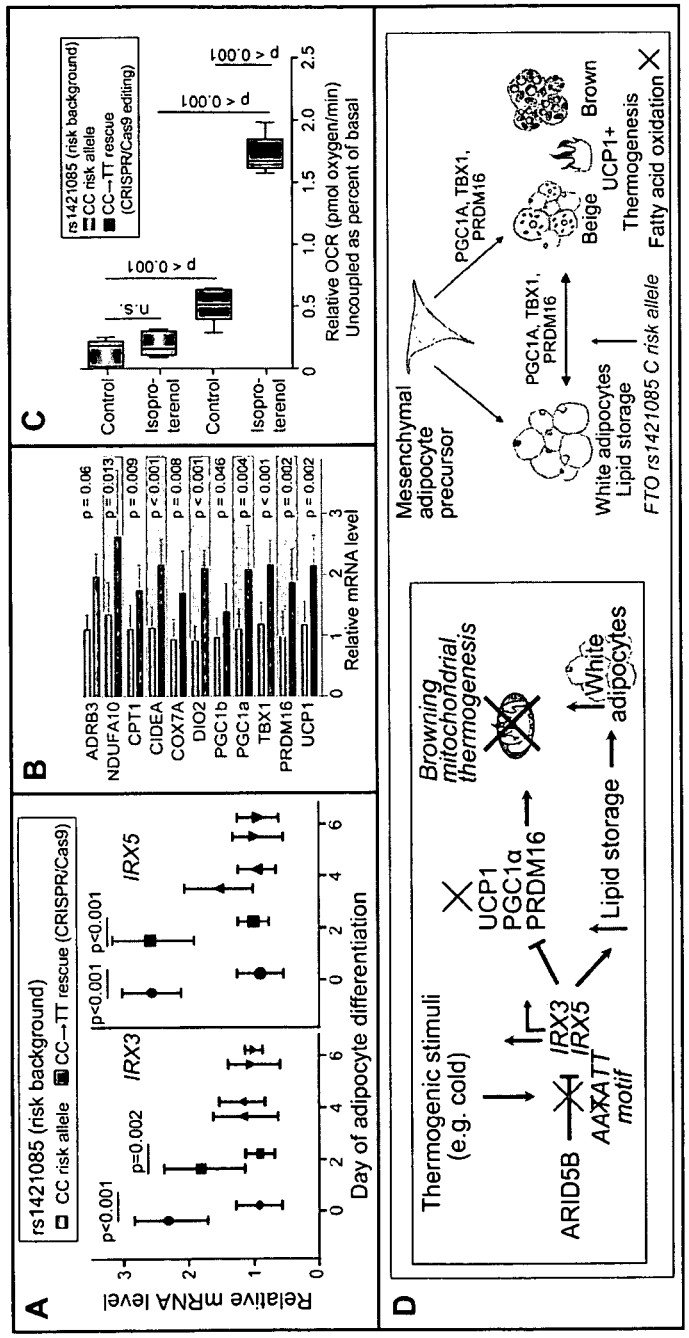
FIGS. 4A-4D. Editing of SNV rs1421085 in a patient at risk rescues metabolic effects on adipocyte energy consumption.

To confirm that ARID5B is necessary for the repression of IRX3 and IRX5, specifically for the C-to-T rescued allele, conditional analysis of single-nucleotide editing and knock-down of the upstream regulator ARID5B were performed (mechanistic model in FIG. 4D).

Conditional Gene Expression Analyses in CRISPR/Cas9 Edited Primary Human Adipocytes To establish repressor causality, ARID5B knock-down was carried out in the CRISPR/Cas9 edited patient cells and measured regulation of IRX3 and IRX5 conditional on the presence of ARID5B by qPCR (FIG. 3D). C-to-T editing was performed by CRISPR/Cas9 as described herein above (section F1). siRNA-mediated ARID5B knock-down was performed with ONTARGET-plus SMARTpool siRNA (Dharmacon) and HiPerFect (Qiagen). Sample preparation of primary human adipose cells, cDNA preparation, and qPCR analysis were carried out as described herein above (section B2).

Temporal Dynamics of Rs1421085 Allelic Activity on IRX3 and IRX3 Expression in CRISPR/Cas9 Edited Cells from a Risk Allele Carrier C-to-T editing was performed by CRISPR/Cas9 as described above (section F1). IRX3 and IRX5 gene expression was measured at day 0, 2, 4, 6 of differentiation (FIG. 4A). Sample preparation of primary human adipose cells, cDNA preparation, and qPCR analysis were carried out as described herein above (section B2).

4. Establishing Causality for Cellular Phenotypes of Mitochondrial Function and Thermogenesis To confirm that the C-to-T genome editing in primary human adipose progenitor cells from a homozygous risk allele carrier reverses obesity cellular signatures, gene expression analyses of mitochondrial function and thermogenic marker genes were performed, and oxygen consumption rate was measured as a surrogate for thermogenic activity of cells (mechanistic model in FIG. 4D).

Figures 11A, 11B, 11C:
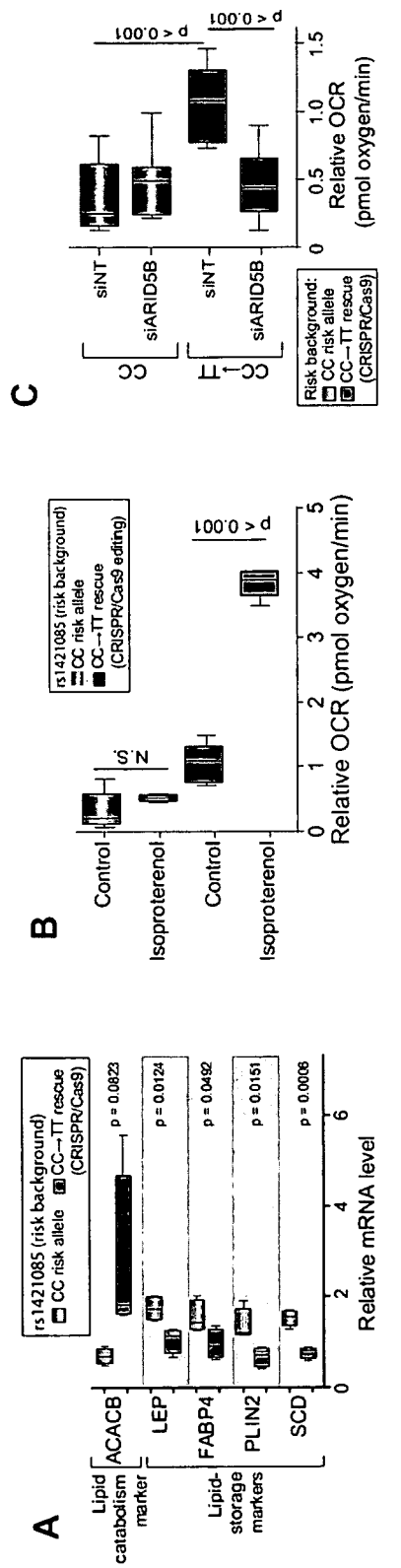
FIGS. 11A-11C. Phenotypic effects of rs1421085 circuitry on oxygen consumption and glycerol release.
Figure 12:
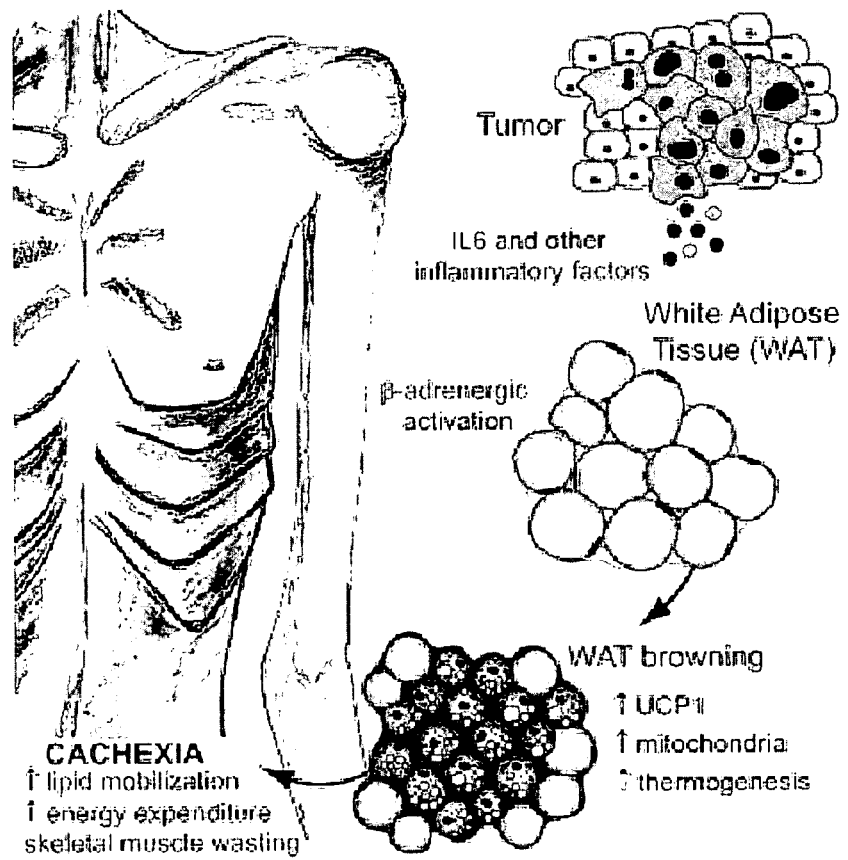
FIG. 12. A diagramatic representation of how the FTO variant affects cancer-associated cachexia.

Gene Expression Analyses of Mitochondrial Function, Thermogenic Marker Genes and Lipid Metabolism Regulators in CRISPR/Cas9 Edited Cells from a Risk Allele Carrier Gene expression analyses were performed using qPCR in 5 clonal expansions from CRISPR/Cas9 edited cells (FIG. 4B, FIG. 11A). Genome editing was performed as described herein above (section F1). Sample preparation of primary human adipose cells, cDNA preparation, and qPCR analysis were carried out as described herein above (section B2).

Oxygen Consumption Rate Measurements in CRISPR/Cas9 Edited Cells from a Risk Allele Carrier Basal and stimulated OCR measurements were performed in 5 clonal expansions from CRISPR/Cas9 edited cells. For OCR, cells were treated with isoproterenol (1 µmol/l) or DMSO (basal) for 4 hours. Total OCR was measured using the Seahorse XF24 (Seahorse Bioscience) and subtracted the minimum OCR level after rotenone/antimycin A treatment (5 µM) from the initial level without treatment (FIG. 11B). Furthermore, to more directly assess effects on mitochondrial thermogenesis, uncoupled respiration (proton leak) was calculated by subtracting the minimum OCR level after rotenone/antimycin from the minimum level after oligomycin treatment (5 µM) (FIG. 4C). OCR is described in more detail in section C3 above. The protocol was run with 3 min mixing and 2 min measuring. CRISPR/Cas9 genome editing was performed as described herein above (section F1).

Conditional Oxygen Consumption Rate Analyses in CRISPR/Cas9 Edited Primary Human Adipocytes To establish repressor causality, ARID5B knock-down was carried out in the CRISPR/Cas9 edited patient cells, and regulation of basal and stimulated oxygen consumption rate was assessed conditional on the presence of ARID5B by qPCR (FIG. 11C). C-to-T editing was performed by CRISPR/Cas9 as described herein above (section F1). siRNA-mediated ARID5B knock-down was performed with ON-TARGET-plus SMARTpool siRNA (Dharmacon) and HiPerFect (Qiagen). Sequences of ARID5B siRNA are disclosed herein. For the study, ARID5B siRNA SEQ ID NOs: 37, 40, and 41 were used in a mixture. Sample preparation of primary human adipose cells, cDNA preparation, and qPCR analysis were carried out as described above (section B2).

H. FTO Variant Effect on Cancer-Associated Cachexia

Subjects and Primary Tissues and Cell Culture

Human adipose tissues were obtained with informed, written consent from each subject, and approval by the local ethics committee of the Faculty of Medicine of the Technical University of Munich, Germany. Cancer patients were considered as being cachectic if they lost 10% or more weight within 3 months. If this criterion was not met, they were considered as non-cachectic. Both whole adipose tissue and isolated primary human adipose-derived progenitor cells from cachexia patients and controls were used for qPCR analyses.

Primary human adipose-derived progenitor cell preparation was obtained from adipose tissue of subjects. Adipose cells were isolated from whole adipose tissue as previously described (Svensson et al., Obesity (Silver Spring) 2014) with some modifications. Briefly, after expansion and freezing, the cells were cultured in DMEM/F12 (1:1) medium (supplemented with 10% FCS and 1% penicillin/streptomycin) for 18 h, followed by expansion in DMEM/F12 medium (supplemented with 2.5% FCS, 1% penicillin/streptomycin), 33 µM biotin, 17 µM pantothenic acid, 132 nM insulin, 10 ng/ml EGF, and lng/ml FGF until confluence. Adipogenic differentiation was then induced by supplementing with 66 nM insulin, 100 nM cortisol, 10 µg/ml transferrin, 1 nM triiodo-L-thyronin (T3), 2 µM rosiglitazone, 25 nM dexamethasone and 0.5 mM IBMX.

CRISPR/Cas9 Genome Editing

Plasmids: hCas9 and the gRNA cloning vector were purchased from Addgene (Plasmid ID #41815 and #41824, respectively). Genomic DNA was amplified from one rs1421085 CC risk allele carrier and one TT non-risk allele carrier. Site-directed Mutagenesis was performed using the Q5® Site-Directed Mutagenesis Kit (New England Biolabs) using the mutagenesis primer 5'-TAAGGCATGACATT-GATTAAGTGTC-3' (SEQ ID NO: 34). The guide RNAs (gRNAs) were designed using the CRISPR design online tool from the Zhang lab (crispr_mit_edu). 2 guide RNAs were used: 5' CACCGCTGGAAGGAACGCGTTTGTT-3' (SEQ ID NO: 27), 5'-CACCGGGACAGTGCGTA-GACTAAAC-3' (SEQ ID NO: 28). For transfection, GFP and Cas9 were cotransfected with sgRNAs, the homology vector, and pMACS plasmid 4.1 (Miltenyi Biotec, Cambridge, Mass.) in human adipose progenitor cells using the AMAXA® NUCLEOFECTOR® device (program U-033) (Lonza Group Ltd., Portsmouth, N.H.). Cells were sorted using the MACSelect™ Transfected Cell Selection cell sorting kit (Miltenyi Biotec, Cambridge, Mass.). Sorted cells were cultured for 3-5 days and clones propagated from single cell were picked out. Nucleotide exchange was confirmed by DNA sequencing.

RNA Preparation and qPCR

Total RNA was extracted with TRIZOL® (Invitrogen) for cell cultures or RNEASY® Lipid Tissue Kit (Qiagen) for whole tissue samples. cDNA was synthesized with High-Capacity cDNA Reverse Transcription Kit (Applied Biosystems). qPCR was performed using SYBR™ Green with 60° C. annealing temperature. Relative gene expression was calculated by the delta delta Ct method. Target gene expression was normalized to expression of HPRT or TBP (human).

For stimulation experiments, cells were stimulated with physiological concentrations of IL-6 (200 pg/ml) or PTHrP (100 ng/ml) for 48 hours before mRNA was harvested.

Oxygen Consumption Rate

Oxygen consumption rate (OCR) was measured using a Seahorse XF24 (Seahorse Bioscience). CRISPR/Cas9 edited cells were seeded at 70% confluence and induced to differentiate ($6 \times 10^4$ cells/well) the next day. On day 2 of differentiation, the medium was exchanged by XF Assay Medium (1 g/L glucose, 2 mM L-glutamine, 2 mM Na pyruvate) and 2% fatty acid-free BSA before 2 h incubation at 37° C. without $CO_2$. For stimulation experiments cells were either treated with physiological concentrations of IL-6 (200 pg/ml) or PTHrP (100 ng/ml) for 48 hours or with DMSO as a control. Cells were treated with isoproterenol (1 µmol/l) or DMSO (control) for the last 4 hours. Total oxygen consumption rate (OCR) was measured by a Seahorse XF24, measured by subtracting the minimum OCR level after rotenone/antimycin A treatment (5 µM) from the initial level without treatment. Uncoupled respiration (proton leak) was calculated by subtracting the minimum OCR level after rotenone/antimycin from the minimum level after oligomycin treatment (5 The analysis was run with 3 min mixing and 2 min measuring.

Accession Codes

Microarray data have been deposited in ArrayExpress (www.ebi.ac.uk/arrayexpress/) or GEO (www.ncbi.nlm.nih.gov/GEO). The data for abdominal subcutaneous adipose tissue (13 lean and 17 obese) is available with ArrayExpress accession E-TABM-862. The perirenal adipose tissue dataset (10 lean persons) is available with GEO accession (GSE59325).

Results

A. FTO Locus Effect on IRX3 and IRX5 in Human Adipocyte Progenitor Cells

To identify the cell types where the causal variant may act, chromatin state maps (Kundaje et al., Nature 518:317-30, 2015; Ernst et al., Nat. Biotechnol 2015) the FTO obesity region across 127 cell types were examined. An unusually-long enhancer (12.8 kb) in mesenchymal adipocyte progenitors indicated a major regulatory locus (FIG. 1B and FIG. 5C). Haplotype-specific enhancer assays showed 2.4-fold higher activity for the risk haplotype in human SGBS adipocytes (derived from a patient with Simpson-Golabi-Behmel syndrome—SGBS), indicating genetic control (FIG. 1C). Enhancers in brain and other cell types were remarkably shorter and lacked allelic activity (FIGS. 5C and 5D).

Figure 1D:
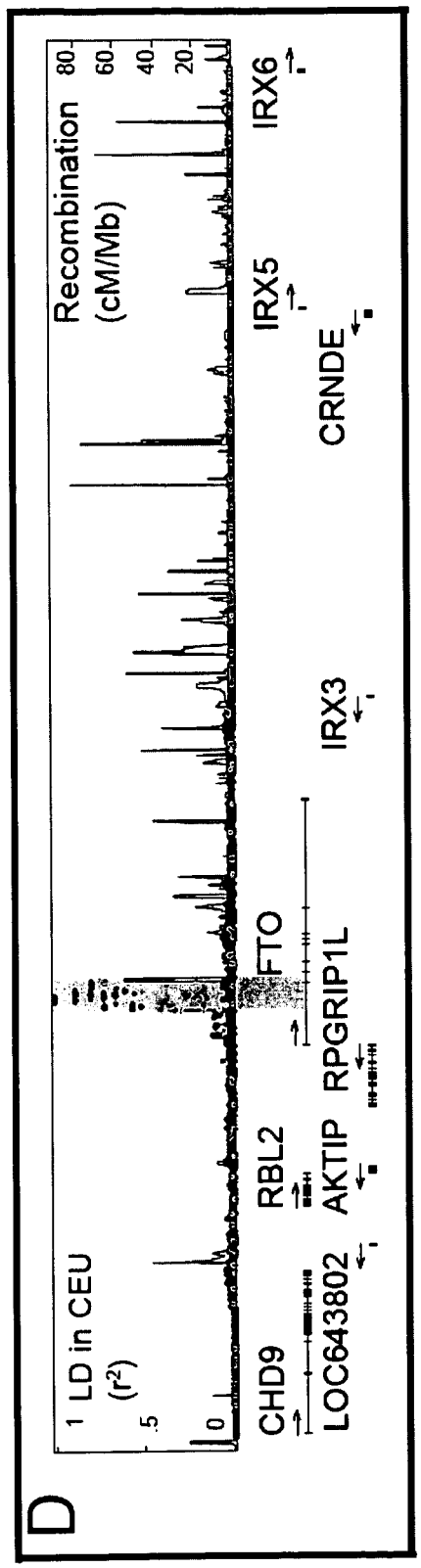
Figures 1E, 1F:
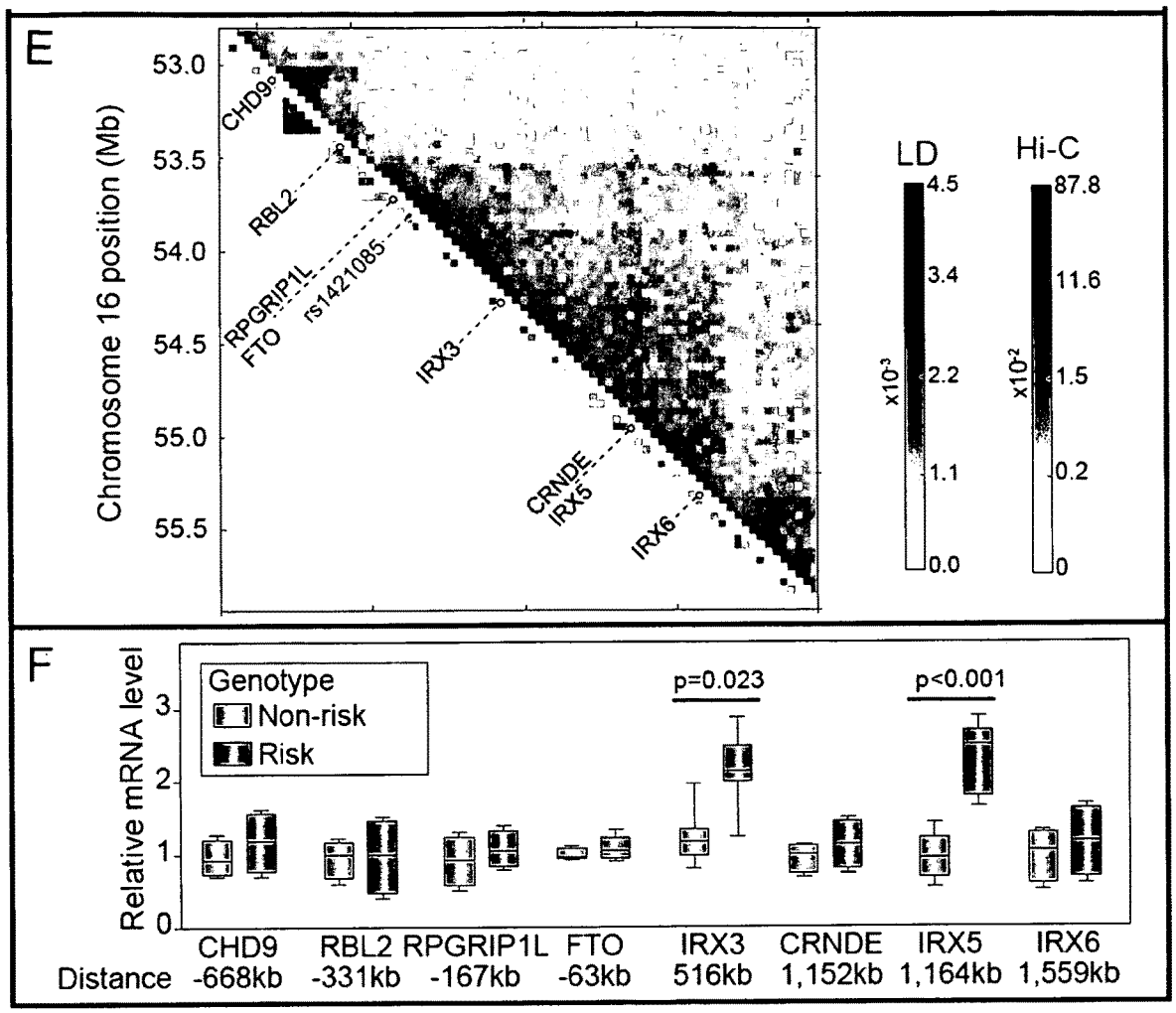

To predict putative target genes, large domains showing long-range three-dimensional chromatin interactions surrounding FTO were examined, resulting in eight candidates (FIG. 1D-E). Among them, developmental regulators IRX3 and IRX5 showed genotype-associated expression, indicating long-range (1.2 Mb) genetic control in primary preadipocytes (FIG. 1F). Genotype-associated expression was not observed in whole-adipose tissue, consistent with previous reports (Grunnet et al., Diabetes 58:2402-08, 2009; Kloting et al., Diabetologia 51:641-47, 2008) indicating the effect is cell-type specific, as preadipocytes represent a minority of cells in adipose tissue (FIG. 6A).

B. FTO Locus Effect on Mitochondrial Thermogenesis and Lipid Storage

To recognize putative targets of IRX3 and IRX5 in adipocytes, positively and negative-correlated genes were examined using genome-wide expression patterns in a separate cohort of 10 non-genotyped patients. Mitochondrial functions were negatively correlated and FXR/RXR lipid metabolism pathways were positively correlated, suggesting roles in energy dissipation and storage (FIG. 2A and Table 2). Consistently, IRX3 and IRX5 showed lower average expression in human white adipose tissue in 9 participants, and negative correlation with PGC1A and UCP1 using inter-individual expression patterns in perithyroid brown adipose tissue (preformed BAT) (FIGS. 6B and 6C), indicating potential roles in repression of thermogenesis.

To examine trans-eQTL genetic control of energy balance by the FTO obesity locus, primary preadipocyte expression was evaluated in risk and non-risk participants for the most correlated genes with mitochondrial and FXR/RXR functions, and for several known markers of energy balance regulation (FIGS. 6D and 6E). Risk participants showed lower expression for mitochondrial, browning and respiration genes, and higher expression for lipid storage markers, indicating a shift from energy dissipation to storage.

These expression differences were also reflected in the cellular signatures of obesity. Risk allele carriers showed increased adipocyte size, reduced mitochondrial DNA content, and loss of UCP1 response to β-adrenergic stimulus or cold exposure (FIGS. 2B and 2C, FIG. 6F), and also decreased basal oxygen consumption rate and resistance to isoproterenol-mediated uncoupling (FIG. 6G), indicating excessive triglyceride accumulation, and reduced mitochondrial oxidative capacity, white adipocyte browning, and thermogenesis.

C. Adipocyte-Autonomous Effects of IRX3 and IRX5 on Energy Balance

Figures 7A, 7B, 7C:
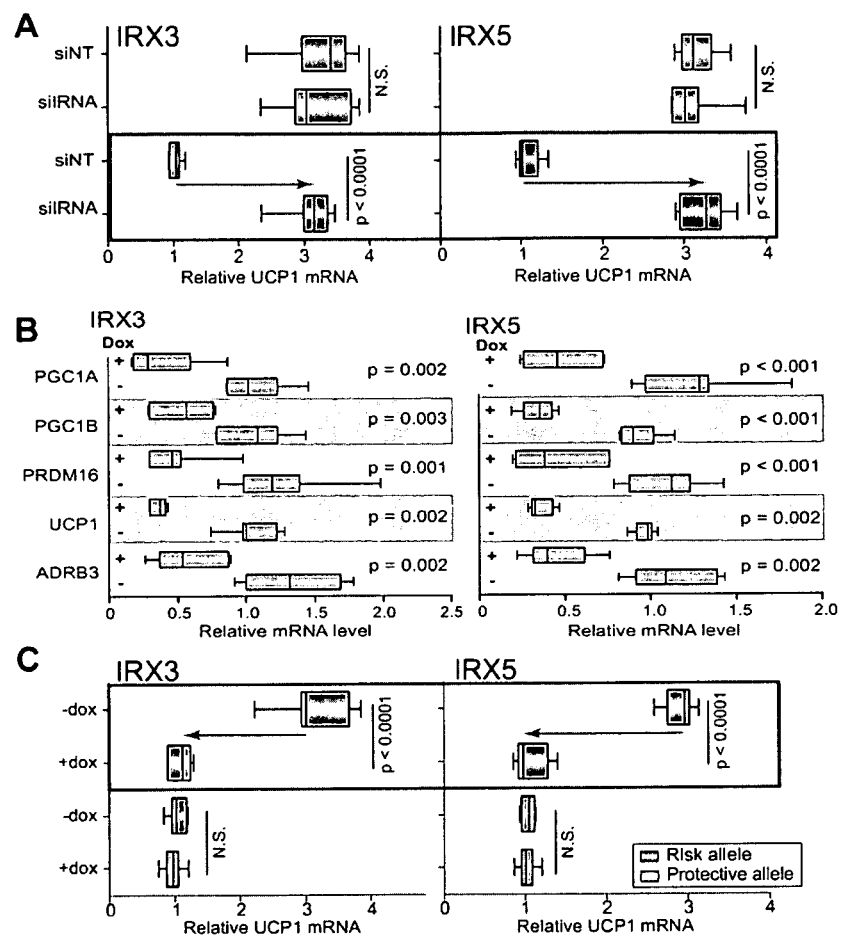
FIGS. 7A-7C. Regulatory roles of IRX3 and IRX5 in adipocyte mitochondrial thermogenesis in humans.

The effect of manipulating IRX3 and IRX5 expression on thermogenesis in primary preadipocytes isolated from both risk and non-risk participants was quantified. For participants at risk, IRX3 and IRX5 knock-down restored oxygen consumption and thermogenesis response to non-risk levels (FIG. 2D) and restored UCP1 expression levels (FIG. 7A). For non-risk participants, IRX3 and IRX5 overexpression reduced basal respiration and thermogenesis to risk-allele levels (FIG. 2D), and decreased expression of UCP1, other regulators of mitochondrial function and thermogenesis (PGC1A, PGC1B, PRDM16), and the 3-adrenergic receptor (ADRB3), which also regulates UCP1-independent thermogenesis programs (FIGS. 7B and 7C). These manipulations had no significant effect on the reciprocal genotypes, indicating that IRX3 and IRX5 levels recapitulate the impact of the FTO genetic variant on thermogenesis.

To examine the effects of adipose repression of Irx3 at the organism level, adipose dominant-negative Irx3 mice (aP2-Irx3DN) were used. These showed strong anti-obesity characteristics, including reduced body size, body weight, fat-mass, white and brown fat depots and adipocyte size (FIG. 3B and FIG. 8A-8G). These adipose dominant-negative Irx3 mice also showed resistance to weight gain on a high-fat diet, increased energy expenditure both at night and during the day, and increased oxygen consumption at both room temperature (22° C.) and thermoneutrality (30° C.), but lacked significant differences in food intake or locomotor activity (FIG. 3C; FIGS. 8H and 8I). At both the molecular and cellular levels, these mice showed increased mitochondrial activity and thermogenesis marker expression, reduced lipid storage marker expression in both white and brown fat compartments, and markedly smaller adipocytes (FIG. 8M-8O).

Next, tissue-autonomous vs. brain-mediated roles were evaluated by comparing the adipose dominant negative aP2-Irx3DN mice with hypothalamus dominant-negative Ins2-Irx3DN mice (Smemo et al., Nature 507:371-75, 2014). The aP2-Irx3DN mice showed a 3-fold stronger reduction in fat-mass-ratio (57% vs. 19%), despite 3-fold lower transgene expression in hypothalamus (FIG. 8N), indicating a hypothalamus-independent regulatory role of Irx3 on whole-body energy regulation. The phenotypic effects for aP2-Irx3DN mice were also stronger than for whole-body Irx3 knock-out mice, suggesting potential dominant repressor effects in adipocytes or other tissues, and were independent of Fto gene expression, which showed no change (FIGS. 8P and 8Q). Consistent with cell-autonomous roles, manipulation of Irx3 and Irx5 also led to energy balance differences in three mouse cellular models, including MEF-derived adipocytes, white 3T3-L1 preadipocytes, and β-adrenergic stimulated beige ME3 preadipocytes (FIG. 9). In each case, our results indicate that Irx3 and Irx5 induce adipocyte lipid accumulation and repress thermogenesis in a cell-autonomous way.

D. Causal Variant Disrupts Repressions by ARID5B

To predict the causal variant whose disruption is necessary and sufficient to cause IRX3 and IRX5 dysregulation in human preadipocytes, phylogenetic module conservation analysis (PMCA) (Claussnitzer et al., Cell 156:343-58, 2014) was used (FIG. 3A-B; FIGS. 10A and 10B). The highest PMCA score was found for the rs1421085 T-to-C single-nucleotide variant (SNV), which is in perfect linkage disequilibrium with both the reported top SNV rs1558902 across multiple populations (1000 Genomes Phase 1 data), consistent with a potential causal role.

To evaluate rs1421085 causality for enhancer activity, the C allele was introduced to the non-risk haplotype in the luciferase reporter assay. The T-to-C single-nucleotide alteration increased enhancer activity levels for 10 kb and 1 kb segments, in both orientations, and both upstream and downstream of transcription start, indicating gain of enhancer activity for the rs1421085 risk allele (FIGS. 10C and 10D).

To evaluate the variant effect on regulator binding, electrophoretic mobility shift assays of adipocyte nuclear extract were performed using probes for the risk and protective allele of rs1421085. Binding was observed for the protective allele T, which lacked enhancer activity, but no binding was observed for the risk allele C, indicating that the increased enhancer activity in the risk allele is likely due to loss of repressor binding rather than gain of activator binding (FIG. 10E).

To recognize potential upstream regulators, disrupted motifs and regulator expression were examined. The T-to-C substitution disrupts conserved motifs for the NKX6-2, LHX6, and ARID family of regulators (FIG. 3A). Among them, ARID5B showed the highest adipose tissue and adipocyte gene expression, competed away the EMSA shifted DNA-regulator complex, is known to play both repressive and activating roles, and was previously implicated in adipogenesis and lipid metabolism in mice (Yamakawa et al., Biochem. Biophys. Res. Comm. 391:277-81, 2010; Whitson et al., Biochem. Biophys. Res. Comm. 258:326-31, 1999) (FIG. 10E-F). Across non-risk participants, ARID5B was negatively correlated with IRX3 and IRX5 expression levels, consistent with a repressive role. No correlation was found in risk participants, indicating loss of ARID5B regulation (FIG. 10G).

To evaluate ARID5B causality, the consequences of its knockdown and overexpression on IRX3 and IRX5 were examined. ARID5B knockdown increased IRX3 and IRX5 expression in primary preadipocytes from non-risk participants to risk-participant levels, indicating loss of repression, but had no effect on risk participants, indicating epistasis with the obesity risk haplotype (FIG. 10H). Consistently, ARID5B knockdown in SGBS enhancer assays increased activity of the non-risk allele to risk-allele levels, indicating loss of repression, but had no effect on risk-allele constructs, indicating epistasis with the rs1421085 risk allele (FIG. 10I). ARID5B overexpression further reduced IRX3 and IRX5 levels in non-risk participants, indicating strengthened repression, but had no significant effect on risk participants, consistent with impaired ARID5B repression in the risk haplotype (FIG. 10J).

The cellular effects of ARID5B-directed perturbations in primary preadipocytes from risk and non-risk participants were examined. For non-risk participants, ARID5B knockdown reduced basal oxygen consumption and lipolysis (FIGS. 10K and 10L), and shifted expression patterns from mitochondrial to lipid markers (FIG. 6E), indicating ARID5B plays causal roles in energy balance regulation. In contrast, ARID5B knock-down had no effect on risk participants, consistent with loss of ARID5B control.

These results indicate that the FTO obesity variant acts by disruption of ARID5B binding in the risk haplotype, leading to loss of repression, gain of enhancer activity, and increased IRX3 and IRX5 expression (FIG. 10M).

E. C-to-T Editing of Risk Variant Reverses Obesity Signatures

Targeted genome editing technology with CRISPR/Cas926 enables test the phenotypic effect of altering the predicted causal nucleotide rs1421085 in its endogenous genomic context, in isolation of the other obesity-associated genetic variants in the same haplotype. CRISPR/Cas9 was used in primary preadipocytes with two separate guide RNAs, one for rs1421085 C-to-T rescue of the ARID5B motif disruption in risk participants, and one for rs1421085 T-to-C disruption of the ARID5B motif in non-risk participants.

First, the effect of rs1421085 editing on IRX3 and IRX5 expression levels was evaluated. Starting from preadipocytes of a non-risk participant, T-to-C editing increased endogenous IRX3 and IRX5 expression 2-fold to levels seen in risk participants, and starting from the edited preadipocytes, C-to-T re-editing back to the non-risk allele returned to low expression levels (FIG. 3C). Starting from the risk haplotype, C-to-T editing reduced IRX3 and IRX5 to non-risk-allele levels, but only in presence of ARID5B (FIG. 3D), establishing disruption of ARID5B repression by rs1421085 as the mechanistic basis of the IRX3 and IRX5 dysregulatory event that mediates the FTO locus effects on obesity.

Next, the role of rs1421085 editing during white vs. beige differentiation was examined by studying expression differences between edited and unedited preadipocytes during differentiation. Unedited adipocytes from the at-risk participant showed a peak in IRX3 and IRX5 expression in days 1-4 of preadipocytes differentiation, which was abolished by rs1421085 editing, indicating a causal role in developmental gene expression programs (FIG. 4A). This was reflected in a significant increase in expression of thermogenesis regulators (ADRB3, DIO2, PGC1A, UCP1) and mitochondrial markers (NDUFA10, COX7A, CPT1) in differentiating preadipocytes (FIG. 4B), indicating that C-to-T editing of the risk allele rescued thermogenesis regulatory programs.

Lastly, the role of rs1421085 editing in cellular signatures of obesity was evaluated by quantifying phenotypic differences between edited and unedited adipocytes. Indicating a causal role on energy balance regulation, C-to-T rescue of rs1421085 in edited adipocytes resulted in reduced gene expression for lipid storage and lipolytic markers (FIG. 6E, 11A) and 4-fold increased basal metabolic rate, β-adrenergic oxygen consumption, and thermogenesis (FIG. 4C and FIG. 11B). In particular, rescue of the ARID5B motif in C-to-T edited preadipocytes restored the strong dependence of mitochondrial respiration on ARID5B seen in non-risk participants (FIG. 11C).

F. FTO Variant Affects Cancer-Associated Cachexia

Figure 13:
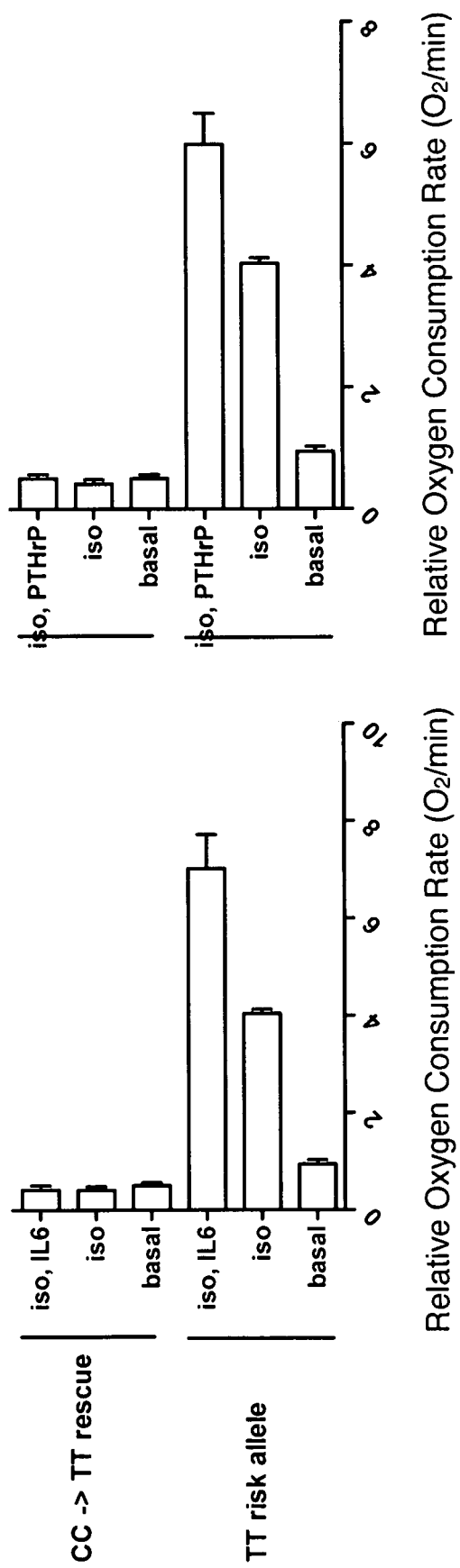
FIG. 13. CRISPR/Cas9 editing of rs1421085 in potential TT cachexia risk allele carriers rescues IL6 and PTHrP-induced browning in human adipocytes.
Figure 14:
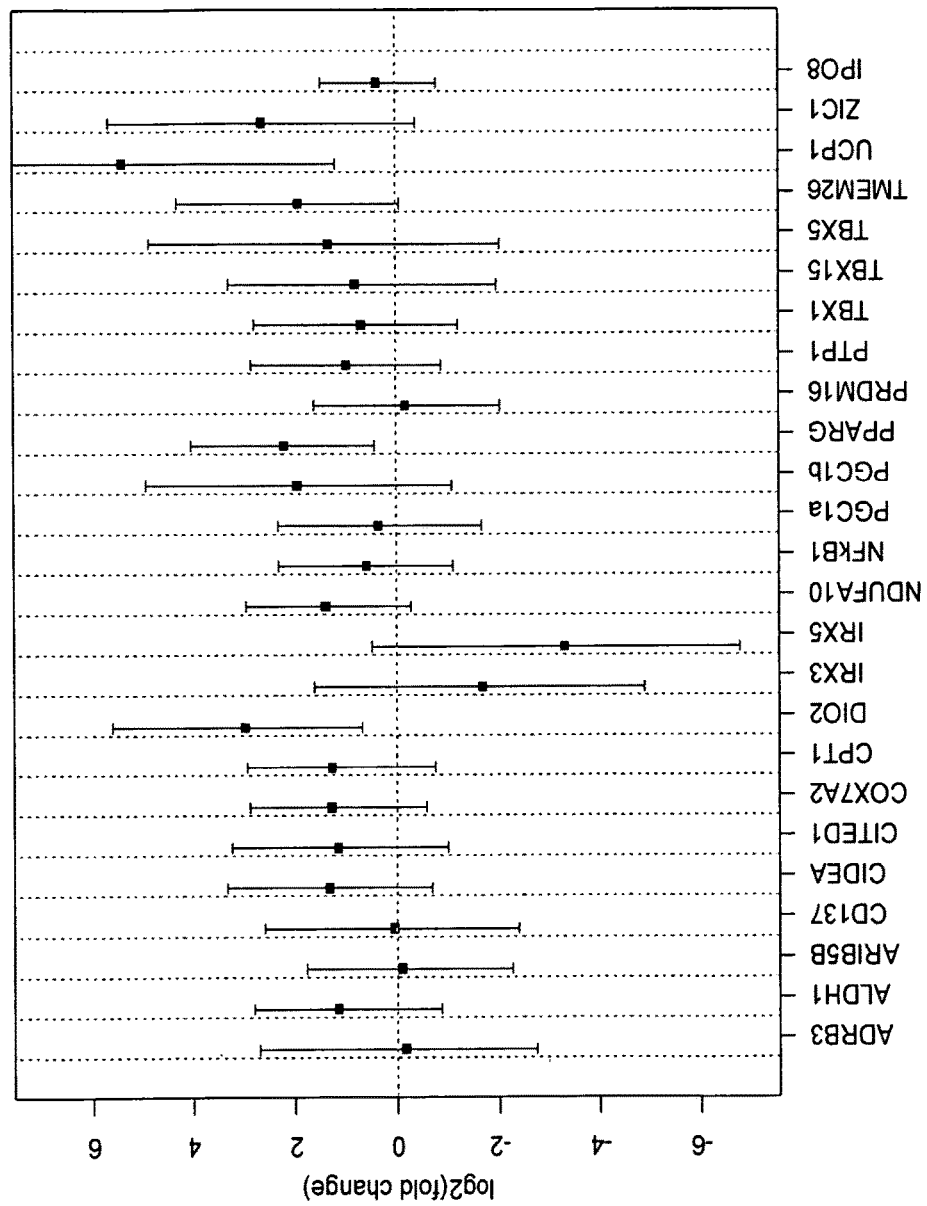
FIG. 14. Expression regulation of marker genes for cachexia, showing 64 samples of subcutaneous tissue from patients with and without cachexia. The figure depicts the effect on expression due to genotype CT (46 samples) and CC (18 samples), as well as cancer-associated cachexia (CAC)-status.

The obesity protective TT allele of rs1421085 was examined to determine its potential role for increased risk of cancer-associated cachexia by increased browning of adipocytes in humans. CRISPR/Cas9 studies herein show that editing of rs1421085 in potential TT cachexia risk allele carriers rescues IL6 and PTHrP-induced Browning in human adipocyte. As shown in FIG. 13, TT cachexia risk allele cells significantly respond to IL-6 and PTHrP stimuli, and that the T-to-C CRISPR/Cas9-mediated editing of patient samples (CC→TT rescue) rescues the phenotype of excessive mitochondrial thermogenesis rate. In contrast, the inflammatory cytokine TNF-α did not have an effect on adipocyte browning markers and energy dissipation, suggesting IL-6 and PTHrP as being specific for thermogenesis.

Further, a generalized linear mixed model (LMM) was generated to determine how IRX3 and IRX5, which are mitochondrial and beiging markers, are regulated in response to genotype and cancer-associated cachexia (CAC)—status and the compound effect of both—in subcutaneous adipose tissue. Of interest in this analysis were the effects on expression of IRX3 and IRX5 as a function of risk variant (TT) versus non-risk variant (CC) of the rs1421085 SNP, cachexia vs non-cachexia, as well as of the compound effect of cachexia and the risk-variant (TT) versus the compound effect of non-cachexia and the non-risk variant (CC). Before generating the LMM, a quality check of the data with the HTqPCR and NormqPCR packages were made. Next, 66 filtered and normalized samples with known genotype and Cancer-associated Cachexia (CAC)—status to perform a LMM making the analysis more powerful—were obtained. Thus, the MCMC.qPCR package was used. The model was fitted as follows: ln(rate)~gene+gene:genotype+gene:CAC+gene:CAC:genotype+sample+gene:residual. Of primary interest are the "fixed effects" genotype, CAC-status and the compound effect of cachexia and genotype. In the MCMC.qPCR package there are some further effects included, which take into consideration other important sources of variation that, while having negligible effect, were taken into account to ensure accuracy of the model. The most important of these "random effects" is the sample effect accounting for variation in quality and quantity among samples. Moreover, an error term gene:residual was added to account for the residual variation.

These results indicate that the rs1421085 T-to-C single-nucleotide alteration underlies the FTO obesity association, by disrupting ARID5B repression of IRX3 and IRX5, leading to a developmental shift from browning to whitening programs and loss of mitochondrial thermogenesis (FIG. 4D). In addition, the same mechanism underlies cancer-associated cachexia.

The results shown herein elucidates a mechanistic basis for the genetic association of FTO with obesity, indicating that the causal variant rs1421085 disrupts ARID5B repressor binding, de-represses IRX3 and IRX5 during early adipocyte differentiation, and leads to a cell-autonomous shift from white adipocyte browning and thermogenesis to lipid storage, increased fat stores, and body weight gain.

To translate GWAS results into mechanistic insights, public resources (epigenomic annotations, chromatin conformation, regulatory motif conservation), targeted experiments for risk and nonrisk haplotypes (enhancer tiling, gene expression, cellular profiling), and directed perturbations in human primary cells and mouse models (regulator/target knockdown and overexpression, CRISPR/Cas9 genome editing) were combined. These methods are specific to the elucidation of non-coding variants, which constitute the majority of GWAS signals, as 80% of GWAS loci lack protein-altering variants and 93% have non-coding top hits (Welter et al., Nucleic Acids Res. 42:D1001-6, 2014).

The FTO obesity association is unusual in many ways. First, rs1421085 shows both high frequency and strong effect size, (Loos and Yeo, Nat. Rev. Endocrin. 10:51-61, 2014) suggesting positive selection or bottlenecks (e.g. 44% frequency in European vs. 5% in African populations). Additionally, rs1421085 shows switch-like behavior in enhancer activity, target gene expression, and cellular phenotypes, possibly due to selective pressures on energy balance control for rapid adaptation. Also, rs1421085 acts specifically in early preadipocyte differentiation, emphasizing the importance of profiling diverse tissues, cell types, and developmental stages. Further, enhancer activity is found only for the risk allele, emphasizing the importance of profiling both alleles. In addition, rs1421085 leads to gain-of-function (increased enhancer, IRX3, and IRX5 activity), a property rare for protein-coding variants but possibly common for non-coding variants.

The apparent genetic link between obesity and cell-autonomous adipocyte browning suggests a central role of beige adipocyte thermogenesis in whole-body energy metabolism in human, consistent with recent reports for PRDM16 in mouse (Cohen et al., Cell 156:304-16, 2014). IRX3 and IRX5 show evolutionarily-conserved roles, indicating conserved adaptive thermogenesis circuits, and likely play both UCP1-dependent and UCP1-independent roles. Even though IRX3 and IRX5 dysregulation by rs1420185 was restricted to early differentiation, their effects persisted in mature adipocytes, and their targeting can have broader effects.

Additionally, it was observed that direct manipulation of the ARID5B-rs1421085-IRX3/IRX5 circuitry in primary adipocytes from patients reversed the signatures of obesity. In addition to changes in physical activity and nutrition, manipulation of mitochondrial thermogenesis (Lidell et al., J. Intern. Med. 2014) offers another pathway for shifting between energy storage and expenditure in a tissue-independent way in humans.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

SEQUENCES siRNA targeting IRX3

SEQ ID NO: 1
5'-CAG CUG GGA UAC CAA UAC AUU-3'
SEQ ID NO: 2
5'-UGC CUU GGA AGU GGA GAA AUU-3'
SEQ ID NO: 3
5'-GCU GGG AUA CCA AUA CAU CUU-3'
SEQ ID NO: 4
5'-GCC UUG GAA GUG GAG AAA AUU-3'
SEQ ID NO: 5
5'-AGC UGG GAU ACC AAU ACA UUU-3'
SEQ ID NO: 6
5'-GAG CAG AUC AAU AGG CGA AUU-3'
SEQ ID NO: 7
5'-GUA GAA AUG UCA AUC AGA GUU-3'
SEQ ID NO: 8
5'-CCG UAG AAA UGU CAA UCA GUU-3'
SEQ ID NO: 9
5'-AGU GAA AAC UAG AGG AGG GUU-3'
SEQ ID NO: 10
5'-GGA GUG AAA ACU AGA GGA GUU-3'
SEQ ID NO: 11
5'-CCC GUA GAA AUG UCA AUC AUU-3'
SEQ ID NO: 12
5'-UAG AAA UGU CAA UCA GAG CUU-3'
SEQ ID NO: 13
5'-GGG AGU GAA AAC UAG AGG AUU-3'
SEQ ID NO: 14
5'-AAA ACU AGA GGA GGG CGA AUU-3'
SEQ ID NO: 15
5'-GAA UCU CCG CCA AUC UGU UUU-3'
SEQ ID NO: 17
5'-GCC CCG UAG AAA UGU CAA UUU-3'
SEQ ID NO: 18
5'-AGA AAU GUC AAU CAG AGC CUU-3' siRNA targeting IRX5

SEQ ID NO: 19
5'-AAG CCC AAA CUG UGG UCU UUU-3'
SEQ ID NO: 20
5'-AGC CAA ACU GUG GUC UUU UUU-3'
SEQ ID NO: 21
5'-AAA CUG UGG UCU UUG GCA GUU-3'
SEQ ID NO: 22
5'-AAC UGU GGU CUU UGG CAG AUU-3'
SEQ ID NO: 23
5'-AAG CCC AAA CUG UGG UCU UUU-3'
SEQ ID NO: 24
5'-AGC CAA ACU GUG GUC UUU UUU-3'
SEQ ID NO: 25
5'-AAA CUG UGG UCU UUG GCA GUU-3'
SEQ ID NO: 26
5'-AAC UGU GGU CUU UGG CAG AUU-3' siRNA targeting ARID5B

SEQ ID NO: 35
5'-AGG AGA AGA AGA UAA GCC CUU-3'
SEQ ID NO: 36
5'-CUA UGU UUC AAG CUG CUC AUU-3'
SEQ ID NO: 37
5'-AAG GAG AAG AAG AUA AGC CUU-3'
SEQ ID NO: 38
5'-ACC UUU GGA CUA UGU UUC AUU-3'
SEQ ID NO: 39
5'-GAU UAC AUU GCC AAC UGC AUU-3'
SEQ ID NO: 40
5'-GGC ACU UUA UAA AUA CAU GUU-3'
SEQ ID NO: 41
5'-GAU UAA CCU UUG GAC UAU GUU-3'
SEQ ID NO: 42
5'-AUU AAC CUU UGG ACU AUG UUU-3'
SEQ ID NO: 43
5'-UAU GAA ACA AUA ACA GCC CUU-3'
SEQ ID NO: 44
5'-UAU GUU UCA AGC UGC UCA AUU-3'

CRISPR/Cas9 sgRNA targeting rs1421085

SEQ ID NO: 27
5' CACCGCTGGAAGGAACGCGTTTGTT-3'
SEQ ID NO: 28
5'-CACCGGGACAGTGCGTAGACTAAAC-3'

Primer set for EnR-Irx3 transgene

SEQ ID NO: 29
ROSA-FP: 5'-AAAGTCGCTCTGAGTTGTTAT-3'
SEQ ID NO: 30
ROSA-WT-RP: 5'-GGAGCGGGAGAAATGGATATG-3'
SEQ ID NO: 31
ROSA-MUT-RP: 5'-GCGAAGAGTTTGTCCTCAACC-3'

Primer set for Cre gene

SEQ ID NO: 32
forward: 5'-ATCCGAAAAGAAAACGTTGA-3'
SEQ ID NO: 33
reverse: 5'-ATCCAGGTTACGGATATAGT-3'

Primer for rs1421085 mutagenesis

SEQ ID NO: 34
5'-TAAGGCATGACATTGATTAAGTGTC-5'

REFERENCES

1. Adams K F, Schatzkin A, Harris T B, et al. Overweight, obesity, and mortality in a large prospective cohort of persons 50 to 71 years old. N Engl J Med 2006; 355:763-78.
2. Virtanen K A, Lidell M E, Orava J, et al. Functional brown adipose tissue in healthy adults. N Engl J Med 2009; 360:1518-25.
3. van Marken Lichtenbelt W D, Vanhommerig J W, Smulders N M, et al. Cold-activated brown adipose tissue in healthy men. N Engl J Med 2009; 360:1500-8.
4. Wu J, Bostrom P, Sparks L M, et al. Beige adipocytes are a distinct type of thermogenic fat cell in mouse and human. Cell 2012; 150:366-76.
5. Cypess A M, Lehman S, Williams G, et al. Identification and importance of brown adipose tissue in adult humans. N Engl J Med 2009; 360:1509-17.
6. Shabalina I G, Petrovic N, de Jong J M, Kalinovich A V, Cannon B, Nedergaard J. UCP1 inbrite/beige adipose tissue mitochondria is functionally thermogenic. Cell Rep 2013; 5:1196-203.

7. Kong X, Banks A, Liu T, et al. IRF4 Is a Key Thermogenic Transcriptional Partner of PGC-lalpha. Cell 2014; 158:69-83.
8. Seale P, Conroe H M, Estall J, et al. Prdm16 determines the thermogenic program of subcutaneous white adipose tissue in mice. J Clin Invest 2011; 121:96-105.
9. Cohen P, Levy J D, Zhang Y, et al. Ablation of PRDM16 and beige adipose causes metabolic dysfunction and a subcutaneous to visceral fat switch. Cell 2014; 156:304-16.
10. Speliotes E K, Willer C J, Berndt S I, et al. Association analyses of 249,796 individuals reveal 18 new loci associated with body mass index. Nat Genet 2010; 42:937-48.
11. Locke A E, Kahali B, Berndt S I, et al. Genetic studies of body mass index yield new insights for obesity biology. Nature 2015; 518:197-206.
12. Frayling™, Timpson N J, Weedon M N, et al. A common variant in the FTO gene is associated with body mass index and predisposes to childhood and adult obesity. Science 2007; 316:889-94.
13. Dina C, Meyre D, Gallina S, et al. Variation in FTO contributes to childhood obesity and severe adult obesity. Nat Genet 2007; 39:724-6.
14. Fischer J, Koch L, Emmerling C, et al. Inactivation of the Fto gene protects from obesity. Nature 2009; 458:894-8.
15. Stratigopoulos G, Martin Carli J F, O'Day D R, et al. Hypomorphism for RPGRIP1L, a ciliary gene vicinal to the FTO locus, causes increased adiposity in mice. Cell Metab 2014; 19:767-79.
16. Smemo S, Tena J J, Kim K H, et al. Obesity-associated variants within FTO form long-range functional connections with IRX3. Nature 2014; 507:371-5.
17. Ragvin A, Moro E, Fredman D, et al. Long-range gene regulation links genomic type 2 diabetes and obesity risk regions to HHEX, SOX4, and IRX3. Proc Natl Acad Sci USA 2010; 107:775-80.
18. Jowett J B, Curran J E, Johnson M P, et al. Genetic variation at the FTO locus influences RBL2 gene expression. Diabetes 2010; 59:726-32.
19. Roadmap_Epigenomics_Consortium, Kundaje A, Meuleman W, et al. Integrative analysis of 111 reference human epigenomes. Nature 2015; 518:317-30.
20. Ernst J, Kellis M. Large-scale imputation of epigenomic datasets for systematic annotation of diverse human tissues. Nat Biotechnol 2015.
21. Grunnet L G, Nilsson E, Ling C, et al. Regulation and function of FTO mRNA expression in human skeletal muscle and subcutaneous adipose tissue. Diabetes 2009; 58:2402-8.
22. Kloting N, Schleinitz D, Ruschke K, et al. Inverse relationship between obesity and FTO gene expression in visceral adipose tissue in humans. Diabetologia 2008; 51:641-7.
23. Claussnitzer M, Dankel S N, Klocke B, et al. Leveraging cross-species transcription factor binding site patterns: from diabetes risk loci to disease mechanisms. Cell 2014; 156:343-58.
24. Yamakawa T, Sugimoto K, Whitson R H, Itakura K. Modulator recognition factor-2 regulates triglyceride metabolism in adipocytes. Biochem Biophys Res Commun 2010; 391:277-81.
25. Whitson R H, Huang T, Itakura K. The novel Mrf-2 DNA-binding domain recognizes a fivebase core sequence through major and minor-groove contacts. Biochem Biophys ResCommun 1999; 258:326-31.
26. Ran F A, Hsu P D, Wright J, Agarwala V, Scott D A, Zhang F. Genome engineering using the CRISPR-Cas9 system. Nature protocols 2013; 8:2281-308.
27. Welter D, MacArthur J, Morales J, et al. The NHGRI GWAS Catalog, a curated resource of SNP-trait associations. Nucleic Acids Res 2014; 42:D1001-6.
28. Loos R J, Yeo G S. The bigger picture of FTO—the first GWAS-identified obesity gene. Nat Rev Endocrinol 2014; 10:51-61.
29. Lidell M E, Betz M J, Enerback S. Brown adipose tissue and its therapeutic potential. J Intern Med 2014.
30. Loos R J, Lindgren C M, Li S, et al. Common variants near MC4R are associated with fat mass, weight and risk of obesity. Nat Genet 2008; 40:768-75.
31. Dixon J R, Selvaraj S, Yue F, et al. Topological domains in mammalian genomes identified by analysis of chromatin interactions. Nature 2012; 485:376-80.
32. Roadmap_Epigenomics_Consortium, Kundaje A, Meuleman W, et al. Integrative analysis of 111 reference human epigenomes. Nature 2015; 518:317-30.
33. ENCODE_Consortium. An integrated encyclopedia of DNA elements in the human genome. Nature 2012; 489: 57-74.
34. Zhou X, Maricque B, Xie M, et al. The Human Epigenome Browser at Washington University. Nat Methods 2011; 8:989-90.
35. Ernst J, Kellis M. ChromHMM: automating chromatin-state discovery and characterization. Nat Methods 2012; 9:215-6.
36. Ernst J, Kellis M. Large-scale imputation of epigenomic datasets for systematic annotation of diverse human tissues. Nat Biotechnol 2015.
37. Fischer-Posovszky P, Newell F S, Wabitsch M, Tornqvist H E. Human SGBS cells—a unique tool for studies of human fat cell biology. Obes Facts 2008; 1:184-9.
38. Lieberman-Aiden E, van Berkum N L, Williams L, et al. Comprehensive mapping of longrange interactions reveals folding principles of the human genome. Science 2009; 326:289-93.
39. Imakaev M, Fudenberg G, McCord R P, et al. Iterative correction of Hi-C data reveals hallmarks of chromosome organization. Nat Methods 2012; 9:999-1003.
40. Veum V L, Dankel S N, Gjerde J, et al. The nuclear receptors NUR77, NURR1 and NOR1 in obesity and during fat loss. Int J Obes (Lond) 2012; 36:1195-202.
41. de Kok J B, Roelofs R W, Giesendorf B A, et al. Normalization of gene expression measurements in tumor tissues: comparison of 13 endogenous control genes. Lab Invest 2005; 85:154-9.
42. Svensson P A, Lindberg K, Hoffmann J M, et al. Characterization of brown adipose tissue in the human perirenal depot. Obesity (Silver Spring) 2014.
43. Ye L, Wu J, Cohen P, et al. Fat cells directly sense temperature to activate thermogenesis. Proc Natl Acad Sci USA 2013; 110:12480-5.
44. Shan T, Liu W, Kuang S. Fatty acid binding protein 4 expression marks a population of adipocyte progenitors in white and brown adipose tissues. FASEB J 2013; 27:277-87.
45. Li D, Sakuma R, Vakili N A, et al. Formation of proximal and anterior limb skeleton requires early function of Irx3 and Irx5 and is negatively regulated by Shh signaling. Dev Cell 2014; 29:233-40.
46. Li Z J, Nieuwenhuis E, Nien W, et al. Kif7 regulates Gli2 through Sufu-dependent and -independent functions during skin development and tumorigenesis. Development 2012; 139:4152-61.

47. Woltjen K, Michael I P, Mohseni P, et al. piggyBac transposition reprograms fibroblasts to induced pluripotent stem cells. Nature 2009; 458:766-70.
48. Lukas J, Bartkova J, Rohde M, Strauss M, Bartek J. Cyclin D1 is dispensable for G1 control in retinoblastoma gene-deficient cells independently of cdk4 activity. Mol Cell Biol 1995; 15:2600-11.
49. Hansen J B, Jorgensen C, Petersen R K, et al. Retinoblastoma protein functions as a molecular switch determining white versus brown adipocyte differentiation. Proc Natl Acad Sci USA 2004; 101:4112-7.
50. Cartharius K, Frech K, Grote K, et al. MatInspector and beyond: promoter analysis based on transcription factor binding sites. Bioinformatics 2005; 21:2933-42.
51. Dankel S N, Fadnes D J, Stavrum A K, et al. Switch from stress response to homeobox transcription factors in adipose tissue after profound fat loss. PLoS One 2010; 5:e11033.
52. Methlie P, Dankel S, Myhra T, et al. Changes in adipose glucocorticoid metabolism before and after bariatric surgery assessed by direct hormone measurements. Obesity (Silver Spring) 2013; 21:2495-503.
53. Spalding K L, Amer E, Westermark P O, et al. Dynamics of fat cell turnover in humans. Nature 2008; 453:783-7.
54. Bossola, M., Pacelli, F. & Doglietto, G. B. Novel treatments for cancer cachexia. *Expert Opin Investig Drugs* 16, 1241-1253, doi:10.1517/13543784.16.8.1241 (2007).
55. Lainscak, M., Podbregar, M. & Anker, S. D. How does cachexia influence survival in cancer, heart failure and other chronic diseases? *Curr Opin Support Palliat Care* 1, 299-305, doi:10.1097/SPC.0b013e3282f31667 (2007).
56. Dhanapal, R., Saraswathi, T. & Govind, R. N. Cancer cachexia. *J Oral Maxillofac Pathol* 15, 257-260, doi: 10.4103/0973-029X.86670 (2011).
57. Petruzzelli, M. et al. A switch from white to brown fat increases energy expenditure in cancer-associated cachexia. *Cell Metab* 20, 433-447, doi:10.1016/j.cmet.2014.06.011 (2014).
58. Claussnitzer, M. et al. FTO Obesity Variant Circuitry and Adipocyte Browning in Humans. *New England Journal of Medicine* in press (2015).
59. von Haehling, S. & Anker, S. D. Cachexia vs obesity: where is the real unmet clinical need? *J Cachexia Sarcopenia Muscle* 4, 245-246, doi:10.1007/s13539-013-0124-8 (2013).
60. Kir, S. et al. Tumour-derived PTH-related protein triggers adipose tissue browning and cancer cachexia. *Nature* 513, 100-104, doi:10.1038/nature13528 (2014).

What is claimed is:

1. A method of treating a disorder mediated by a dysregulation of energy consumption in an adipocyte in a patient in need thereof, said method comprising administering an effective amount of one or more agents that modulate one or more of iroquois homeobox protein 3 (IRX3) function, iroquois homeobox protein 5 (IRX5) function, AT-rich interactive domain-containing protein 5B (ARID5B) function, obesity browning enhancer 1 (OBE1) function, or genetic variant rs1421085 function in the adipocyte, wherein the agent is one or more of a genome editing system, a small-interfering ribonucleic acid (siRNA), a microRNA (miRNA), an anti-sense ribonucleic acid (antisense RNA), or an anti-sense deoxyribonucleic acid (antisense DNA).

2. The method of claim 1, wherein the disorder is obesity, cardiovascular disease, or type 2 diabetes.

3. The method of claim 2, wherein the one or more agents decrease IRX3 function, decrease IRX5 function, decrease OBE1 function, increase ARID5B function, increase ARID5B binding to genetic variant rs1421085, increase ARID5B binding to OBE1, or any combination thereof.

4. The method of claim 1, wherein the disorder is cancer or cachexia.

5. The method of claim 4, wherein the cachexia is cachexia associated with cancer, acquired immune deficiency syndrome (AIDS), multiple sclerosis, tuberculosis, chronic obstructive lung disease, congestive heart failure, familial amyloid polyneuropathy, gadolinium poisoning, mercury poisoning (acrodynia), or hormonal deficiency.

6. The method of claim 4, wherein the one or more agents increase IRX3 function, increase IRX5 function, increase OBE1 function, decrease ARID5B function, or decrease ARID5B binding to genetic variant rs1421085, decrease ARID5B binding to OBE1, or any combination thereof.

7. The method of claim 1, wherein the adipocyte is one or more of a stem cell adipocyte precursor, mesenchymal stem cell, a preadipocyte, a mature white adipocyte, a mature beige adipocyte, or a mature brown adipocyte.

8. The method of claim 1, wherein the one or more agent is one or more of a small-interfering ribonucleic acid (siRNA), a microRNA (miRNA), an anti-sense ribonucleic acid (antisense RNA), or an anti-sense deoxyribonucleic acid (antisense DNA).

9. The method of claim 8, wherein the agent is an siRNA that targets IRX5.

10. The method of claim 1, wherein the agent is a genome editing system.

11. The method of claim 1, wherein the adipocyte is a human adipocyte.

12. The method of claim 1, wherein the one or more agents modulate one or more genes of IRX3, IRX5, ARID5B, OBE1, or genetic variant rs1421085.

13. The method of claim 1, wherein the one or more agents modulate one or more regulatory elements of IRX3, IRX5, or ARID5B.

14. The method of claim 1, wherein the one or more agents modulate one or more gene products of IRX3, IRX5, ARID5B, or OBE1.

15. The method of claim 1, wherein the genome editing system is a clustered regularly interspaced short palindromic repeat (CRISPR) system.

16. The method of claim 1, wherein the agent is an siRNA that targets IRX3 or IRX5.

17. The method of claim 16, wherein the agent is an siRNA that targets IRX3 and wherein the agent comprises one or more sequences selected from the group consisting of SEQ ID NOs: 1-15 and 17-18.

18. The method of claim 8, wherein the agent is an siRNA that targets IRX3.

19. The method of claim 17, wherein the agent comprises a mixture of siRNAs comprising one or more sequences selected from SEQ ID NOs: 1-3.

* * * * *